United States Patent
Yoshioka et al.

(10) Patent No.: US 12,239,713 B2
(45) Date of Patent: *Mar. 4, 2025

(54) DEGRADABLE POLYETHYLENE GLYCOL CONJUGATE

(71) Applicants: NOF CORPORATION, Tokyo (JP); TOKYO INSTITUTE OF TECHNOLOGY, Tokyo (JP)

(72) Inventors: Hiroki Yoshioka, Kanagawa (JP); Masaki Kamiya, Kawasaki (JP); Yuji Yamamoto, Kawasaki (JP); Midori Hirai, Kawasaki (JP); Akiko Sasaki, Kawasaki (JP); Nobuhiro Nishiyama, Tokyo (JP); Makoto Matsui, Tokyo (JP); Hiroyasu Takemoto, Tokyo (JP); Kazuki Miyauchi, Tokyo (JP); Takahiro Nomoto, Tokyo (JP); Keishiro Tomoda, Tokyo (JP)

(73) Assignees: NOF CORPORATION, Tokyo (JP); TOKYO INSTITUTE OF TECHNOLOGY, Tokyo (JP)

(*) Notice: Subject to any disclaimer, the term of this patent is extended or adjusted under 35 U.S.C. 154(b) by 524 days.

This patent is subject to a terminal disclaimer.

(21) Appl. No.: 17/042,039

(22) PCT Filed: Mar. 29, 2019

(86) PCT No.: PCT/JP2019/014245
§ 371 (c)(1),
(2) Date: Sep. 25, 2020

(87) PCT Pub. No.: WO2019/189853
PCT Pub. Date: Oct. 3, 2019

(65) Prior Publication Data
US 2021/0023231 A1    Jan. 28, 2021

(30) Foreign Application Priority Data
Mar. 29, 2018  (JP) ................. 2018-064306

(51) Int. Cl.
*A61K 47/60*    (2017.01)
*A61K 38/19*    (2006.01)
(Continued)

(52) U.S. Cl.
CPC ............ *A61K 47/60* (2017.08); *A61K 38/193* (2013.01); *A61K 38/23* (2013.01); *A61K 38/27* (2013.01);
(Continued)

(58) Field of Classification Search
CPC ...... A61K 47/60; A61K 38/193; A61K 38/23; A61K 38/27; A61K 47/65; A61K 31/7088; A61K 38/19; A61K 38/22; A61K 38/43; A61K 39/44; A61K 48/00; A61K 38/05; A61K 35/06; A61K 38/07; A61K 38/08; C07K 5/1008; C07K 7/06; C07K 19/00; C07K 5/06078; C07K 5/0806; C07K 5/0808; C07K 5/04; C07K 14/535; C07K 14/585; C07K 14/61; C07K 17/02; C07K 5/0802; C07K 5/06008; C08G 65/33396; C08G 65/329; C08G 65/33337; C08G 65/3332; A61P 5/00; A61P 43/00

See application file for complete search history.

(56) References Cited

U.S. PATENT DOCUMENTS 6,828,412 B1  12/2004  Brocchini et al.
8,088,365 B2 *  1/2012  Harris .................... A61K 47/60
                                                424/78.19
(Continued)

FOREIGN PATENT DOCUMENTS

JP    2007-112924 A    5/2007
JP    2009-527581 A    7/2009
(Continued)

OTHER PUBLICATIONS

European Medicines Agency, "Chmp Safety Working Party's Response to PDCO regarding the use of PEGylated drug products in the paediatric population," EMA/CHMP/SWP/647258/2012 (Nov. 16, 2012).

Rudmann et al., "High Molecular Weight Polyethylene Glycol Cellular Distribution and PEG-associated Cytoplasmic Vacuolation is Molecular Weight Dependent and Does Not Require Conjugation to Proteins," Toxicol. Pathol., 41(7): 970-983 (2013).

Veronese et al., "PEG-Doxorubicin Conjugates: Influence of Polymer Structure on Drug Release, in Vitro Cytotoxicity, Biodistribution, and Antitumor Activity," Bioconjug. Chem., 16: 775-784 (2005).

(Continued)

*Primary Examiner* — Sudhakar Katakam
(74) *Attorney, Agent, or Firm* — Leydig, Voit & Mayer, Ltd.

(57) ABSTRACT

The invention provides a bio-related substance bonded to a high-molecular-weight polyethylene glycol derivative that does not cause vacuolation of cells. The bio-related substance bonded to a degradable polyethylene glycol derivative is represented by the formula (A):

formula (A)

$$D\!-\!\!\left[L^5\!-\!Q\!-\!\!\left[L^1\!-\!\!\left(CH_2CH_2O\right)_{\overline{n1}}\!L^2\!-\!Z\!-\!L^3\right]_{\overline{m}}\!L^4\!-\!\!\left(CH_2CH_2O\right)_{\overline{n2}}\!R\right\}_p\right]_y$$

wherein m is 1-7, n1 and n2 are each independently 45-682, p is 1-4, R is an alkyl group having 1-4 carbon atoms, Z is an oligopeptide with 2-8 residues composed of neutral amino acids excluding cysteine, Q is a residue of a compound having 2-5 active hydrogens, D is the bio-related substance, L1, L2, L3, L4 and L5 are each independently a single bond or a divalent spacer, and y is 1-40.

14 Claims, 12 Drawing Sheets

Specification includes a Sequence Listing.

(51) Int. Cl.
*A61K 38/23* (2006.01)
*A61K 38/27* (2006.01)
*C07K 5/103* (2006.01)
*C07K 7/06* (2006.01)
*C07K 19/00* (2006.01)
*C08G 65/333* (2006.01)

(52) U.S. Cl.
CPC .............. *C07K 5/1008* (2013.01); *C07K 7/06* (2013.01); *C07K 19/00* (2013.01); *C08G 65/33396* (2013.01)

(56) References Cited

U.S. PATENT DOCUMENTS

| | | |
|---|---|---|
| 8,309,680 B2 | 11/2012 | McManus et al. |
| 8,835,599 B2 | 9/2014 | McManus et al. |
| 2003/0228275 A1 | 12/2003 | Ekwuribe et al. |
| 2009/0023859 A1 | 1/2009 | Sakanoue et al. |
| 2010/0010158 A1 | 1/2010 | McManus et al. |
| 2013/0072709 A1 | 3/2013 | McManus et al. |

FOREIGN PATENT DOCUMENTS

| | | |
|---|---|---|
| WO | 2000/066091 A1 | 11/2000 |
| WO | 2005/108463 A2 | 11/2005 |

OTHER PUBLICATIONS

Yang et al., "Synthesis and Characterization of Enzymatically Degradable PEG-Based Peptide-Containing Hydrogels," *Macromol. Biosci.*, 10(4): 445-454 (2010).

Japanese Patent Office, International Search Report in International Patent Application No. PCT/JP2019/014245 (Jul. 2, 2019).

* cited by examiner

DEGRADABLE POLYETHYLENE GLYCOL CONJUGATE

CROSS-REFERENCE TO RELATED APPLICATIONS

This patent application is the U.S. national phase of International Patent Application No. PCT/JP2019/014245, filed on Mar. 29, 2019, which claims the benefit of Japanese Patent Application No. 2018-064306 filed on Mar. 29, 2018, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 4,984 bytes ASCII (Text) file named "750838ReplacementSequenceListing.txt" created May 25, 2023.

TECHNICAL FIELD

The present invention relates to a bio-related substance bonded to a degradable polyethylene glycol derivative that is degraded in the cells.

BACKGROUND ART

Pharmaceutical products that use bio-related substances such as hormone, cytokine, antibody, and enzyme are generally rapidly discharged from the body after administration to the body due to glomerular filtration in the kidney and uptake by macrophages in the liver and spleen. Therefore, the half-life in blood is short, and it is often difficult to obtain a sufficient pharmacological effect. To solve this problem, attempts have been made to chemically modify bio-related substances with sugar chain, hydrophilic polymers such as polyethylene glycol, albumin and the like. As a result, it becomes possible to prolong the blood half-life of bio-related substances by increasing the molecular weight, forming a hydration layer, and the like. In addition, it is also well known that modification with polyethylene glycol provides effects such as reduction of toxicity and antigenicity of bio-related substances, and improvement of solubility of hardly water-soluble drugs.

The bio-related substances modified with polyethylene glycol are covered with a hydration layer formed by an ether bond of polyethylene glycol and a hydrogen bond with water molecule, has an increased molecular size, and thus can avoid glomerular filtration in the kidney. Furthermore, it is known that the interaction with opsonin and the cell surface that constitutes each tissue decreases, and the migration to each tissue decreases. Polyethylene glycol is a superior material that extends the blood half-life of bio-related substances, and it has been found as regards the property thereof that a higher effect is obtained when the molecular weight is higher. Many studies have been made on bio-related substances modified with high-molecular-weight polyethylene glycol with a molecular weight of not less than 40,000, and the results show that the half-life in blood thereof can be significantly extended.

Polyethylene glycol is regarded as the optimum standard among the modifiers used for improving the property of bio-related substances. At present, a plurality of polyethylene glycol modified formulations are placed on the market and are used in medical sites. On the other hand, the European Medicines Agency (EMA) reported in 2012 that administration of a bio-related substance modified with high-molecular-weight polyethylene glycol with a molecular weight of 40,000 or more to an animal for a long time at a certain dose or above led to a phenomenon of the generation of vacuoles in the cells of a part of the tissues (non-patent document 1). In consideration of the facts that there is no report at present that the vacuole formation itself has an adverse effect on the human body, and the dose used in the above EMA report is extremely high compared to the dose generally applied in medical sites, the safety of therapeutic preparations modified with polyethylene glycol having a molecular weight of 40,000 or more which are currently manufactured and sold does not pose any problem. However, in the treatment of very special diseases (for example, dwarfism), it may be assumed that a treatment protocol in which a polyethylene glycol-modified preparation is administered to a patient at a high dose for a long period of time will be adopted. Therefore, it is expected that a potential demand exists for the development of a polyethylene glycol-modified preparation that does not cause vacuole formation in cells and can be applied even in such a special situation.

In non-patent document 2, a large excess of polyethylene glycol alone was administered to animals for a long term compared to the dose of general polyethylene glycol-modified preparations. As a result, vacuole was not seen at a molecular weight of 20,000, and the generation of vacuole was confirmed at a molecular weight of 40,000. One of the means to suppress vacuoles is to reduce the molecular weight of polyethylene glycol. However, reducing the molecular weight causes a problem that the half-life in blood of bio-related substances cannot be improved sufficiently.

There are reports relating to the technique for degrading high-molecular-weight polyethylene glycol into low-molecular-weight polyethylene glycol in the body and promoting excretion from the kidney.

Patent document 1 describes a polyethylene glycol derivative having a sulfide bond or peptide binding site that is cleaved in vivo. It is described that the polyethylene glycol derivative is degraded in vivo to a molecular weight suitable for excretion from the kidney. However, no specific data relating to the degradation is shown, nor is there any data on enhanced excretion from the kidney. Furthermore, there is no description about the vacuoles in cells.

Patent document 2 describes a polyethylene glycol derivative having an acetal site that can be hydrolyzed under low pH environment in the body. It is described that the polyethylene glycol derivative is degraded in vivo to a molecular weight suitable for excretion from the kidney. However, no specific data on enhanced excretion from the kidney is shown. Furthermore, there is no description about the vacuoles in cells. In addition, the hydrolyzable acetal moiety is known to gradually degrade also in blood, and it is expected that the half-life in blood of modified bio-related substances cannot be improved sufficiently.

On the other hand, there are reports on polyethylene glycol derivatives containing degradable oligopeptides introduced thereinto for effective release of drugs, hydrogels that degrade in the body, and the like.

Non-patent document 3 describes a polyethylene glycol derivative having an oligopeptide moiety that is degraded by enzymes. Here, the oligopeptide was introduced as a linker between an anticancer agent and polyethylene glycol, and it has been reported that the oligopeptide is degraded by the enzyme specifically expressed around the tumor, and the anticancer agent is efficiently released. The purpose is release of an anticancer agent, and the degradability is not imparted to polyethylene glycol for the purpose of suppressing cell vacuoles.

Non-patent document 4 describes hydrogels using cross-linking molecules having an oligopeptide moiety that is degraded by enzymes and a multi-branched polyethylene glycol derivative. Here, the oligopeptide is used as a cross-linking molecule that connects the multi-branched polyethylene glycol derivative, and can further impart degradability by enzymes to the hydrogel. It aims to prepare a degradable hydrogel, where the degradability is not imparted to polyethylene glycol for the purpose of suppressing cell vacuoles.

Patent document 3 describes a branched polyethylene glycol derivative with oligopeptide as the skeleton. Here, oligopeptide is used as the basic skeleton of polyethylene glycol derivatives and does not impart degradability by enzymes. It is characterized by containing amino acids having an amino group or a carboxyl group in the side chain, such as lysine and aspartic acid, in the oligopeptide, and aims to synthesize a branched polyethylene glycol derivative by utilizing them in the reaction. Patent document 3 is not directed to a polyethylene glycol derivative for the purpose of suppressing cell vacuoles.

As described above, a high-molecular-weight polyethylene glycol derivative that is stable in blood, sufficiently improves half-life in blood of modified bio-related substances, is specifically degraded in cell after incorporation into the cell, and can suppress generation of vacuoles in cells is demanded.

DOCUMENT LIST

Patent Documents patent document 1: National Publication of International Patent Application No. 2009-527581 patent document 2: WO 2005/108463 patent document 3: WO 2006/088248

Non-Patent Documents non-patent document 1: EMA/CHMP/SWP/647258/2012 non-patent document 2: Daniel G. Rudmann, et al., Toxicol. Pathol., 41, 970-983(2013)

non-patent document 3: Francesco M Veronese, et al., Bioconjugate Chem., 16, 775-784(2005)

non-patent document 4: Jiyuan Yang, et al., Marcomol. Biosci., 10(4), 445-454(2010)

SUMMARY OF INVENTION

Technical Problem

The problem of the present invention is to provide a bio-related substance bonded to a high-molecular-weight polyethylene glycol derivative that does not cause vacuolation of cells. More specifically, it is to provide a bio-related substance with sufficiently improved half-life in blood that is stable in the blood of living organisms, and modified by a degradable polyethylene glycol derivative that is degraded in cells.

Solution to Problem

The present inventors have conducted intensive studies in an attempt to solve the aforementioned problems and invented a bio-related substance bonded to a degradable polyethylene glycol derivative having an oligopeptide that degrades in cells.

Accordingly, the present invention provides the following.

[1] A bio-related substance bonded to a degradable polyethylene glycol derivative, and represented by the following formula (A):

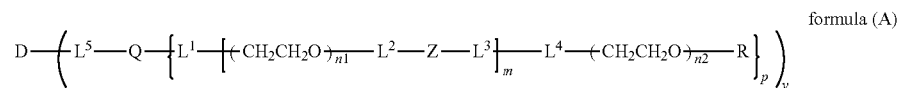

formula (A)

wherein m is 1-7, n1 and n2 are each independently 45-682, p is 1-4, R is an alkyl group having 1-4 carbon atoms, Z is an oligopeptide with 2-8 residues composed of neutral amino acids excluding cysteine, Q is a residue of a compound having 2-5 active hydrogens, D is the bio-related substance, $L^1$, $L^2$, $L^3$, $L^4$ and $L^5$ are each independently a single bond or a divalent spacer, and y is 1-40.

[2] The bio-related substance of [1], which is a bio-related substance bonded to a degradable polyethylene glycol derivative, and represented by the following formula (1):

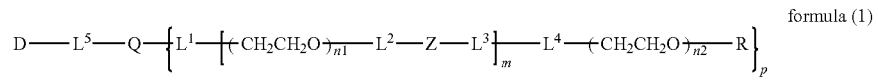

formula (1)

wherein m is 1-7, n1 and n2 are each independently 45-682, p is 1-4, R is an alkyl group having 1-4 carbon atoms, Z is an oligopeptide with 2-8 residues composed of neutral amino acids excluding cysteine, Q is a residue of a compound having 2-5 active hydrogens, D is the bio-related substance, and $L^1$, $L^2$, $L^3$, $L^4$ and $L^5$ are each independently a single bond or a divalent spacer.

[3] The bio-related substance of [1] or [2], wherein Q is a residue of ethylene glycol, lysine, aspartic acid, glutamic acid, glycerol, pentaerythritol, diglycerol or xylitol.

[4] The bio-related substance of [1] or [2], wherein Q is a residue of an oligopeptide, and the oligopeptide has 4 to 8 residues and comprises any one of lysine, aspartic acid, and glutamic acid, and neutral amino acids excluding cysteine as the other amino acids.

[5] The bio-related substance of [4], wherein the oligopeptide for Q is an oligopeptide having glycine as C-terminal amino acid.

[6] The bio-related substance of [4] or [5], wherein the oligopeptide for Q is an oligopeptide having at least one hydrophobic neutral amino acid having a hydropathy index of not less than 2.5.

[7] The bio-related substance of any one of [1] to [6], wherein the oligopeptide for Z is an oligopeptide having glycine as the C-terminal amino acid.

[8] The bio-related substance of any one of [1] to [7], wherein the oligopeptide for Z is an oligopeptide having at least one hydrophobic neutral amino acid having a hydropathy index of not less than 2.5.

[9] The bio-related substance of any one of [1] to [8], wherein the degradable polyethylene glycol derivative bonded to D has a molecular weight per one molecule of not less than 30,000.

[10] The bio-related substance of any one of [1] to [9], wherein $L^1$, $L^2$, $L^3$, $L^4$ and $L^5$ are each independently a single bond, a phenylene group, an amide bond, an ether bond, a thioether bond, a urethane bond, a secondary amino group, a carbonyl group, a urea bond, a triazine group, a bond of maleimide and thiol, an oxime bond, or an alkylene group optionally comprising such bond or group.

[11] The bio-related substance of any one of [1] to [10], wherein the bio-related substance for D is a hormone, a cytokine, an antibody, an aptamer or an enzyme.

[12] The bio-related substance of any one of [1] to [11], wherein the bio-related substance for D is an insulin, a calcitonin, a human growth hormone, an interferon, a granulocyte colony stimulating factor, an erythropoietin or an antibody fragment.

[13] The bio-related substance of [2], wherein Z in the formula (1) is composed of $Z^1$, A and glycine residue, which is a bio-related substance bonded to a degradable polyethylene glycol derivative, and represented by the following formula (2):

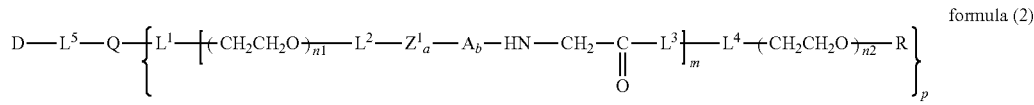

formula (2)

wherein m is 1-7, n1 and n2 are each independently 45-682, p is 1-4, R is an alkyl group having 1-4 carbon atoms, $Z^1$ is an oligopeptide with 2-6 residues composed of neutral amino acids excluding cysteine, A is a neutral amino acid excluding cysteine, a and b are each independently 0 or 1, and (a+b)≥1, Q is a residue of a compound having 2-5 active hydrogens, D is the bio-related substance, and $L^1$, $L^2$, $L^3$, $L^4$ and $L^5$ are each independently a single bond or a divalent spacer.

[14] The bio-related substance of [13], wherein Q is a residue of ethylene glycol, lysine, aspartic acid, glutamic acid, glycerol, pentaerythritol, diglycerol or xylitol.

[15] The bio-related substance of [13], wherein Q is a residue of an oligopeptide, and the oligopeptide has 4 to 8 residues and comprises any one of lysine, aspartic acid, and glutamic acid, and neutral amino acids excluding cysteine as the other amino acids.

[16] The bio-related substance of [15], wherein the oligopeptide for Q is an oligopeptide having glycine as C-terminal amino acid.

[17] The bio-related substance of [15] or [16], wherein the oligopeptide for Q is an oligopeptide having at least one hydrophobic neutral amino acid having a hydropathy index of not less than 2.5.

[18] The bio-related substance of any one of [13] to [17], wherein the oligopeptide for $Z^1$ is an oligopeptide having at least one hydrophobic neutral amino acid having a hydropathy index of not less than 2.5.

[19] The bio-related substance of any one of [13] to [18], wherein the neutral amino acid for A is a hydrophobic neutral amino acid having a hydropathy index of not less than 2.5.

[20] The bio-related substance of any one of [13] to [19], wherein the degradable polyethylene glycol derivative bonded to D has a molecular weight per one molecule of not less than 30,000.

[21] The bio-related substance of any one of [13] to [20], wherein $L^1$, $L^2$, $L^3$, $L^4$ and $L^5$ are each independently a single bond, a phenylene group, an amide bond, an ether bond, a thioether bond, a urethane bond, a secondary amino group, a carbonyl group, a urea bond, a triazine group, a bond of maleimide and thiol, an oxime bond, or an alkylene group optionally comprising such bond or group.

[22] The bio-related substance of any one of [13] to [21], wherein the bio-related substance for D is a hormone, a cytokine, an antibody, an aptamer or an enzyme.

[23] The bio-related substance of any one of [13] to [22], wherein the bio-related substance for D is an insulin, a calcitonin, a human growth hormone, an interferon, a granulocyte colony stimulating factor, an erythropoietin or an antibody fragment.

[24] The bio-related substance of [13], wherein m in the formula (2) is 1, which is a bio-related substance bonded to a degradable polyethylene glycol derivative, and represented by the following formula (3):

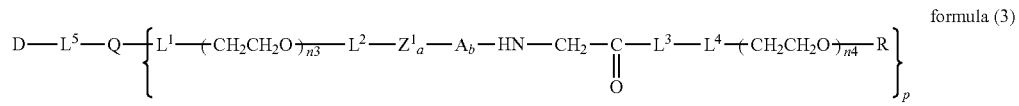

formula (3)

wherein n3 and n4 are each independently 45-682, p is 1-4, R is an alkyl group having 1-4 carbon atoms, $Z^1$ is an oligopeptide with 2-6 residues composed of neutral amino acids excluding cysteine, A is a neutral amino acid excluding cysteine, a and b are each independently 0 or 1, and (a+b)≥1, Q is a residue of a compound having 2-5 active hydrogens, D is the bio-related substance, and $L^1$, $L^2$, $L^3$, $L^4$ and $L^5$ are each independently a single bond or a divalent spacer.

[25] The bio-related substance of [24], wherein Q is a residue of ethylene glycol, lysine, aspartic acid, glutamic acid, glycerol, pentaerythritol, diglycerol or xylitol.

[26] The bio-related substance of [24], wherein Q is a residue of an oligopeptide, and the oligopeptide has 4 to 8 residues and comprises any one of lysine, aspartic acid, and glutamic acid, and neutral amino acids excluding cysteine as the other amino acids.

[27] The bio-related substance of [26], wherein the oligopeptide for Q is an oligopeptide having glycine as C-terminal amino acid.

[28] The bio-related substance of [26] or [27], wherein the oligopeptide for Q is an oligopeptide having at least one hydrophobic neutral amino acid having a hydropathy index of not less than 2.5.

[29] The bio-related substance of any one of [24] to [28], wherein the oligopeptide for $Z^1$ is an oligopeptide having at least one hydrophobic neutral amino acid having a hydropathy index of not less than 2.5.

[30] The bio-related substance of any one of [24] to [29], wherein the neutral amino acid for A is a hydrophobic neutral amino acid having a hydropathy index of not less than 2.5.

[31] The bio-related substance of any one of [24] to [30], wherein the degradable polyethylene glycol derivative bonded to D has a molecular weight per one molecule of not less than 30,000.

[32] The bio-related substance of any one of [24] to [31], wherein $L^1$, $L^2$, $L^3$, $L^4$ and $L^5$ are each independently a single bond, a phenylene group, an amide bond, an ether bond, a thioether bond, a urethane bond, a secondary amino group, a carbonyl group, a urea bond, a triazine group, a bond of maleimide and thiol, an oxime bond, or an alkylene group optionally comprising such bond or group.

[33] The bio-related substance of any one of [24] to [32], wherein the bio-related substance for D is a hormone, a cytokine, an antibody, an aptamer or an enzyme.

[34] The bio-related substance of any one of [24] to [33], wherein the bio-related substance for D is an insulin, a calcitonin, a human growth hormone, an interferon, a granulocyte colony stimulating factor, an erythropoietin or an antibody fragment.

[35] The bio-related substance of [2], wherein, in the formula (1), Q is a residue of ethylene glycol, $L^1$ is $CH_2CH_2O$, and p is 1, which is a bio-related substance bonded to a degradable polyethylene glycol derivative, and represented by the following formula (4):

formula (4)

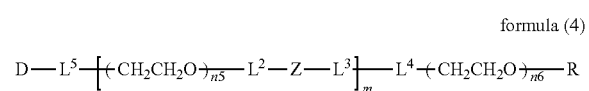

wherein m is 1-7, n5 and n6 are each independently 113-682, R is an alkyl group having 1-4 carbon atoms, Z is an oligopeptide with 2-8 residues composed of neutral amino acids excluding cysteine, D is the bio-related substance, $L^2$, $L^3$, $L^4$ and $L^5$ are each independently a single bond or a divalent spacer.

[36] The bio-related substance of [35], wherein the oligopeptide for Z is an oligopeptide having glycine as the C-terminal amino acid.

[37] The bio-related substance of [35] or [36], wherein the oligopeptide for Z is an oligopeptide having at least one hydrophobic neutral amino acid having a hydropathy index of not less than 2.5.

[38] The bio-related substance of any one of [35] to [37], wherein the degradable polyethylene glycol derivative bonded to D has a molecular weight per one molecule of not less than 30,000.

[39] The bio-related substance of any one of [35] to [38], wherein $L^2$, $L^3$, $L^4$ and $L^5$ are each independently a single bond, a phenylene group, an amide bond, an ether bond, a thioether bond, a urethane bond, a secondary amino group, a carbonyl group, a urea bond, a triazine group, a bond of maleimide and thiol, an oxime bond, or an alkylene group optionally comprising such bond or group.

[40] The bio-related substance of any one of [35] to [39], wherein the bio-related substance for D is a hormone, a cytokine, an antibody, an aptamer or an enzyme.

[41] The bio-related substance of any one of [35] to [40], wherein the bio-related substance for D is an insulin, a calcitonin, a human growth hormone, an interferon, a granulocyte colony stimulating factor, an erythropoietin or an antibody fragment.

[42] The bio-related substance of [13], wherein, in the formula (2), Q is a residue of ethylene glycol, $L^1$ is $CH_2CH_2O$, and p is 1, which is a bio-related substance bonded to a degradable polyethylene glycol derivative, and represented by the following formula (5):

formula (5)

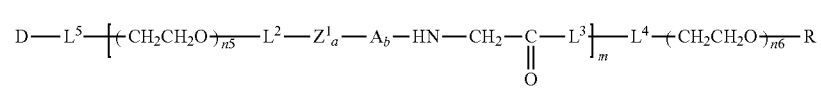

wherein m is 1-7, n5 and n6 are each independently 113-682, R is an alkyl group having 1-4 carbon atoms, $Z^1$ is an oligopeptide with 2-6 residues composed of neutral amino acids excluding cysteine, A is a neutral amino acid excluding cysteine, a and b are each independently 0 or 1, and (a+b)≥1, D is the bio-related substance, $L^2$, $L^3$, $L^4$ and $L^5$ are each independently a single bond or a divalent spacer.

[43] The bio-related substance of [42], wherein the oligopeptide for $Z^1$ is an oligopeptide having at least one hydrophobic neutral amino acid having a hydropathy index of not less than 2.5.

[44] The bio-related substance of [42] or [43], wherein the neutral amino acid for A is a hydrophobic neutral amino acid having a hydropathy index of not less than 2.5.

[45] The bio-related substance of any one of [42] to [44], wherein the degradable polyethylene glycol derivative bonded to D has a molecular weight per one molecule of not less than 30,000.

[46] The bio-related substance of any one of [42] to [45], wherein $L^2$, $L^3$, $L^4$ and $L^5$ are each independently a single bond, a phenylene group, an amide bond, an ether bond, a thioether bond, a urethane bond, a secondary amino group, a carbonyl group, a urea bond, a triazine group, a bond of maleimide and thiol, an oxime bond, or an alkylene group optionally comprising such bond or group.

[47] The bio-related substance of any one of [42] to [46], wherein the bio-related substance for D is a hormone, a cytokine, an antibody, an aptamer or an enzyme.

[48] The bio-related substance of any one of [42] to [47], wherein the bio-related substance for D is an insulin, a calcitonin, a human growth hormone, an interferon, a granulocyte colony stimulating factor, an erythropoietin or an antibody fragment.

[49] The bio-related substance of [24], wherein, in the formula (3), Q is a residue of ethylene glycol, $L^1$ is $CH_2CH_2O$, and p is 1, which is a bio-related substance bonded to a degradable polyethylene glycol derivative, and represented by the following formula (6):

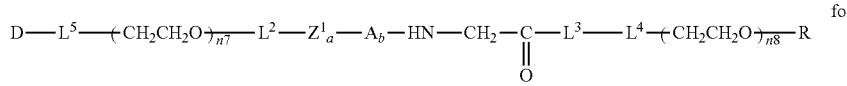

formula (6)

wherein n7 and n8 are each independently 226-682, R is an alkyl group having 1-4 carbon atoms, $Z^1$ is an oligopeptide with 2-6 residues composed of neutral amino acids excluding cysteine, A is a neutral amino acid excluding cysteine, a and b are each independently 0 or 1, and (a+b)≥1, D is the bio-related substance, $L^2$, $L^3$, $L^4$ and $L^5$ are each independently a single bond or a divalent spacer.

[50] The bio-related substance of [49], wherein the oligopeptide for $Z^1$ is an oligopeptide having at least one hydrophobic neutral amino acid having a hydropathy index of not less than 2.5.

[51] The bio-related substance of [49] or [50], wherein the neutral amino acid for A is a hydrophobic neutral amino acid having a hydropathy index of not less than 2.5.

[52] The bio-related substance of any one of [49] to [51], wherein the degradable polyethylene glycol derivative bonded to D has a molecular weight per one molecule of not less than 30,000.

[53] The bio-related substance of any one of [49] to [51], wherein $L^2$, $L^3$, $L^4$ and $L^5$ are each independently a single bond, a phenylene group, an amide bond, an ether bond, a thioether bond, a urethane bond, a secondary amino group, a carbonyl group, a urea bond, a triazine group, a bond of maleimide and thiol, an oxime bond, or an alkylene group optionally comprising such bond or group.

[54] The bio-related substance of any one of [49] to [52], wherein the bio-related substance for D is a hormone, a cytokine, an antibody, an aptamer or an enzyme.

[55] The bio-related substance of any one of [49] to [54], wherein the bio-related substance for D is an insulin, a calcitonin, a human growth hormone, an interferon, a granulocyte colony stimulating factor, an erythropoietin or an antibody fragment.

Advantageous Effects of Invention

In the bio-related substance bonded to a degradable polyethylene glycol derivative of the present invention, the degradable polyethylene glycol derivative is stable in blood in the body because it has an oligopeptide between the polyethylene glycol chains which is degraded by intracellular enzymes and can impart, to the bio-related substance, a half-life in blood that is equivalent to that of conventional polyethylene glycol derivatives without degradability. Thus, when the degradable polyethylene glycol derivative is incorporated into cells, the oligopeptide moiety between the polyethylene glycol chains is rapidly degraded, thus suppressing the generation of vacuoles in cells which has been a problem to date.

DESCRIPTION OF EMBODIMENTS

Figure 1:
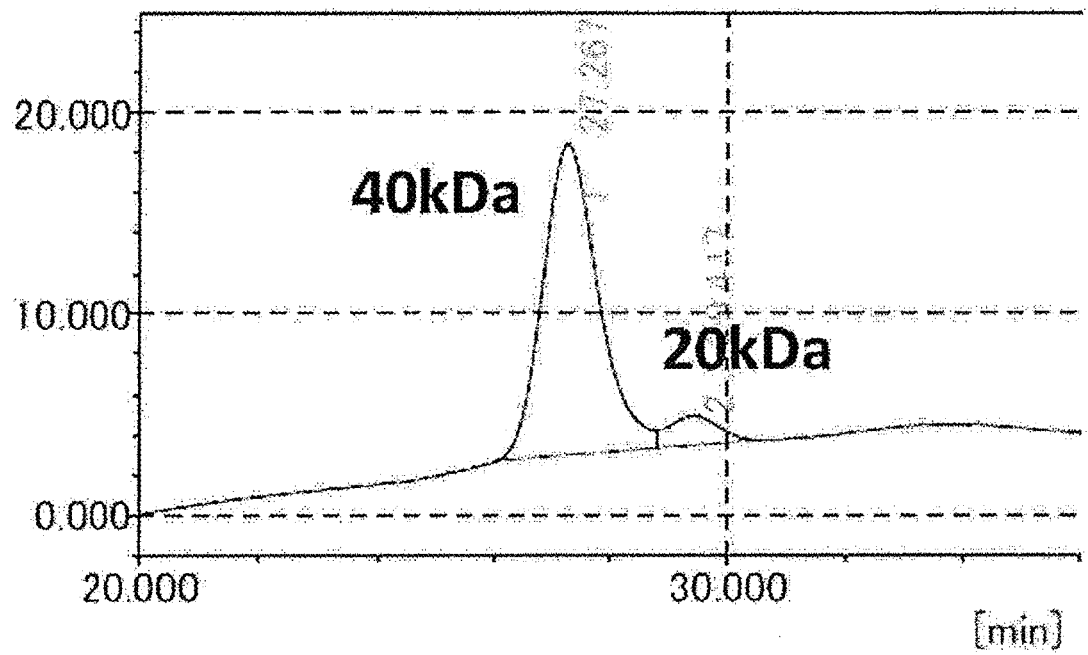
FIG. 1 shows GPC analysis results of ME-200GLFG (SEQ ID NO: 4) (L)-200PA of Example 1.

The present invention is explained in detail in the following.

The bio-related substance bonded to a degradable polyethylene glycol derivative of the present invention is represented by the following formula (A):

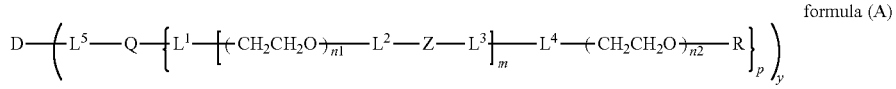

formula (A)

wherein m is 1-7, n1 and n2 are each independently 45-682, p is 1-4, R is an alkyl group having 1-4 carbon atoms, Z is an oligopeptide with 2-8 residues composed of neutral amino acids excluding cysteine, Q is a residue of a compound having 2-5 active hydrogens, D is the bio-related substance, $L^1$, $L^2$, $L^3$, $L^4$ and $L^5$ are each independently a single bond or a divalent spacer, and y is 1-40.

The number of molecules of a degradable polyethylene glycol derivative bonded to a bio-related substance in the present invention is shown by y in the formula (A), and is generally 1-40, preferably 1-20, more preferably 1-10, particularly preferably 1.

The effects afforded by increasing the number of molecules of the degradable polyethylene glycol derivative bonded to a bio-related substance include extended half-life in blood, reduced antigenicity and the like. However, the activity may be reduced depending on the bio-related substance. It is known that the activity of a bio-related substance such as an enzyme does not decrease even when a plurality of polyethylene glycol derivatives are bonded.

A degradable polyethylene glycol derivative bonded to a bio-related substance and having the number of molecules of 1, that is, the formula (A) wherein y is 1 is explained below.

The bio-related substance bonded to a degradable polyethylene glycol derivative of the present invention is shown by the following formula (1):

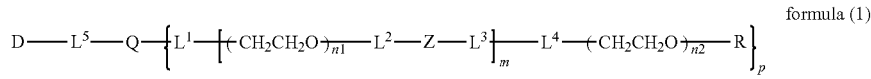

formula (1)

wherein m is 1-7, n1 and n2 are each independently 45-682, p is 1-4, R is an alkyl group having 1-4 carbon atoms, Z is an oligopeptide with 2-8 residues composed of neutral amino acids excluding cysteine, Q is a residue of a compound having 2-5 active hydrogens, D is the bio-related substance, and $L^1$, $L^2$, $L^3$, $L^4$ and $L^5$ are each independently a bond or a divalent spacer.

The molecular weight per one molecule of the polyethylene glycol derivative of the formula (1) of the present invention, which is bonded to bio-related substance D, is generally 4,000-160,000, preferably 10,000-120,000, further preferably 30,000-80,000. In one preferred embodiment of the present invention, the molecular weight per one molecule of the polyethylene glycol derivative of the formula (1) of the present invention is not less than 30,000. The molecular weight here is a number average molecular weight (Mn).

In the formula (1), n1 and n2 are each a repeating unit number of polyethylene glycol. Generally, they are each independently 45-682, preferably each independently 113-568, further preferably each independently 180-525. n1 and n2 may be different or the same.

In the formula (1), p is 1-4. When p is 1, the polyethylene glycol derivative moiety in the formula (1) is a straight chain type, and when p is 2-4, the polyethylene glycol derivative moiety in the formula (1) is a branched type.

In the formula (1), R is an alkyl group having 1-4 carbon atoms, and specific examples include a methyl group, an ethyl group, a propyl group, an isopropyl group, a butyl group, a t-butyl group and the like. It is preferably an alkyl group having 1-3 carbon atoms, more preferably a methyl group or an ethyl group, further preferably a methyl group.

In the formula (1), Z is not particularly limited as long as it is an oligopeptide stable in the blood of living organisms, and degraded by enzyme in cells. It is preferably an oligopeptide with 2-8 residues composed of neutral amino acids excluding cysteine, more preferably an oligopeptide with 2-6 residues composed of neutral amino acids excluding cysteine, further preferably an oligopeptide with 2-4 residues composed of neutral amino acids excluding cysteine.

In the formula (1), Z is preferably an oligopeptide composed of an amino acid having an amino group and a carboxyl group in the side chain, specifically, neutral amino acids not including lysine, aspartic acid, or glutamic acid. In the synthesis of the polyethylene glycol derivative moiety in the formula (1) of the present invention, the N-terminal amino group or the C-terminal carboxyl group of oligopeptide is used for the reaction with the polyethylene glycol derivative when introducing the oligopeptide into the polyethylene glycol derivative. However, when an amino acid having an amino group and a carboxyl group in the side chain is contained in the oligopeptide, impurity in which the polyethylene glycol derivative is introduced into not only the intended N-terminal amino group or C-terminal carboxyl group, but also amino group or carboxyl group in the side chain are generated. Since this impurity is difficult to remove by a purification step such as general extraction or crystallization, to obtain the desired product with high purity, it is desirable to use an oligopeptide composed of amino acids having no amino group or carboxyl group in the side chain. The amino acids to be used here are α-amino acids and are basically in the L form.

Cysteine, which is a neutral amino acid, has a thiol group and forms a disulfide bond with other thiol groups. Thus, in the formula (1), Z is desirably an oligopeptide composed of neutral amino acids not including cysteine.

In the formula (1), moreover, Z is preferably an oligopeptide having glycine as the C-terminal amino acid. When a C-terminal carboxyl group is reacted with a polyethylene glycol derivative, it is basically necessary to activate the C-terminal carboxyl group with a condensing agent and the like. It is known that epimerization tends to occur in amino acids other than glycine and stereoisomer is by-produced in this activation step. By using an achiral glycine as the C-terminal amino acid of the oligopeptide, a highly pure target product free from by-production of stereoisomer can be obtained.

In the formula (1), moreover, Z is preferably a hydrophobic neutral amino acid having a hydropathy index of not less than 2.5, specifically, an oligopeptide having at least one of phenylalanine, leucine, valine, and isoleucine, more preferably an oligopeptide having phenylalanine. The hydropathic index (hydropathy index) created by Kyte and Doolittle that quantitatively indicates the hydrophobicity of amino acid shows that the larger the value, the more hydrophobic the amino acid (Kyte J & Doolittle R F, 1982, J Mol Biol, 157:105-132.).

In the formula (1), Z is not particularly limited as long as it is an oligopeptide with 2-8 residues composed of neutral amino acids excluding cysteine which is stable in the blood of living organisms, and has property of degradation by an enzyme in cells. Specific examples include glycine-phenylalanine-leucine-glycine (SEQ ID NO: 4), glycine-glycine-phenylalanine-glycine (SEQ ID NO: 5), glycine-phenylalanine-glycine, glycine-leucine-glycine, valine-citrulline-glycine, valine-alanine-glycine, glycine-glycine-glycine, phenylalanine-glycine and the like. It is preferably glycine-phenylalanine-leucine-glycine (SEQ ID NO: 4), glycine-glycine-phenylalanine-glycine (SEQ ID NO: 5), glycine-phenylalanine-glycine, glycine-glycine-glycine, valine-citrulline-glycine, valine-alanine-glycine, phenylalanine-glycine, more preferably glycine-phenylalanine-leucine-glycine (SEQ ID NO: 4), glycine-phenylalanine-glycine, valine-citrulline-glycine, valine-alanine-glycine, or phenylalanine-glycine, further more preferably glycine-phenylalanine-leucine-glycine (SEQ ID NO: 4), valine-citrulline-glycine, or phenylalanine-glycine.

In the formula (1), Q is a residue of a compound having 2-5 active hydrogens. The active hydrogen is, for example, hydrogen of hydroxyl group, carboxyl group, amino group or the like (in the present invention, active hydrogen is counted as one in the case of primary amino group (—NH$_2$)). As the "residue of a compound having two active hydrogens", residues such as ethylene glycol and the like can be mentioned; as the "residue of a compound having three active hydrogens", residues such as oligopeptide, lysine, aspartic acid, glutamic acid, glycerol and the like can be mentioned; as the "residue of a compound having four active hydrogens", residues such as pentaerythritol, diglycerol and the like can be mentioned; as the "residue of a compound having five active hydrogens", residues such as xylitol and the like can be mentioned. A residue of ethylene glycol, lysine, aspartic acid, glutamic acid, glycerol, pentaerythritol, diglycerol or xylitol, or a residue of oligopeptide is preferable, a residue of ethylene glycol, lysine, glutamic acid, glycerol, oligopeptide is more preferable, and a residue of ethylene glycol, lysine is particularly preferable.

In addition, the relationship between v, which is the number of active hydrogens of Q, and p, which shows the number of polyethylene glycol chains of the polyethylene glycol derivative moiety in the formula (1), is preferably v=p+1, v=2 when p=1, and Q is a residue of ethylene glycol and the like, and v=3 when p=2, Q is a residue of glycerol, lysine, aspartic acid, glutamic acid or the like, and v=4 when p=3, Q is a residue of pentaerythritol, diglycerol or the like, and v=5 when p=4, and Q is a residue of xylitol or the like.

When Q is a residue of oligopeptide, the oligopeptide is not particularly limited as long as it is an oligopeptide with 4-8 residues containing any one of lysine, aspartic acid and glutamic acid, and composed of neutral amino acids excluding cysteineit as the other amino acids which is stable in the blood of living organisms and has property of degradation by an enzyme in cells. Specific examples include glutamic acid-glycine-phenylalanine-leucine-glycine (SEQ ID NO: 6), glycine-glutamic acid-phenylalanine-leucine-glycine (SEQ ID NO: 7), glutamic acid-glycine-glycine-phenylalanine-glycine (SEQ ID NO: 8), glutamic acid-phenylalanine-glycine, glutamic acid-glycine-phenylalanine-glycine (SEQ ID NO: 9), glutamic acid-glycine-leucine-glycine (SEQ ID NO: 10), glutamic acid-valine-citrulline-glycine (SEQ ID NO: 11), glutamic acid-valine-alanine-glycine (SEQ ID NO: 12), glutamic acid-phenylalanine-glycine and the like. It is preferably glutamic acid-glycine-phenylalanine-leucine-glycine (SEQ ID NO: 6), glutamic acid-glycine-phenylalanine-glycine (SEQ ID NO: 9), glutamic acid-valine-citrulline-glycine (SEQ ID NO: 11), glutamic acid-valine-alanine-glycine (SEQ ID NO: 12), more preferably glutamic acid-glycine-phenylalanine-leucine-glycine (SEQ ID NO: 6), glutamic acid-valine-citrulline-glycine (SEQ ID NO: 11). The oligopeptide is preferably an oligopeptide having glycine as C-terminal amino acid. The oligopeptide is further preferably an oligopeptide having at least one hydrophobic neutral amino acid having a hydropathy index of not less than 2.5. For detailed explanation of the oligopeptide, refer to the above-mentioned explanation of the oligopeptide for Z.

In the formula (1), $L^1$, $L^2$, $L^3$, $L^4$ and $L^5$ are each independently a single bond or a divalent spacer. These spacers are not particularly limited as long as they are groups capable of forming a covalent bond. Preferably, they are each a single bond, a phenylene group, an amide bond, an ether bond, a thioether bond, a urethane bond, a secondary amino group, a carbonyl group, a urea bond, a triazine group, a bond of maleimide and thiol, an oxime bond, or an alkylene group optionally containing these bonds and groups, more preferably, a single bond, an amide bond, an ether bond, a thioether bond, a urethane bond, a secondary amino group, a carbonyl group, a triazine group, a bond of maleimide and thiol, an oxime bond, or a group formed by binding these bonds and groups and 1 to 3 alkylene groups, and particularly preferred embodiments are those shown in the following group (I). An ester bond and a carbonate bond are not suitable since they are gradually degraded in the blood of living organisms.

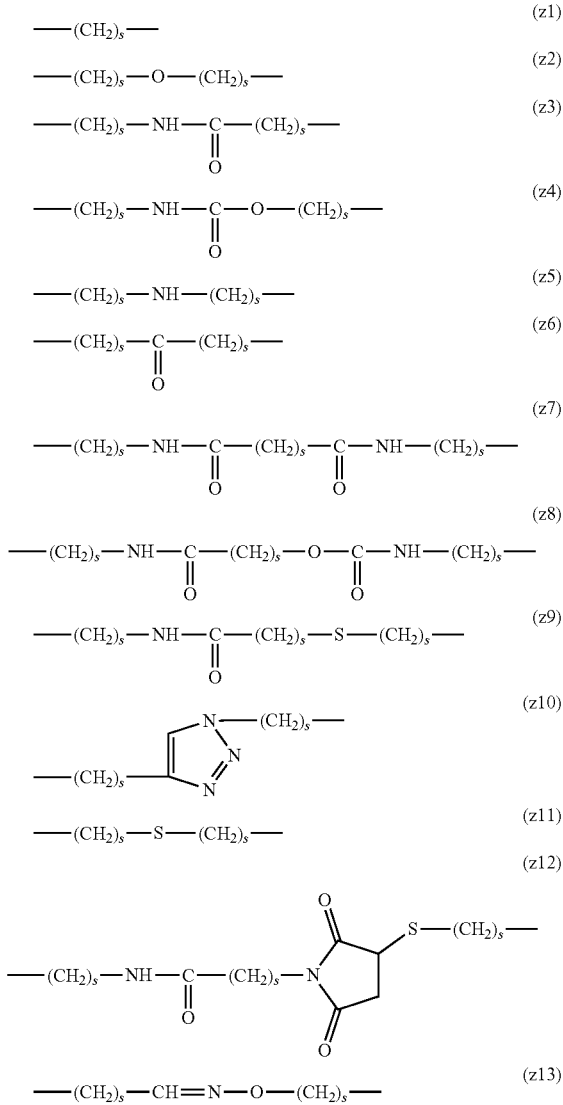

In the formulas (the formula (z1)-the formula (z13)), s is an integer of 0-10, preferably an integer of 0-6, further preferably an integer of 0-3. In the formula (z2)-the formula (z13), s in the number of 2-3 may be the same or different.

$L^1$, $L^2$, $L^3$ and $L^4$ in the formula (1) are preferably each independently (z1), (z2), (z3), (z4), (z5), (z6), (z7), (z8), or (z11), more preferably (z1), (z2), (z3), (z4), (z5), or (z6), in the above-mentioned group (I).

As $L^5$ in the formula (1), (z1), (z2), (z3), (z4), (z5), (z6), (z7), (z8), (z9), (z10), (z12), or (z13) in the above-mentioned group (I) is preferable, (z2), (z3), (z4), (z5), (z6), (z7), (z10), (z12), or (z13) is more preferable, and (z3), (z5), or (z12) is particularly preferable.

In one preferred embodiment of the present invention, $L^1$, $L^2$, $L^3$, $L^4$ and $L^5$ are each independently a single bond, a phenylene group, a urethane bond, amide bond, ether bond, a thioether bond, a secondary amino group, a carbonyl group, a urea bond, a triazine group, a bond of maleimide and thiol, an oxime bond, or an alkylene group optionally containing such bond or group.

In another preferred embodiment of the present invention, $L^1$, $L^2$, $L^3$, $L^4$ and $L^5$ are each independently a single bond, an amide bond, an ether bond, a secondary amino group, a carbonyl group, or an alkylene group optionally containing these bonds and groups (e.g., a single bond, —O—, —(CH$_2$)$_2$—, —(CH$_2$)$_3$—, —(CH$_2$)$_2$—O—, —(CH$_2$)$_3$—O—, —(CH$_2$)$_2$—CO—NH—, —(CH$_2$)$_2$—CO—NH—(CH$_2$)$_3$—, —CO—, —(CH$_2$)$_5$—CO—, —NH—), more preferably, $L^1$ is a single bond, an ether bond or an alkylene group optionally containing an ether bond (e.g., a single bond, —O—, —(CH$_2$)$_2$—O—), $L^2$ is a carbonyl group or an alkylene group optionally containing a carbonyl group (e.g., —CO—, —(CH$_2$)$_5$—CO—), $L^3$ is a secondary amino group (—NH—), $L^4$ is an alkylene group optionally containing an ether bond (e.g., —(CH$_2$)$_3$—O—), and $L^5$ is a single bond or an alkylene group optionally containing an amide bond (e.g., a single bond, —(CH$_2$)$_2$—, —(CH$_2$)$_3$—, —(CH$_2$)$_2$—CO—NH—, —(CH$_2$)$_2$—CO—NH—(CH$_2$)$_3$—).

In the formula (1), m is the number of repeating units in which a bond of polyethylene glycol chain and oligopeptide is one constitutional unit. It is preferably 1-7, more preferably 1-5, further preferably 1-3.

D in the formula (1) is a bio-related substance and is not particularly limited. It is a substance related to diagnosis, cure, alleviation, treatment or prophylaxis of diseases in human or other animals. Specifically, it includes proteins, peptides, nucleic acids, cells, viruses and the like, and suitable protein or peptide includes hormones, cytokines, antibodies, aptamers, enzymes and the like.

More specifically, cytokine includes interferon type I, type II, type III, interleukin, tumor necrosis factor, receptor antagonist thereof, and the like that regulate immunity. The growth factor includes erythropoietin, which is a hematopoietic factor, granulocyte colony-stimulating factor (GCSF), which is a stimulating factor, and the like. The blood coagulation factor includes factor V, factor VII, factor VIII, factor IX, factor X, factor XII and the like. The hormone includes calcitonin, insulin, analog thereof, exendin, GLP-1, somatostatin, human growth hormone, and the like. The antibody includes Fab and svFV as antibody fragments; the aptamer includes DNA aptamer, RNA aptamer and the like; and the enzyme so includes superoxide dismutase, uricase and the like. These proteins have low stability in blood and are desirably modified with polyethylene glycol to prolong their half-life in blood. The protein preferably includes interferon, interleukin, erythropoietin, GCSF, factor VIII, factor IX, calcitonin, insulin, exendin, human growth hormone, and antibody fragment, more preferably insulin, calcitonin, human growth hormone, interferon, GCSF, erythropoietin, and antibody fragment (particularly Fab), further preferably calcitonin (particularly salmon calcitonin), insulin, human growth hormone, and GCSF, particularly preferably calcitonin (particularly salmon calcitonin), human growth hormone, and GCSF.

The following formula (2) is a bio-related substance bonded to the polyethylene glycol derivative of the formula (1) wherein the oligopeptide for Z is an oligopeptide having glycine as the C-terminal amino acid, that is, a preferable embodiment of a bio-related substance bonded to the polyethylene glycol derivative wherein, in the formula (1), Z is composed of $Z^1$, A and a glycine residue.

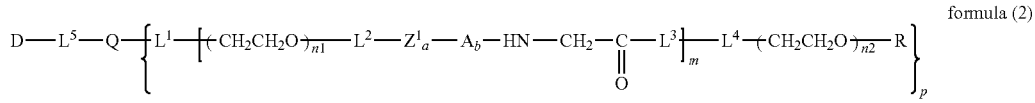
formula (2)

wherein $Z^1$ is an oligopeptide with 2-6 residues composed of neutral amino acids excluding cysteine, A is a neutral amino acid excluding cysteine, a and b are each independently 0 or 1, and (a+b)≥1, and m, n1 and n2, p, R, Q, D, $L^1$, $L^2$, $L^3$, $L^4$ and $L^5$ are as defined above.

The molecular weight per one molecule of the polyethylene glycol derivative bonded to bio-related substance D of the formula (2) of the present invention is generally 4,000-160,000, preferably 10,000-120,000, further preferably 30,000-80,000. In one preferred embodiment of the present invention, the molecular weight per one molecule of the polyethylene glycol derivative of the formula (2) of the present invention is not less than 30,000. The molecular weight here is a number average molecular weight (Mn).

In the formula (2), $Z^1$ is an oligopeptide with 2-6 residues composed of neutral amino acids excluding cysteine. An oligopeptide with 2-4 residues composed of neutral amino acids excluding cysteine is preferable, oligopeptide with 2-3 residues composed of neutral amino acids excluding cysteine is more preferable, and an oligopeptide having a hydrophobic neutral amino acid having a hydropathy index of not less than 2.5, specifically, at least one of phenylalanine, leucine, valine, and isoleucine is preferable, and an oligopeptide having phenylalanine is further preferable.

In the formula (2), $Z^1$ is an oligopeptide that is stable in the blood of living organisms, and has property of degradation by an enzyme in cells. Specific examples include glycine-phenylalanine-leucine, glycine-glycine-phenylalanine, glycine-phenylalanine, valine-citrulline, valine-alanine, and glycine-glycine. It is preferably glycine-phenylalanine-leucine, glycine-glycine-phenylalanine, glycine-phenylalanine, glycine-glycine, valine-citrulline, or valine-alanine, more preferably glycine-phenylalanine-leucine, glycine-phenylalanine, valine-citrulline, or valine-alanine, further more preferably glycine-phenylalanine-leucine, or valine-citrulline.

In the formula (2), A is a neutral amino acid excluding cysteine, preferably a hydrophobic neutral amino acid having a hydropathy index of not less than 2.5, specifically phenylalanine, leucine, valine, or isoleucine, more preferably phenylalanine, or leucine.

Preferred embodiments of m, n1 and n2, R, Q, D, $L^1$, $L^2$, $L^3$, $L^4$ and $L^5$ are as explained as regards the above-mentioned formula (1).

The following formula (3) shows a preferable embodiment of a bio-related substance bonded to a polyethylene glycol derivative wherein, in the formula (2), m=1:

wherein n3 and n4 are each independently 45-682, and p, R, $Z^1$, A, a, b, Q, D, $L^1$, $L^2$, $L^3$, $L^4$ and $L^5$ are as defined above.

The molecular weight per one molecule of the polyethylene glycol derivative bonded to bio-related substance D in the formula (3) of the present invention is generally 4,000-160,000, preferably 10,000-120,000, further preferably 30,000-80,000. In one preferred embodiment of the present invention, the molecular weight per one molecule of the polyethylene glycol derivative of the formula (3) of the present invention is not less than 30,000. The molecular weight here is a number average molecular weight (Mn).

In the formula (3), n3 and n4 are each a repeating unit number of polyethylene glycol. Generally, they are each independently 45-682, preferably 113-568.

Preferred embodiments of R, $Z^1$, A, Q, D, $L^1$, $L^2$, $L^3$, $L^4$ and $L^5$ are as explained as regards the above-mentioned formulas (1) and (2).

[Bio-Related Substance Bonded to Straight Chain Polyethylene Glycol Derivative of the Formula (1)]

The following formula (4) shows a preferable embodiment of a bio-related substance bonded to a straight chain polyethylene glycol derivative, wherein, in the formula (1), Q is a residue of ethylene glycol, $L^1$ is $CH_2CH_2O$, and p is 1.

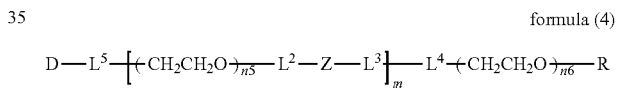
formula (4)

wherein n5 and n6 are each independently 113-682, and m, R, Z, D, $L^2$, $L^3$, $L^4$ and $L^5$ are as defined above.

The molecular weight per one molecule of the polyethylene glycol derivative bonded to bio-related substance D in the formula (4) of the present invention is generally 20,000-120,000, preferably 25,000-80,000, further preferably 30,000-60,000. In one preferred embodiment of the present invention, the molecular weight per one molecule of the polyethylene glycol derivative of the formula (1) of the present invention is not less than 30,000. The molecular weight here is a number average molecular weight (Mn).

In the formula (4), n5 and n6 are each a repeating unit number of polyethylene glycol. Generally, they are each independently 113-682, preferably 180-525. n5 and n6 may be different or the same.

Preferred embodiments of m, R, Z, D, $L^2$, $L^3$, $L^4$ and $L^5$ are as explained as regards the above-mentioned formula (1).

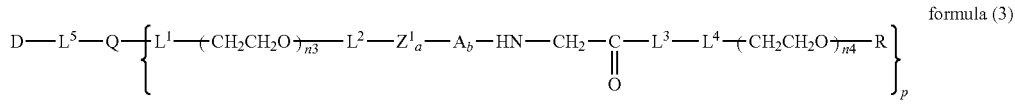
formula (3)

The following formula (5) shows a preferable embodiment of a bio-related substance bonded to a straight chain polyethylene glycol derivative, wherein, in the formula (2), Q is a residue of ethylene glycol, $L^1$ is $CH_2CH_2O$, and p is 1.

3-5 active hydrogens is a preferable embodiment of a bio-related substances bonded to a branched type polyethylene glycol derivative.

The residue of a compound having 3-5 active hydrogens for Q is preferably a residue of lysine, aspartic acid, glutamic

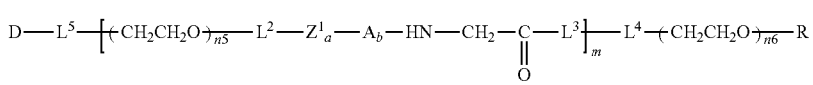

formula (5)

wherein n5 and n6 are each independently 113-682, and m, R, $Z^1$, A, a, b, D, $L^2$, $L^3$, $L^4$ and $L^5$ are as defined above.

In the formula (5), n5 and n6 are each a repeating unit number of polyethylene glycol. Generally, they are each independently 113-682, preferably each independently 180-525. n5 and n6 may be different or the same.

The molecular weight per one molecule of the polyethylene glycol derivative bonded to bio-related substance D in the formula (5) of the present invention is generally 20,000-60,000, preferably 25,000-55,000, further preferably 30,000-50,000. In one preferred embodiment of the present invention, the molecular weight per one molecule of the polyethylene glycol derivative of the formula (5) of the present invention is not less than 30,000. The molecular weight here is a number average molecular weight (Mn).

Preferred embodiments of m, R, $Z^1$, A, D, $L^2$, $L^3$, $L^4$ and $L^5$ are as explained as regards the above-mentioned formulas (1) and (2).

The following formula (6) shows a preferable embodiment of a bio-related substance bonded to a straight chain polyethylene glycol derivative, wherein, in the formula (3), Q is a residue of ethylene glycol, $L^1$ is $CH_2CH_2O$, and p is 1.

acid, glycerol, pentaerythritol, diglycerol or xylitol, or a residue of oligopeptide, particularly preferably a residue of lysine or glutamic acid. Preferred embodiments of the oligopeptide are as explained as regards the above-mentioned formula (1).

Preferred embodiments of m, R, Z, D, $L^1$, $L^2$, $L^3$, $L^4$ and $L^5$ are as explained as regards the above-mentioned formula (1).

Among the bio-related substances bonded to the polyethylene glycol derivatives of the formula (2), a bio-related substances bonded to a polyethylene glycol derivative wherein p is 2-4, and Q is a residue of a compound having 3-5 active hydrogens is a preferable embodiment of a bio-related substances bonded to a branched type polyethylene glycol derivative.

The residue of a compound having 3-5 active hydrogens for Q is preferably a residue of lysine, aspartic acid, glutamic acid, glycerol, pentaerythritol, diglycerol or xylitol, or a residue of oligopeptide, particularly preferably a residue of lysine or glutamic acid. Preferred embodiments of the oligopeptide are as explained as regards the above-mentioned formula (1).

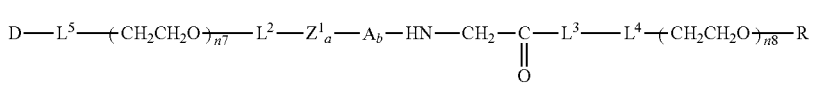

formula (6)

wherein n7 and n8 are each independently 226-682, and R, $Z^1$, A, a, b, D, $L^2$, $L^3$, $L^4$ and $L^5$ are as defined above.

The molecular weight per one molecule of the polyethylene glycol derivative bonded to bio-related substance D in the formula (6) of the present invention is generally 20,000-60,000, preferably 25,000-55,000, further preferably 30,000-50,000. In one preferred embodiment of the present invention, the molecular weight per one molecule of the polyethylene glycol derivative of the formula (3) of the present invention is not less than 30,000. The molecular weight here is a number average molecular weight (Mn).

In the formula (6), n7 and n8 are each a repeating unit number of polyethylene glycol. Generally, they are each independently 226-682, preferably each independently 340-568. n7 and n8 may be different or the same.

Preferred embodiments of R, $Z^1$, A, D, $L^2$, $L^3$, $L^4$ and $L^5$ are as explained as regards the above-mentioned formulas (1) and (2).

[Bio-Related Substance Bonded to Branched Type Polyethylene Glycol Derivative of the Formula (1)]

Among the bio-related substances bonded to the polyethylene glycol derivatives of the formula (1), a bio-related substances bonded to a polyethylene glycol derivative wherein p is 2-4, and Q is a residue of a compound having Preferred embodiments of m, R, $Z^1$, A, D, $L^1$, $L^2$, $L^3$, $L^4$ and $L^5$ are as explained as regards the above-mentioned formulas (1) and (2).

Among the bio-related substances bonded to the polyethylene glycol derivatives of the formula (3), a bio-related substances bonded to a polyethylene glycol derivative wherein n3 and n4 are each independently 113-682, p is 2-4, and Q is a residue of a compound having 3-5 active hydrogens is a preferable embodiment of a bio-related substances bonded to a branched type polyethylene glycol derivative.

n3 and n4 are each a repeating unit number of polyethylene glycol. Preferably, they are each independently 226-455. n3 and n4 may be different or the same.

The residue of a compound having 3-5 active hydrogens for Q is preferably a residue of lysine, aspartic acid, glutamic acid, glycerol, pentaerythritol, diglycerol or xylitol, or a residue of oligopeptide, particularly preferably a residue of lysine or glutamic acid. Preferred embodiments of the oligopeptide are as explained as regards the above-mentioned formula (1).

Preferred embodiments of R, $Z^1$, A, D, $L^1$, $L^2$, $L^3$, $L^4$ and $L^5$ are as explained as regards the above-mentioned formulas (1) and (2).

Preferable examples of the bio-related substance bonded to the polyethylene glycol derivative of the formula (1) of the present invention include the following polyethylene glycol derivatives.

[Bio-Related Substance Bonded to Polyethylene Glycol Derivative (1-1)]

A bio-related substance bonded to a polyethylene glycol derivative of the formula (1), wherein m is 1-3;
n1 and n2 are each independently 113-568;
p is 1 or 2;
R is an alkyl group having 1-3 carbon atoms (e.g., a methyl group);
Z is an oligopeptide with 2-4 residues composed of neutral amino acids excluding cysteine (e.g., glycine-phenylalanine-leucine-glycine (SEQ ID NO: 4), glycine-glycine-phenylalanine-glycine (SEQ ID NO: 5), glycine-phenylalanine-glycine, glycine-glycine-glycine, valine-citrulline-glycine, valine-alanine-glycine, phenylalanine-glycine);
Q is a residue of ethylene glycol or a residue of lysine;
D is a calcitonin, a human growth hormone or a granulocyte colony stimulating factor;
$L^1$, $L^2$, $L^3$, $L^4$ and $L^5$ are each independently a single bond, an amide bond, an ether bond, a secondary amino group, a carbonyl group, or an alkylene group optionally comprising such bond or group [preferably, each independently a spacer selected from

wherein s is an integer of 0-6, and s in the number of 2 in (z2), (z3), (z5) and (z6) may be the same or different](e.g., a single bond, —O—, —(CH$_2$)$_2$—, —(CH$_2$)$_3$—, —(CH$_2$)$_2$—O—, —(CH$_2$)$_3$—O—, —(CH$_2$)$_2$—CO—NH—, —(CH$_2$)$_2$—CO—NH—(CH$_2$)$_3$—, —CO—, —(CH$_2$)$_5$—CO—, —NH—).

[Bio-Related Substance Bonded to Polyethylene Glycol Derivative (1-2)]

A bio-related substance bonded to a polyethylene glycol derivative of the formula (1), wherein m is 1-3;
n1 and n2 are each independently 113-568;
p is 1 or 2;
R is an alkyl group having 1-3 carbon atoms (e.g., a methyl group);
Z is an oligopeptide with 2-4 residues composed of neutral amino acids excluding cysteine (e.g., glycine-phenylalanine-leucine-glycine (SEQ ID NO: 4), glycine-glycine-phenylalanine-glycine (SEQ ID NO: 5), glycine-phenylalanine-glycine, glycine-glycine-glycine, valine-citrulline-glycine, valine-alanine-glycine, phenylalanine-glycine);
Q is a residue of ethylene glycol or a residue of lysine;
D is a calcitonin, a human growth hormone or a granulocyte colony stimulating factor;
$L^1$ is a single bond, an ether bond or an alkylene group optionally containing an ether bond [preferably,

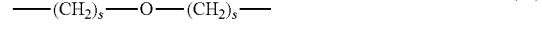

wherein s is an integer of 0-6, s in the number of 2 in (z2) may be the same or different](e.g., a single bond, —O—, —(CH$_2$)$_2$—O—);
$L^2$ is a carbonyl group or an alkylene group optionally containing a carbonyl group [preferably,

wherein s in the number of 2 may be the same or different and are each an integer of 0-6](e.g., —CO—, —(CH$_2$)$_5$—CO—);
$L^3$ is a secondary amino group (—NH—);
$L^4$ is an alkylene group optionally containing an ether bond [preferably,

wherein s in the number of 2 may be the same or different and are each an integer of 0-6](e.g., —(CH$_2$)$_3$—O—);
$L^5$ is a single bond or an alkylene group optionally containing an amide bond [preferably,

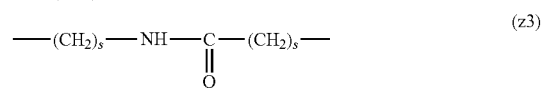

wherein s is an integer of 0-6, and s in the number of 2 in (z3) may be the same or different](e.g., a single bond, —(CH$_2$)$_2$—, —(CH$_2$)$_3$—, —(CH$_2$)$_2$—CO—NH—, —(CH$_2$)$_2$—CO—NH—(CH$_2$)$_3$—).

Preferable examples of the bio-related substance bonded to the polyethylene glycol derivative of the formula (2) of the present invention include the following bio-related substances bonded to polyethylene glycol derivatives.

[Bio-Related Substance Bonded to Polyethylene Glycol Derivative (2-1)]

A bio-related substance bonded to a polyethylene glycol derivative of the formula (2), wherein m is 1-3;
p is 1 or 2;
n1 and n2 are each independently 113-568;
R is an alkyl group having 1-3 carbon atoms (e.g., a methyl group);
$Z^1$ is an oligopeptide with 2-3 residues composed of neutral amino acids excluding cysteine (e.g., glycinephenylalanine-leucine, glycine-glycine-phenylalanine, glycine-phenylalanine, glycine-glycine, valine-citrulline, valine-alanine);

A is phenylalanine or leucine;

a and b are each independently 0 or 1, and (a+b)≥1;

Q is a residue of ethylene glycol or a residue of lysine;

D is a calcitonin, a human growth hormone or a granulocyte colony stimulating factor;

$L^1$, $L^2$, $L^3$, $L^4$ and $L^5$ are each independently a single bond, an amide bond, an ether bond, a secondary amino group, a carbonyl group, or an alkylene group optionally comprising such bond or group [preferably, each independently a spacer selected from

 (z1)

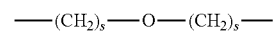 (z2)

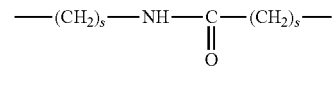 (z3)

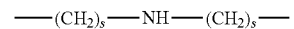 (z5)

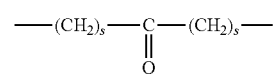 (z6)

wherein s is an integer of 0-6, s in the number of 2 in (z2), (z3), (z5) and (z6) may be the same or different](e.g., a single bond, —O—, —(CH$_2$)$_2$—, —(CH$_2$)$_3$—, —(CH$_2$)$_2$—O—, —(CH$_2$)$_3$—O—, —(CH$_2$)$_2$—CO—NH—, —(CH$_2$)$_2$—CO—NH—(CH$_2$)$_3$—, —CO—, —(CH$_2$)$_5$—CO—, —NH—).

[Bio-Related Substance Bonded to Polyethylene Glycol Derivative (2-2)]

A bio-related substance bonded to a polyethylene glycol derivative of the formula (2), wherein m is 1-3;

p is 1 or 2;

n1 and n2 are each independently 113-568;

R is an alkyl group having 1-3 carbon atoms (e.g., a methyl group);

$Z^1$ is an oligopeptide with 2-3 residues composed of neutral amino acids excluding cysteine (e.g., glycine-phenylalanine-leucine, glycine-glycine-phenylalanine, glycine-phenylalanine, glycine-glycine, valine-citrulline, valine-alanine);

A is phenylalanine or leucine;

a and b are each independently 0 or 1, and (a+b)≥1;

Q is a residue of ethylene glycol or a residue of lysine;

D is a calcitonin, a human growth hormone or a granulocyte colony stimulating factor;

$L^1$ is a single bond, an ether bond or an alkylene group optionally containing an ether bond [preferably,

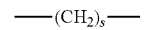 (z1)

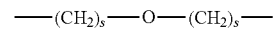 (z2)

wherein s is an integer of 0-6, s in the number of 2 in (z2) may be the same or different](e.g., a single bond, —O—, —(CH$_2$)$_2$—O—);

$L^2$ is a carbonyl group or an alkylene group optionally containing a carbonyl group [preferably,

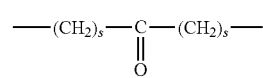 (z6)

wherein s in the number of 2 may be the same or different and are each an integer of 0-6](e.g., —CO—, —(CH$_2$)$_5$—CO—);

$L^3$ is a secondary amino group (—NH—);

$L^4$ is an alkylene group optionally containing an ether bond [preferably,

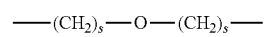 (z2)

wherein s in the number of 2 may be the same or different and are each an integer of 0-6](e.g., —(CH$_2$)$_3$—O—);

$L^5$ is a single bond or an alkylene group optionally containing an amide bond [preferably,

 (z1)

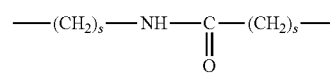 (z3)

wherein s is an integer of 0-6, and s in the number of 2 in (z3) may be the same or different](e.g., a single bond, —(CH$_2$)$_2$—, —(CH$_2$)$_3$—, —(CH$_2$)$_2$—CO—NH—, —(CH$_2$)$_2$—CO—NH—(CH$_2$)$_3$—).

Preferable examples of the bio-related substance bonded to the polyethylene glycol derivative of the formula (3) of the present invention include the following bio-related substances bonded to polyethylene glycol derivatives.

[Bio-Related Substance Bonded to Polyethylene Glycol Derivative (3-1)]

A bio-related substance bonded to a polyethylene glycol derivative of the formula (3), wherein p is 1 or 2;

n3 and n4 are each independently 340-568;

R is an alkyl group having 1-3 carbon atoms (e.g., a methyl group);

$Z^1$ is an oligopeptide with 2-3 residues composed of neutral amino acids excluding cysteine (e.g., glycine-phenylalanine-leucine, glycine-glycine-phenylalanine, glycine-phenylalanine, glycine-glycine, valine-citrulline, valine-alanine);

A is phenylalanine or leucine;

a and b are each independently 0 or 1, and (a+b)≥1;

Q is a residue of ethylene glycol or a residue of lysine;

D is a calcitonin, a human growth hormone or a granulocyte colony stimulating factor;

$L^1$, $L^2$, $L^3$, $L^4$ and $L^5$ are each independently a single bond, an amide bond, an ether bond, a secondary amino group, a carbonyl group, or an alkylene group optionally comprising such bond or group [preferably, each independently a spacer selected from

 (z1)

-continued

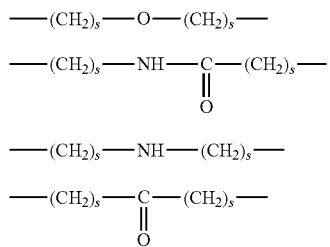

wherein s is an integer of 0-6, and s in the number of 2 in (z2), (z3), (z5) and (z6) may be the same or different](e.g., a single bond, —O—, —(CH$_2$)$_2$—, —(CH$_2$)$_3$—, —(CH$_2$)$_2$—O—, —(CH$_2$)$_3$—O—, —(CH$_2$)$_2$—CO—NH—, —(CH$_2$)$_2$—CO—NH—(CH$_2$)$_3$—, —CO—, —(CH$_2$)$_5$—CO—, —NH—).

[Bio-Related Substance Bonded to Polyethylene Glycol Derivative (3-2)]

A bio-related substance bonded to a polyethylene glycol derivative of the formula (3), wherein p is 1 or 2;

n3 and n4 are each independently 340-568;

R is an alkyl group having 1-3 carbon atoms (e.g., a methyl group);

$Z^1$ is an oligopeptide with 2-3 residues composed of neutral amino acids excluding cysteine (e.g., glycine-phenylalanine-leucine, glycine-glycine-phenylalanine, glycine-phenylalanine, glycine-glycine, valine-citrulline, valine-alanine);

A is phenylalanine or leucine;

a and b are each independently 0 or 1, and (a+b)≥1;

Q is a residue of ethylene glycol or a residue of lysine;

D is a calcitonin, a human growth hormone or a granulocyte colony stimulating factor;

$L^1$ is a single bond, an ether bond or an alkylene group optionally containing an ether bond [preferably,

wherein s is an integer of 0-6, and s in the number of 2 in (z2) may be the same or different](e.g., a single bond, —O—, —(CH$_2$)$_2$—O—);

$L^2$ is a carbonyl group or an alkylene group optionally containing a carbonyl group [preferably,

wherein s in the number of 2 may be the same or different and are each an integer of 0-6](e.g., —CO—, —(CH$_2$)$_5$—CO—);

$L^3$ is a secondary amino group (—NH—);

$L^4$ is an alkylene group optionally containing an ether bond [preferably,

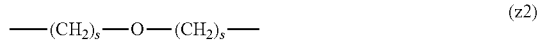

wherein s in the number of 2 may be the same or different and are each an integer of 0-6](e.g., —(CH$_2$)$_3$—O—);

$L^5$ is a single bond or an alkylene group optionally containing an amide bond [preferably,

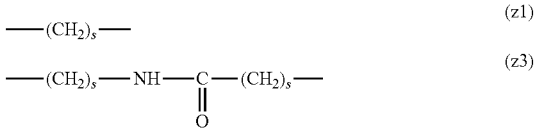

wherein s is an integer of 0-6, and s in the number of 2 in (z3) may be the same or different](e.g., a single bond, —(CH$_2$)$_2$—, —(CH$_2$)$_3$—, —(CH$_2$)$_2$—CO—NH—, —(CH$_2$)$_2$—CO—NH—(CH$_2$)$_3$—).

Preferable examples of the bio-related substance bonded to the polyethylene glycol derivative of the formula (4) of the present invention include the following bio-related substances bonded to polyethylene glycol derivatives.

[Bio-Related Substance Bonded to Polyethylene Glycol Derivative (4-1)]

A bio-related substance bonded to a polyethylene glycol derivative of the formula (4), wherein m is 1-3;

n5 and n6 are each independently 180-525;

R is an alkyl group having 1-3 carbon atoms (e.g., a methyl group);

Z is an oligopeptide with 2-4 residues composed of neutral amino acids excluding cysteine (e.g., glycine-phenylalanine-leucine-glycine (SEQ ID NO: 4), glycine-glycine-phenylalanine-glycine (SEQ ID NO: 5), glycine-phenylalanine-glycine, glycine-glycine-glycine, valine-citrulline-glycine, valine-alanine-glycine, phenylalanine-glycine);

D is a calcitonin, a human growth hormone or a granulocyte colony stimulating factor;

$L^2$, $L^3$, $L^4$ and $L^5$ are each independently a single bond, an amide bond, an ether bond, a secondary amino group, a carbonyl group, or an alkylene group optionally comprising such bond or group [preferably, each independently a spacer selected from

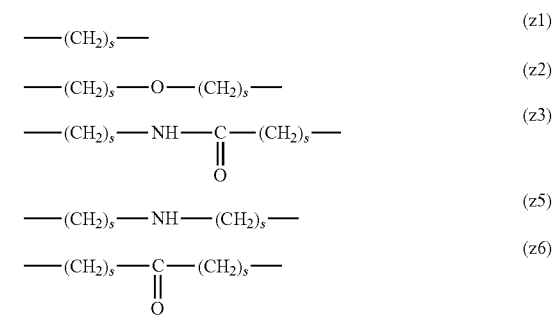

wherein s is an integer of 0-6, and s in the number of 2 in (z2), (z3), (z5) and (z6) may be the same or different](e.g., a single bond, —O—, —(CH$_2$)$_2$—, —(CH$_2$)$_3$—, —(CH$_2$)$_2$—O—, —(CH$_2$)$_3$—O—, —(CH$_2$)$_2$—CO—NH—, —(CH$_2$)$_2$—CO—NH—(CH$_2$)$_3$—, —CO—, —(CH$_2$)$_5$—CO—, —NH—).

[Bio-Related Substance Bonded to Polyethylene Glycol Derivative (4-2)]

A bio-related substance bonded to a polyethylene glycol derivative of the formula (4), wherein m is 1-3;

n5 and n6 are each independently 180-525;

R is an alkyl group having 1-3 carbon atoms (e.g., a methyl group);

Z is an oligopeptide with 2-4 residues composed of neutral amino acids excluding cysteine (e.g., glycine-phenylalanine-leucine-glycine (SEQ ID NO: 4), glycine-glycine-phenylalanine-glycine (SEQ ID NO: 5), glycine-phenylalanine-glycine, glycine-glycine-glycine, valine-citrulline-glycine, valine-alanine-glycine, phenylalanine-glycine);

D is a calcitonin, a human growth hormone or a granulocyte colony stimulating factor;

$L^2$ is a carbonyl group or an alkylene group optionally containing a carbonyl group [preferably,

(z6)

wherein s in the number of 2 may be the same or different and are each an integer of 0-6](e.g., —CO—, —(CH$_2$)$_5$—CO—);

$L^3$ is a secondary amino group (—NH—);

$L^4$ is an alkylene group optionally containing an ether bond [preferably,

(z2)

wherein s in the number of 2 may be the same or different and are each an integer of 0-6](e.g., —(CH$_2$)$_3$—O—);

$L^5$ is a single bond or an alkylene group optionally containing an amide bond [preferably,

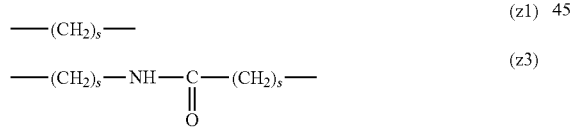

(z1)

(z3)

wherein s is an integer of 0-6, and s in the number of 2 in (z3) may be the same or different](e.g., a single bond, —(CH$_2$)$_2$—, —(CH$_2$)$_3$—, —(CH$_2$)$_2$—CO—NH—, —(CH$_2$)$_2$—CO—NH—(CH$_2$)$_3$—).

Preferable examples of the bio-related substance bonded to the polyethylene glycol derivative of the formula (5) of the present invention include the following bio-related substances bonded to polyethylene glycol derivatives.

[Bio-Related Substance Bonded to Polyethylene Glycol Derivative (5-1)]

A bio-related substance bonded to a polyethylene glycol derivative of the formula (5), wherein m is 1-3;

n5 and n6 are each independently 180-525;

R is an alkyl group having 1-3 carbon atoms (e.g., a methyl group);

$Z^1$ is an oligopeptide with 2-3 residues composed of neutral amino acids excluding cysteine (e.g., glycine-phenylalanine-leucine, glycine-glycine-phenylalanine, glycine-phenylalanine, glycine-glycine, valine-citrulline, valine-alanine);

A is phenylalanine or leucine;

a and b are each independently 0 or 1, and (a+b)≥1;

D is a calcitonin, a human growth hormone or a granulocyte colony stimulating factor;

$L^2$, $L^3$, $L^4$ and $L^5$ are each independently a single bond, an amide bond, an ether bond, a secondary amino group, a carbonyl group, or an alkylene group optionally comprising such bond or group [preferably, each independently a spacer selected from

(z1)

(z2)

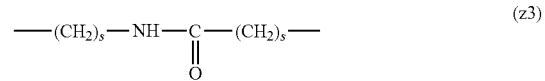

(z3)

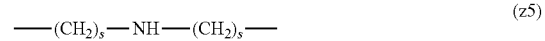

(z5)

(z6)

wherein s is an integer of 0-6, and s in the number of 2 in (z2), (z3), (z5) and (z6) may be the same or different](e.g., a single bond, —O—, —(CH$_2$)$_2$—, —(CH$_2$)$_3$—, —(CH$_2$)$_2$—O—, —(CH$_2$)$_3$—O—, —(CH$_2$)$_2$—CO—NH—, —(CH$_2$)$_2$—CO—NH—(CH$_2$)$_3$—, —CO—, —(CH$_2$)$_5$—CO—, —NH—).

[Bio-Related Substance Bonded to Polyethylene Glycol Derivative (5-2)]

A bio-related substance bonded to a polyethylene glycol derivative of the formula (5), wherein m is 1-3;

n5 and n6 are each independently 180-525;

R is an alkyl group having 1-3 carbon atoms (e.g., a methyl group);

$Z^1$ is an oligopeptide with 2-3 residues composed of neutral amino acids excluding cysteine (e.g., glycine-phenylalanine-leucine, glycine-glycine-phenylalanine, glycine-phenylalanine, glycine-glycine, valine-citrulline, valine-alanine);

A is phenylalanine or leucine;

a and b are each independently 0 or 1, and (a+b)≥1;

D is a calcitonin, a human growth hormone or a granulocyte colony stimulating factor;

$L^2$ is a carbonyl group or an alkylene group optionally containing a carbonyl group [preferably,

(z6)

wherein s in the number of 2 may be the same or different and are each an integer of 0-6](e.g., —CO—, —(CH$_2$)$_5$—CO—);

$L^3$ is a secondary amino group (—NH—);

L⁴ is an alkylene group optionally containing an ether bond [preferably,

—(CH₂)ₛ—O—(CH₂)ₛ— (z2)

wherein s in the number of 2 may be the same or different and are each an integer of 0-6](e.g., —(CH₂)₃—O—);

L⁵ is a single bond or an alkylene group optionally containing an amide bond [preferably, —(CH₂)ₛ— (z1)

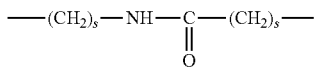 (z3)

wherein s is an integer of 0-6, and s in the number of 2 in (z3) may be the same or different](e.g., a single bond, —(CH₂)₂—, —(CH₂)₃—, —(CH₂)₂—CO—NH—, —(CH₂)₂—CO—NH—(CH₂)₃—).

Preferable examples of the bio-related substance bonded to the polyethylene glycol derivative of the formula (6) of the present invention include the following bio-related substances bonded to polyethylene glycol derivatives.

[Bio-Related Substance Bonded to Polyethylene Glycol Derivative (6-1)]

A bio-related substance bonded to a polyethylene glycol derivative of the formula (6), wherein n7 and n8 are each independently 340-568;

R is an alkyl group having 1-3 carbon atoms (e.g., a methyl group);

Z¹ is an oligopeptide with 2-3 residues composed of neutral amino acids excluding cysteine (e.g., glycine-phenylalanine-leucine, glycine-glycine-phenylalanine, glycine-phenylalanine, glycine-glycine, valine-citrulline, valine-alanine);

A is phenylalanine or leucine;

a and b are each independently 0 or 1, and (a+b)≥1;

D is a calcitonin, a human growth hormone or a granulocyte colony stimulating factor;

L², L³, L⁴ and L⁵ are each independently a single bond, an amide bond, an ether bond, a secondary amino group, a carbonyl group, or an alkylene group optionally comprising such bond or group [preferably, each independently a spacer selected from —(CH₂)ₛ— (z1)

—(CH₂)ₛ—O—(CH₂)ₛ— (z2)

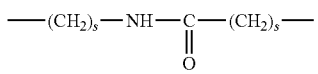 (z3)

—(CH₂)ₛ—NH—(CH₂)ₛ— (z5)

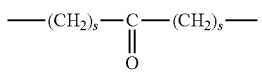 (z6)

wherein s is an integer of 0-6, and s in the number of 2 in (z2), (z3), (z5) and (z6) may be the same or different](e.g., a single bond, —O—, —(CH₂)₂—, —(CH₂)₃—, —(CH₂)₂—O—, —(CH₂)₃—O—, —(CH₂)₂—CO—NH—, —(CH₂)₂—CO—NH—(CH₂)₃—, —CO—, —(CH₂)₅—CO—, —NH—).

[Bio-Related Substance Bonded to Polyethylene Glycol Derivative (6-2)]

A bio-related substance bonded to a polyethylene glycol derivative of the formula (6), wherein n7 and n8 are each independently 340-568;

R is an alkyl group having 1-3 carbon atoms (e.g., a methyl group);

Z¹ is an oligopeptide with 2-3 residues composed of neutral amino acids excluding cysteine (e.g., glycine-phenylalanine-leucine, glycine-glycine-phenylalanine, glycine-phenylalanine, glycine-glycine, valine-citrulline, valine-alanine);

A is phenylalanine or leucine;

a and b are each independently 0 or 1, and (a+b)≥1;

D is a calcitonin, a human growth hormone or a granulocyte colony stimulating factor;

L² is a carbonyl group or an alkylene group optionally containing a carbonyl group [preferably,

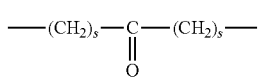 (z6)

wherein s in the number of 2 may be the same or different and are each an integer of 0-6](e.g., —CO—, —(CH₂)₅—CO—);

L³ is a secondary amino group (—NH—);

L⁴ is an alkylene group optionally containing an ether bond [preferably,

—(CH₂)ₛ—O—(CH₂)ₛ— (z2)

wherein s in the number of 2 may be the same or different and are each an integer of 0-6](e.g., —(CH₂)₃—O—);

L⁵ is a single bond or an alkylene group optionally containing an amide bond [preferably, —(CH₂)ₛ— (z1)

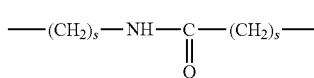 (z3)

wherein s is an integer of 0-6, and s in the number of 2 in (z3) may be the same or different](e.g., a single bond, —(CH₂)₂—, —(CH₂)₃—, —(CH₂)₂—CO—NH—, —(CH₂)₂—CO—NH—(CH₂)₃—).

The bio-related substance bonded to a polyethylene glycol derivative of the formula (1) of the present invention can be obtained by reacting a degradable polyethylene glycol derivative represented by the following formula (7) and a bio-related substance.

formula (7)

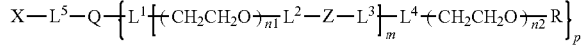

wherein X is a functional group capable of reacting with a bio-related substance, and m, n1 and n2, p, R, Z, Q, L¹, L², L³, L⁴ and L⁵ are as defined above.

In the formula (7), X is not particularly limited as long as it is a functional group that reacts with a functional group present in bio-related substances such as a physiologically active protein, peptide, antibody, or nucleic acid to be chemically modified to form a covalent bond. For example, the functional groups described in "Harris, J. M. Poly (Ethylene Glycol) Chemistry; Plenum Press: New York, 1992", "Hermanson, G. T. Bioconjugate Techniques, 2nd ed.; Academic Press: San Diego, CA, 2008" and "PEGylated Protein Drugs: Basic Science and Clinical Applications; Veronese, F. M., Ed.; Birkhauser: Basel, Switzerland, 2009" and the like can be mentioned.

In the formula (7), the "functional group capable of reacting with a bio-related substance" for X is not particularly limited as long as it is a functional group that can be chemically bonded to a functional group of a bio-related substance such as amino group, mercapto group, aldehyde group, carboxyl group, unsaturated bond or azide group and the like. Specifically, for example, it is active ester group, active carbonate group, aldehyde group, isocyanate group, isothiocyanate group, epoxide group, carboxyl group, thiol group, maleimide group, substituted maleimide group, hydrazide group, dithiopyridyl group, substituted sulfonate group, vinylsulfone group, amino group, oxyamino group, iodoacetamide group, alkylcarbonyl group, alkenyl group, alkynyl group, azide group, acrylic group, sulfonyloxy group, α-haloacetyl group, allyl group, vinyl group and the like, preferably, active ester group, active carbonate group, aldehyde group, isocyanate group, isothiocyanate group, epoxide group, maleimide group, vinylsulfone group, acrylic group, sulfonyloxy group, carboxyl group, thiol group, dithiopyridyl group, α-haloacetyl group, alkynyl group, allyl group, vinyl group, amino group, oxyamino group, hydrazide group and azide group, more preferably active ester group, active carbonate group, aldehyde group, maleimide group and amino group, particularly preferably aldehyde group, maleimide group and amino group.

In a preferred embodiment, the functional group X can be classified into the following group (II), group (III), group (IV), group (V), group (VI) and group (VII).

group (II): functional group capable of reacting with amino group of bio-related substance
(a), (b), (c), (d), (e), (f), (g), (j), (k) below
group (III): functional group capable of reacting with mercapto group of bio-related substance
(a), (b), (c), (d), (e), (f), (g), (h), (i), (j), (k), (l) below
group (IV): functional group capable of reacting with aldehyde of bio-related substance
(h), (m), (n), (p) below
group (V): functional group capable of reacting with carboxyl group of bio-related substance
(h), (m), (n), (p) below
group (VI): functional group capable of reacting with unsaturated bond of bio-related substance
(h), (m), (o) below
group (VII): functional group capable of reacting with azide group of bio-related substance
the following (l)

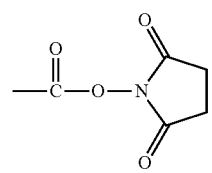
(a)

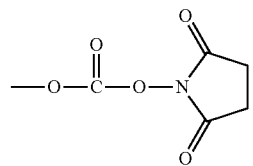
(b)

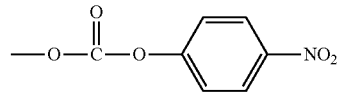
(c)

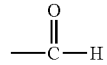
(d)

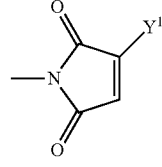
(e)

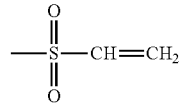
(f)

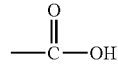
(g)

—SH (h)

(i)

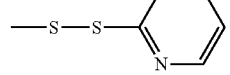
(j)

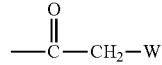
(k)

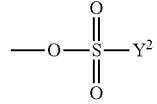
(l)

—NH$_2$ (m)

—ONH$_2$ (n)

—N$_3$ (o)

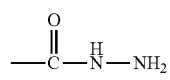
(p)

In functional group (j), W is a halogen atom such as a chlorine atom (Cl), a bromine atom (Br) or an iodine atom (I), preferably Br, I, more preferably I.

In functional group (e) and functional group (l), $Y^1$ and $Y^3$ are each independently a hydrogen atom or a hydrocarbon group having 1 to 5 carbon atoms, preferably a hydrocarbon group having 1 to 5 carbon atoms. Specific examples of the hydrocarbon group having 1 to 5 carbon atoms include a methyl group, an ethyl group, a propyl group, an isopropyl group, a butyl group, a tertiary butyl group and the like, preferably a methyl group or an ethyl group.

In functional group (k), $Y^2$ is a hydrocarbon group having 1-10 carbon atoms and optionally containing a fluorine atom. Specifically, it is a methyl group, an ethyl group, a propyl group, an isopropyl group, a butyl group, a tertiary butyl group, a hexyl group, a nonyl group, a vinyl group, a phenyl group, a benzyl group, a 4-methylphenyl group, a trifluoromethyl group, a 2,2,2-trifluoroethyl group, a 4-(trifluoromethoxy)phenyl group or the like, preferably a methyl group, a vinyl group, a 4-methylphenyl group, or a 2,2,2-trifluoroethyl group.

The active ester group is an ester group having an alkoxy group with high elimination ability. As the alkoxy group with high elimination ability, an alkoxy group induced from nitrophenol, N-hydroxysuccinimide, pentafluorophenol and the like can be mentioned. The active ester group is preferably an ester group having an alkoxy group induced from N-hydroxysuccinimide.

The active carbonate group is a carbonate group having an alkoxy group with high elimination ability. As the alkoxy group with high elimination ability, an alkoxy group induced from nitrophenol, N-hydroxysuccinimide, pentafluorophenol and the like can be mentioned. The active carbonate group is preferably a carbonate group having an alkoxy group induced from nitrophenol or N-hydroxysuccinimide.

The substituted maleimide group is a maleimide group in which a hydrocarbon group is bonded to one carbon atom of the double bond of the maleimide group. The hydrocarbon group is specifically a methyl group, an ethyl group, a propyl group, an isopropyl group, a butyl group, a tertiary butyl group and the like, preferably a methyl group or an ethyl group.

The substituted sulfonate group is a sulfonate group in which a hydrocarbon group which may contain a fluorine atom is bonded to a sulfur atom of the sulfonate group. As the hydrocarbon group which may contain a fluorine atom, specifically, a methyl group, an ethyl group, a propyl group, an isopropyl group, a butyl group, a tertiary butyl group, a hexyl group, a nonyl group, a vinyl group, a phenyl group, a benzyl group, a 4-methylphenyl group, a trifluoromethyl group, a 2,2,2-trifluoroethyl group, a 4-(trifluoromethoxy) phenyl group and the like can be mentioned. It is preferably a methyl group, a vinyl group, a 4-methylphenyl group, or a 2,2,2-trifluoroethyl group.

A degradable polyethylene glycol derivative used for the bio-related substance bonded to the polyethylene glycol derivative of the present invention in, for example, a straight chain type can be produced by the route shown in the following process drawing (Process drawing (I)).

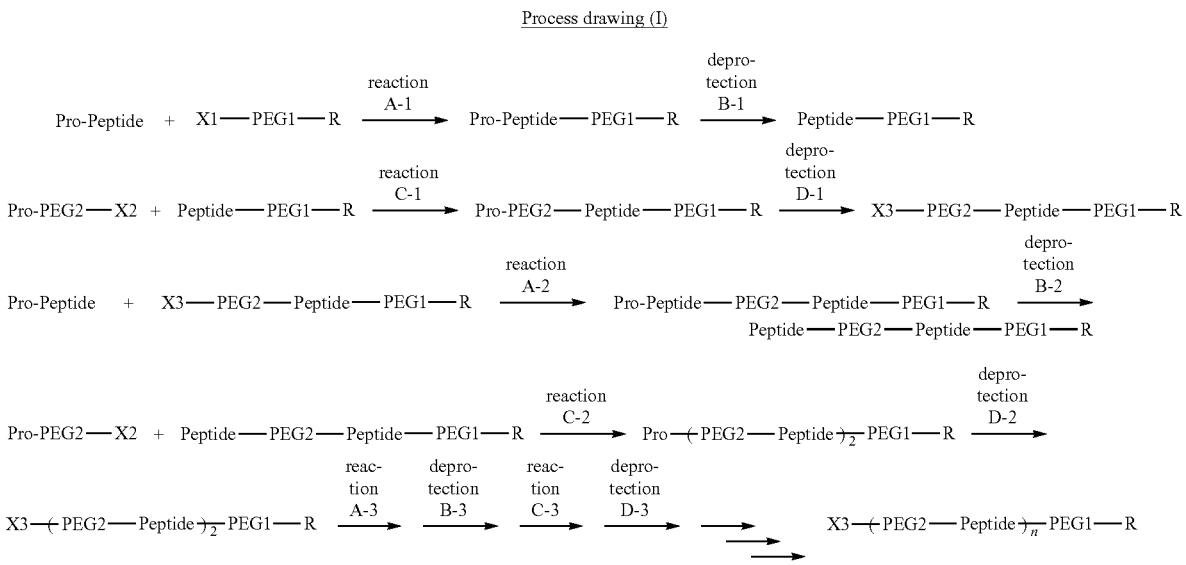

Process drawing (I)

wherein PEG1, PEG2 are polyethylene glycol derivatives, Peptide is oligopeptide, X1, X2, X3 are functional groups capable of reacting with oligopeptide of a polyethylene glycol derivative, Pro is a protecting group, and R is as defined above.

In Process drawing (I), PEG1, PEG2 are polyethylene glycol derivatives, and the molecular weight of each is as defined for the aforementioned n1, n2 as the number of repeating units of polyethylene glycol, namely, since n is 113-682, the molecular weight thereof is within the range of 5000-30000.

Peptide in Process drawing (I) is an oligopeptide defined for the aforementioned Z. In Process drawing (I), an oligopeptide having the N-terminal amino group protected by a protecting group, or an oligopeptide having the C terminal carboxyl group protected by a protecting group is used.

In Process drawing (I), X1, X2, X3 are each a functional group of a polyethylene glycol derivative capable of reacting with a carboxyl group or an amino group of Peptide.

In Process drawing (I), Pro is a protecting group. A protecting group is a component that prevents or inhibits the reaction of a particular chemically reactive functional group in a molecule under certain reaction conditions. Protecting groups vary depending on the kind of chemically reactive functional group to be protected, the conditions to be used and the presence of other functional group or protecting group in the molecule. Specific examples of the protecting group can be found in many general books, and they are described in, for example, "Wuts, P. G. M.; Greene, T. W. Protective Groups in Organic Synthesis, 4th ed.; Wiley-Interscience: New York, 2007". The functional group protected by a protecting group can be deprotected, that is, chemically reacted, using a reaction condition suitable for each protecting group, whereby the original functional group can be regenerated. Representative deprotection conditions for protecting groups are described in the aforementioned literature.

The reaction of the polyethylene glycol derivative and oligopeptide in Process drawing (I) is not particularly limited, and the polyethylene glycol derivative and oligopeptide are bonded by a covalent bond by a chemical reaction. The bond between the oligopeptide and polyethylene glycol is determined by the combination of the functional group to be used for the reaction. Basically, a bond formed by an alkylene group containing a urethane bond and an amide bond which is a divalent spacer shown by the aforementioned $L^1$, $L^2$, $L^3$, $L^4$, $L^5$ and the like is used.

In Process drawing (I), reaction A-1 is a reaction between an oligopeptide having one terminal protected by a protecting group and a polyethylene glycol derivative in which one terminal is R. In the subsequent deprotection B-1, a polyethylene glycol derivative having R on one terminal and oligopeptide on one terminal can be obtained.

In Process drawing (I), reaction C-1 is a reaction between a polyethylene glycol derivative having one terminal protected by a protecting group and a polyethylene glycol derivative having an oligopeptide at the terminal, which is obtained in deprotection B-1. In the subsequent deprotection D-1, a polyethylene glycol derivative in which two polyethylene glycol chains and one oligopeptide are linked can be obtained.

In Process drawing (I), reaction A-2 is a reaction between an oligopeptide with one terminal protected by a protecting group and a polyethylene glycol derivative in which two polyethylene glycol chains and one oligopeptide are linked, which is obtained in deprotection D-1. In the subsequent deprotection B-2, a polyethylene glycol derivative having oligopeptide on the terminal can be obtained.

In Process drawing (I), reaction C-2 is a reaction between a polyethylene glycol derivative having one terminal protected by a protecting group and the polyethylene glycol derivative with oligopeptide on the terminal and obtained in deprotection B-2. In the subsequent deprotection D-2, a polyethylene glycol derivative in which 3 polyethylene glycol chains and 2 oligopeptides are linked can be obtained.

By repeating the cycle of reaction A→deprotection B→reaction C→deprotection D in Process drawing (I), the degradable polyethylene glycol derivative of the present invention can be obtained.

In the degradable polyethylene glycol derivative, the terminal functional group can be chemically converted as necessary. For the reaction used for the functional group conversion, conventionally known methods can be used. It is necessary to appropriately select conditions that do not cause degradation of oligopeptides and the aforementioned divalent spacers.

As a typical example of the synthesis of the degradable polyethylene glycol derivative, the following process can be mentioned. Here, as a typical example of Process drawing (I), a synthesis method using an oligopeptide having the N-terminal amino group protected by a protecting group is described. The spacers $L^6$, $L^7$, $L^8$, $L^9$, $L^{10}$, $L^{11}$, $L^{12}$ in the subsequent processes are as defined for the divalent spacers shown by the aforementioned $L^1$, $L^2$, $L^3$, $L^4$, $L^5$.

reaction A-1

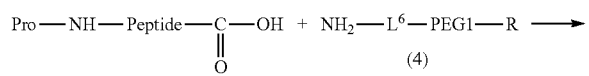

(4)

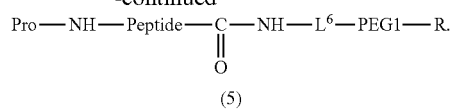

(5)

Reaction A-1 is a process for binding a carboxyl group of oligopeptide with the N-terminal amino group protected by a protecting group with an amino group of a polyethylene glycol derivative (4) having R at one terminal by a condensation reaction to give polyethylene glycol derivative (5).

The protecting group of the N-terminal amino group of oligopeptide is not particularly limited. For example, acyl protecting group and carbamate protecting group can be mentioned, and a trifluoroacetyl group, a 9-fluorenylmethyloxycarbonyl group, a t-butyloxycarbonyl group and the like can be specifically mentioned.

The condensation reaction is not particularly limited, and a reaction using a condensing agent is desirable. As the condensing agent, a carbodiimide condensing agent such as dicyclohexylcarbodiimide (DCC), 1-ethyl-3-(3-dimethylaminopropyl)carbodiimide hydrochloride (EDC) or the like may be used alone, or it may be used in combination with a reagent such as N-hydroxysuccinimide (NHS), 1-hydroxybenzotriazole (HOBt), 1-hydroxy-7-azabenzotriazole (HOAt) and the like. Also, a condensing agent with high reactivity such as HATU, HBTU, TATU, TBTU, COMU, DMT-MM and the like may be used. To promote the reaction, a base such as triethylamine, dimethylaminopyridine and the like may also be used.

Impurities by-produced in the reaction, or oligopeptides and condensing agents which were not consumed and remain in the reaction are preferably removed by purification. The purification is not particularly limited, and extraction, recrystallization, adsorption treatment, reprecipitation, column chromatography, supercritical extraction, and the like can be used for purification.

deprotection B-1

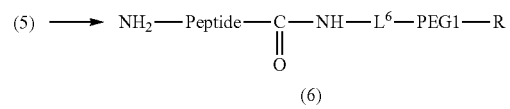

(6)

Deprotection B-1 is a process for removing the protecting group of polyethylene glycol derivative (5) obtained in reaction A-1 to give polyethylene glycol derivative (6). For the deprotection reaction, a conventionally-known method can be used. It is necessary to use conditions that do not cause degradation of oligopeptide and divalent spacer for $L^6$.

Impurities and the like by-produced in the deprotection reaction are preferably removed by purification. The purification is not particularly limited, and extraction, recrystallization, adsorption treatment, reprecipitation, column chromatography, supercritical extraction, and the like can be used for purification.

reaction C-1

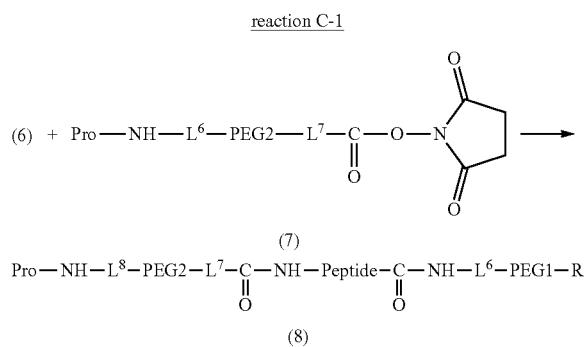

Reaction C-1 is a process for binding an amino group of polyethylene glycol derivative (6) obtained in deprotection B-1 with an active ester group or active carbonate group of polyethylene glycol derivative (7) by reaction to give polyethylene glycol derivative (8) having a structure in which two polyethylene glycol chains are linked by oligopeptide.

The polyethylene glycol derivative (7) has an amino group protected by a protecting group at one terminal, and an active ester group or active carbonate group and the like at the other terminal. As the leaving group for the active ester group and active carbonate group, a succinimidyloxy group, a phthalimidyloxy group, a 4-nitrophenoxy group, a 1-imidazolyl group, a pentafluorophenoxy group, a benzotriazol-1-yloxy group, a 7-azabenzotriazol-1-yloxy group and the like can be mentioned. The polyethylene glycol derivative (7) does not necessarily have an activated functional group. When it has a carboxyl group at the terminal, a reaction using a condensing agent can be performed as in reaction A-1. To promote the reaction, a base such as triethylamine, dimethylaminopyridine and the like may also be used. The protecting group of polyethylene glycol derivative (7) is not particularly limited and, for example, an acyl protecting group and a carbamate protecting group can be mentioned, and a trifluoroacetyl group, a 9-fluorenylmethyloxycarbonyl group, a t-butyloxycarbonyl group and the like can be specifically mentioned.

Impurities by-produced in the reaction, or polyethylene glycol derivative and the like which were not consumed and remain in the reaction are preferably removed by purification. The purification is not particularly limited, and extraction, recrystallization, adsorption treatment, reprecipitation, column chromatography, supercritical extraction, and the like can be used for purification.

As a method for removing polyethylene glycol impurities having different molecular weight and different functional group from polyethylene glycol derivative (8), the purification techniques described in JP-A-2014-208786, JP-A-2011-79934 can be used.

deprotection D-1

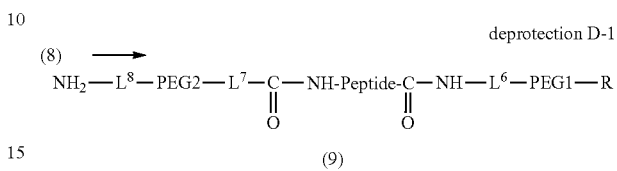

Deprotection D-1 is a process for removing the protecting group of polyethylene glycol derivative (8) obtained in reaction C-1 to give polyethylene glycol derivative (9). For the deprotection reaction, a conventionally-known method can be used. It is necessary to use conditions that do not cause degradation of oligopeptide and divalent spacer for $L^6$, $L^7$, $L^8$.

Impurities and the like by-produced in the deprotection reaction are preferably removed by purification. The purification is not particularly limited, and extraction, recrystallization, adsorption treatment, reprecipitation, column chromatography, supercritical extraction, and the like can be used for purification.

reaction A-2

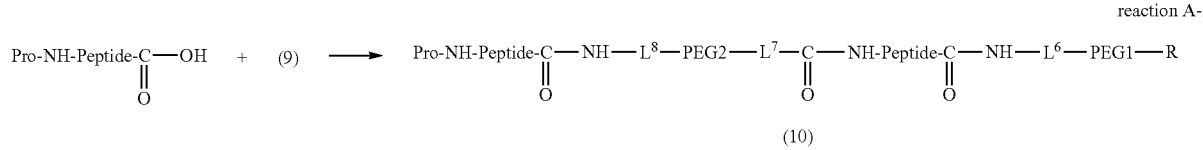

Reaction A-2 is a process for binding a carboxyl group of oligopeptide with the N-terminal amino group protected by a protecting group with an amino group of a polyethylene glycol derivative (9) obtained in deprotection B-1 by a condensation reaction to give polyethylene glycol derivative (10). The reaction and purification can be performed under the same conditions as in the aforementioned reaction A-1.

deprotection B-2

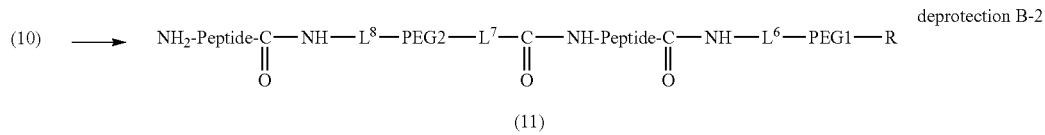

Deprotection B-2 is a process for removing the protecting group of polyethylene glycol derivative (10) obtained in reaction A-2 to give polyethylene glycol derivative (11). For the deprotection reaction, a conventionally-known method can be used. It is necessary to use conditions that do not cause degradation of oligopeptide and divalent spacer for $L^6$, $L^7$, $L^8$. The reaction and purification can be performed under the same conditions as in the aforementioned deprotection B-1.

reaction C-2

(7) + (11) ⟶

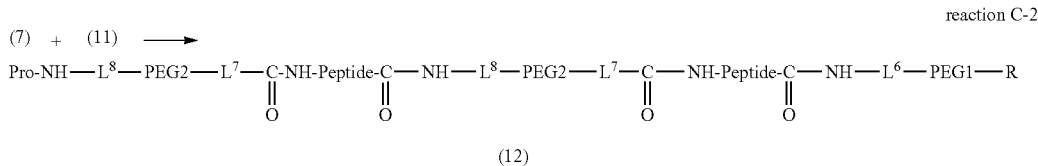

Reaction C-2 is a process for binding an amino group of polyethylene glycol derivative (11) obtained in deprotection B-2 with an active ester group or active carbonate group of polyethylene glycol derivative (7) by reaction to give polyethylene glycol derivative (12) having a structure in which three polyethylene glycol chains are linked by two oligopeptides. The reaction and purification can be performed under the same conditions as in the aforementioned reaction C-1.

(12) ⟶

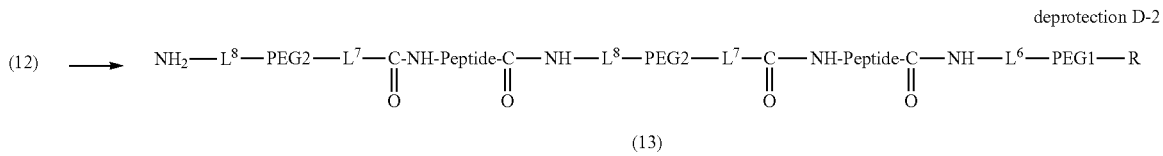

Deprotection D-2 is a process for removing the protecting group of polyethylene glycol derivative (12) obtained in reaction C-2 to give polyethylene glycol derivative (13). For the deprotection reaction, a conventionally-known method can be used. It is necessary to use conditions that do not cause degradation of oligopeptide and divalent spacer for $L^6$, $L^7$, $L^8$. The reaction and purification can be performed under the same conditions as in the aforementioned deprotection D-1.

The above reactions are summarized as the following Process drawing (II). By repeating the cycle of reaction A→deprotection B→reaction C→deprotection D, the degradable polyethylene glycol derivatives (9), (13), (14), (15) can be obtained.

Process drawing (II)

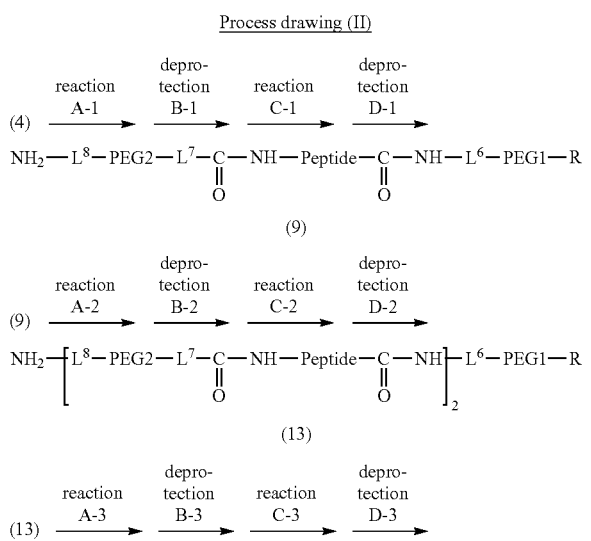

-continued

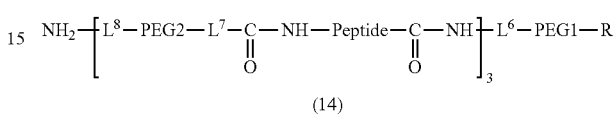

-continued

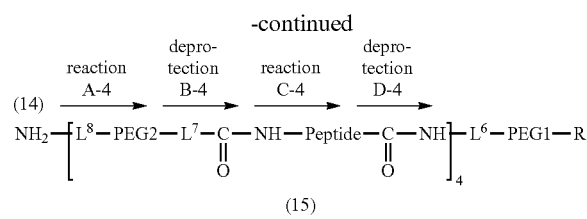

The degradable polyethylene glycol derivatives of (9), (13), (14) and (15) obtained in Process drawing (II) specifically correspond to the following.

Polyethylene glycol derivative (9): a polyethylene glycol derivative having a structure in which two polyethylene glycol chains are linked by one oligopeptide Polyethylene glycol derivative (13): a polyethylene glycol derivative having a structure in which three polyethylene glycol chains are linked by two oligopeptides Polyethylene glycol derivative (14): a polyethylene glycol derivative having a structure in which four polyethylene glycol chains are linked by three oligopeptides Polyethylene glycol derivative (15): a polyethylene glycol derivative having a structure in which five polyethylene glycol chains are linked by four oligopeptides The obtained degradable polyethylene glycol derivatives of (9), (13), (14), (15) have an amino group at the terminal. Utilizing this, conversion to various functional groups is possible. The reaction thereof is described below.

In addition, a degradable polyethylene glycol derivative having a different functional group can be obtained by changing the protecting group of the amino group of the polyethylene glycol derivative (7) used in reaction C-1, reaction C-2, reaction C-3, reaction C-4 in Process drawing (II) to, for example, an acetal group (specifically, 3,3-diethoxypropyl group etc.) which is a protecting group of aldehyde group, an alkyl ester protecting group (specifically, methyl ester, t-butyl ester, benzyl ester etc.) which is a protecting group of carboxyl group, or the like. In this case, the target product can be obtained by performing deprotection by a conventionally-known method suitable for each protecting group in deprotection D-1, deprotection D-2, deprotection D-3, deprotection D-4.

Examples of the polyethylene glycol derivative replacing polyethylene glycol derivative (7) include those having the following structures.

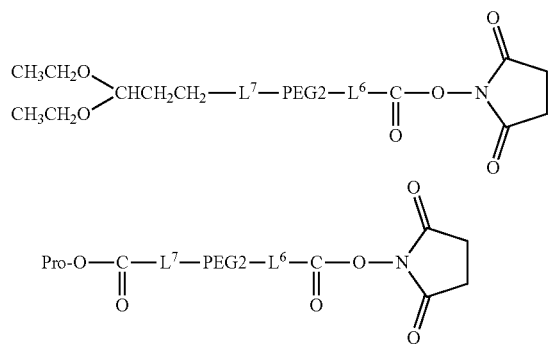

As a different production method of the degradable polyethylene glycol derivative of the present invention, for example, it can also be produced by the route shown in the following Process drawing (Process drawing (III)).

Peptide in Process drawing (III) is an oligopeptide defined for the aforementioned Z. In Process drawing (III), an oligopeptide having the N-terminal amino group protected by a protecting group, or an oligopeptide having the C terminal carboxyl group protected by a protecting group is used.

In Process drawing (III), X1, X2, X3, X4, X5 are each a carboxyl group of Peptide, or a functional group of a polyethylene glycol derivative capable of reacting with an amino group.

In Process drawing (III), Pro, Pro2, Pro3 are protecting groups. In Process drawing (III), Pro is a protecting group stable under the deprotection conditions of Pro2, and Pro2 is a protecting group stable under the deprotection conditions of Pro3. A combination of these protecting groups can be selected from the protecting groups described in, for example, "Wuts, P. G. M.; Greene, T. W. Protective Groups in Organic Synthesis, 4th ed.; Wiley-Interscience: New York, 2007".

The reaction of the polyethylene glycol derivative and oligopeptide in Process drawing (III) is not particularly limited, and the polyethylene glycol derivative and oligopeptide are bonded by a covalent bond by a chemical reaction. The bond between the oligopeptide and polyethylene glycol is determined by the combination of the functional group to be used for the reaction. Basically, a bond formed by an alkylene group containing a urethane bond and

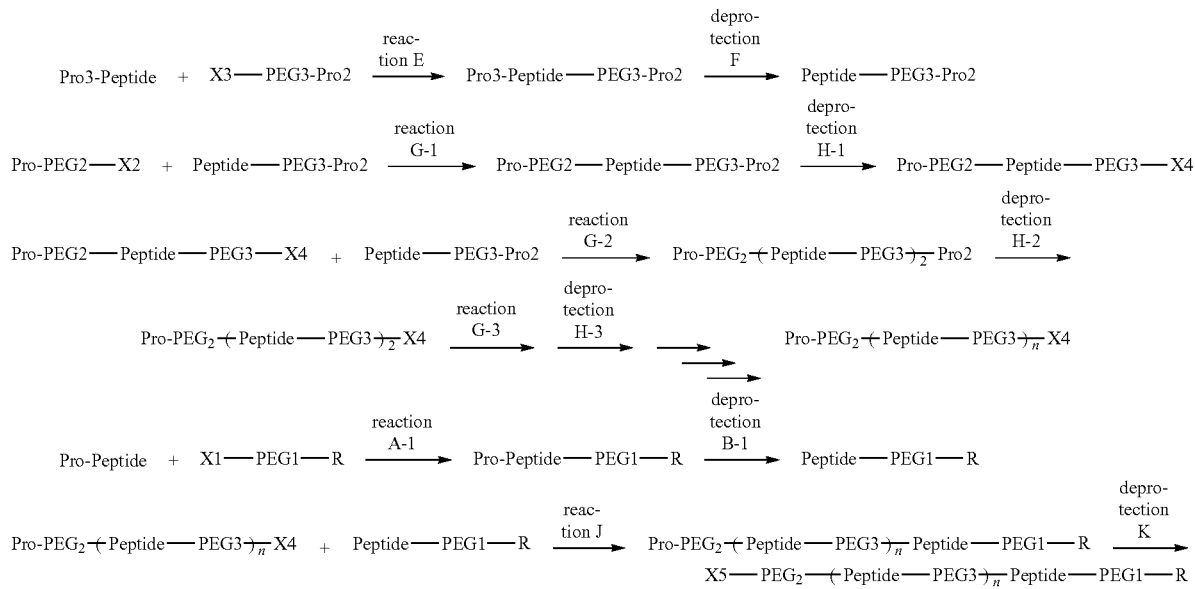

wherein PEG1, PEG2, PEG3 are polyethylene glycol derivatives, Peptide is oligopeptide, X1, X2, X3, X4, X5 are functional groups of a polyethylene glycol derivative, Pro, Pro2, Pro3 are each a protecting group, and R is as defined above.

In Process drawing (III), PEG1, PEG2, PEG3 are polyethylene glycol derivatives, and the molecular weight of each is as defined for the aforementioned n1, n2 as the number of repeating units of polyethylene glycol, namely, since n is 113-682, the molecular weight thereof is within the range of 5000-30000.

an amide bond which is a divalent spacer shown by the aforementioned $L^1$, $L^2$, $L^3$, $L^4$, $L^5$ and the like is used.

In Process drawing (III), reaction E is a reaction between an oligopeptide having one terminal protected by protecting group Pro3 and a polyethylene glycol derivative having one terminal protected by protecting group Pro2. In the subsequent deprotection F, only the protecting group Pro3 on the peptide side is deprotected, whereby a polyethylene glycol derivative having oligopeptide at one terminal and protecting group Pro2 at one terminal can be obtained.

In Process drawing (III), reaction G-1 is a reaction between a polyethylene glycol derivative having one terminal protected by a protecting group Pro and a polyethylene glycol derivative having an oligopeptide at one terminal and a protecting group Pro2 at one terminal which is obtained in deprotection F. In the subsequent deprotection H-1, the protecting group Pro2 alone at one terminal of the polyethylene glycol derivative is deprotected to give a polyethylene glycol derivative in which two polyethylene glycol chains and one oligopeptide are linked.

In Process drawing (III), reaction G-2 is a reaction between a polyethylene glycol derivative having one terminal protected by a protecting group Pro and obtained in deprotection H-1 and a polyethylene glycol derivative having an oligopeptide at one terminal and a protecting group Pro2 at one terminal which is obtained in deprotection F. In the subsequent deprotection H-2, the protecting group Pro2 alone at one terminal of the polyethylene glycol derivative is deprotected to give a polyethylene glycol derivative in which three polyethylene glycol chains and two oligopeptides are linked.

By repeating reactions of reaction G and deprotection H using a polyethylene glycol derivative having an oligopeptide at one terminal and a protecting group Pro2 at one terminal which is obtained in deprotection F after reaction E in Process drawing (III) as a starting material in reaction processes G-1, G-2, G-3, precursors for the degradable polyethylene glycol derivative of the present invention can be efficiently obtained.

In Process drawing (III), reaction A-1 and deprotection B-1 are the same as the aforementioned Process drawing (I), and a polyethylene glycol derivative having R on one terminal and oligopeptide on one terminal can be obtained.

In Process drawing (III), reaction J is a reaction between a polyethylene glycol derivative (precursor) having one terminal protected by protecting group Pro, which was obtained by repeating the reactions of reaction G and deprotection H, and a polyethylene glycol derivative having R at one terminal and an oligopeptide at one terminal, which was obtained in deprotection B-1. In the subsequent deprotection K, the degradable polyethylene glycol derivative of the present invention can be obtained.

In the degradable polyethylene glycol derivative, the terminal functional group can be chemically converted as necessary. For the reaction used for the functional group conversion, conventionally known methods can be used. It is necessary to appropriately select conditions that do not cause degradation of oligopeptides and the aforementioned divalent spacers.

As a typical example of the synthesis of the degradable polyethylene glycol derivative, the following process can be mentioned. Here, as a typical example of Process drawing (III), a synthesis method using an oligopeptide having the N-terminal amino group protected by a protecting group is described.

reaction E

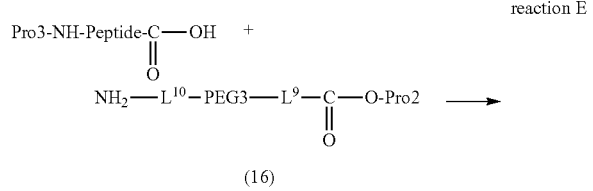

(16)

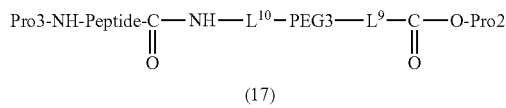

(17)

Reaction E is a process for binding a carboxyl group of oligopeptide with the N-terminal amino group protected by a protecting group Pro3 with an amino group of a polyethylene glycol derivative (16) with a carboxyl group protected by a protecting group Pro2 at one terminal by a condensation reaction to give polyethylene glycol derivative (17).

The protecting group Pro3 of the N-terminal amino group of oligopeptide is not particularly limited. For example, acyl protecting group and carbamate protecting group can be mentioned, and a trifluoroacetyl group, a 9-fluorenylmethyloxycarbonyl group, and the like can be specifically mentioned. The protecting group Pro2 of the carboxyl group of polyethylene glycol derivative (16) is not particularly limited, and a t-butyl group and the like can be mentioned.

The reaction and purification can be performed under the same conditions as in the aforementioned reaction A-1.

deprotection F

(17) ⟶

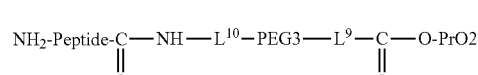

(18)

Deprotection F is a process for removing the protecting group Pro3 of amino group of polyethylene glycol derivative (17) obtained in reaction E to give polyethylene glycol derivative (18). For the deprotection reaction, a conventionally-known method can be used. It is necessary to use conditions that do not cause degradation of protecting group Pro2, oligopeptide, and divalent spacer for $L^9$, $L^{10}$. For example, specifically, when Pro3 is a 9-fluorenylmethyloxycarbonyl group, and Pro2 is a t-butyl group, Pro3 can be selectively deprotected using an appropriate base compound such as piperidine and the like. The reaction and purification can be performed under the same conditions as in the aforementioned deprotection B-1.

reaction G-1

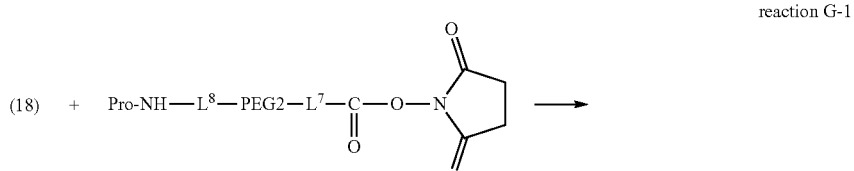

(7)

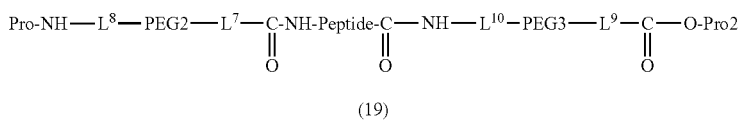

(19)

Reaction G-1 is a process for binding an amino group of polyethylene glycol derivative (18) obtained in deprotection F with an active ester group or active carbonate group of polyethylene glycol derivative (7) by reaction to give polyethylene glycol derivative (19) having a structure in which two polyethylene glycol chains are linked by one oligopeptide. Polyethylene glycol derivative (7) is as described above. The reaction and purification can be performed under the same conditions as in the aforementioned reaction C-1.

Reaction G-2 is a process for binding an amino group of polyethylene glycol derivative (18) obtained in deprotection F with a carboxyl group of polyethylene glycol derivative (20) obtained in deprotection H-1 by a condensation reaction to give polyethylene glycol derivative (21) having a structure in which three polyethylene glycol chains are linked by two oligopeptides. The reaction and purification can be performed under the same conditions as in the aforementioned reaction C-1.

deprotection H-1

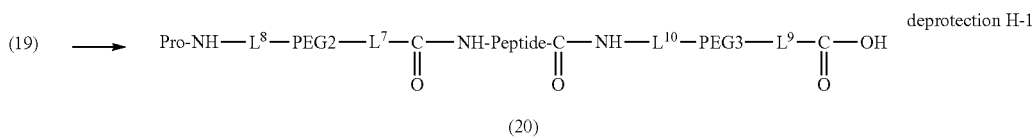

(20)

Deprotection H-1 is a process for removing the protecting group Pro2 of carboxyl group of polyethylene glycol derivative (19) obtained in reaction G-1 to give polyethylene glycol derivative (20). For the deprotection reaction, a conventionally-known method can be used. It is necessary to use conditions that do not cause degradation of protecting group Pro, oligopeptide and divalent spacers for $L^7$, $L^8$, $L^9$, $L^{10}$. For example, specifically, when Pro is a trifluoroacetyl group, and Pro2 is a t-butyl group, Pro2 can be selectively deprotected under conditions using an appropriate acidic compound.

Impurities and the like by-produced in the deprotection reaction are preferably removed by purification. The purification is not particularly limited, and extraction, recrystallization, adsorption treatment, reprecipitation, column chromatography, supercritical extraction, and the like can be used for purification.

Similar to the aforementioned reaction A-1, a reaction using a condensing agent is desirable. To promote the reaction, a base such as triethylamine, dimethylaminopyridine and the like may also be used.

Impurities by-produced in the reaction, or polyethylene glycol derivative and the like which were not consumed and remain in the reaction are preferably removed by purification. The purification is not particularly limited, and extraction, recrystallization, adsorption treatment, reprecipitation, column chromatography, supercritical extraction, and the like can be used for purification.

As a method for removing polyethylene glycol impurities having different molecular weight and different functional group from polyethylene glycol derivative (21), the purification techniques described in JP-A-2014-208786, JP-A-2011-79934 can be used.

reaction G-2

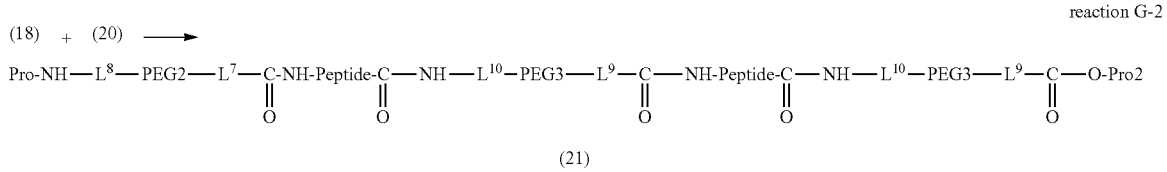

(21)

(21) →

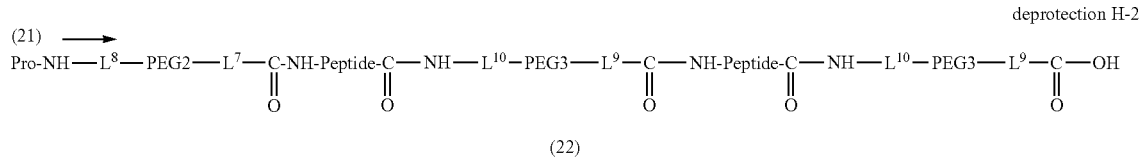

(22)

Deprotection H-2 is a process for removing the protecting group Pro2 of carboxyl group of polyethylene glycol derivative (21) obtained in reaction G-2 to give polyethylene glycol derivative (22). For the deprotection reaction, a conventionally-known method can be used. It is necessary to use conditions that do not cause degradation of protecting group Pro, oligopeptide and divalent spacer for $L^7$, $L^8$, $L^9$, $L^{10}$.

The above reactions are summarized as the following Process drawing (IV). By repeating the cycle of reaction G→deprotection H using polyethylene glycol derivative (18) obtained by reaction E and deprotection F as a starting material, for example, intermediates for the degradable polyethylene glycol derivative of the present invention such as polyethylene glycol derivative (23) having a structure in which four polyethylene glycol chains are linked by three oligopeptides, polyethylene glycol derivative (24) having a structure in which five polyethylene glycol chains are linked by four oligopeptides and the like can be obtained.

The polyethylene glycol derivatives of (20), (22), (23) and (24) obtained in Process drawing (IV) specifically correspond to the following.

Polyethylene glycol derivative (20): a polyethylene glycol derivative having a structure in which two polyethylene glycol chains are linked by one oligopeptide Polyethylene glycol derivative (22): a polyethylene glycol derivative having a structure in which three polyethylene glycol chains are linked by two oligopeptides Polyethylene glycol derivative (23): a polyethylene glycol derivative having a structure in which four polyethylene glycol chains are linked by three oligopeptides Polyethylene glycol derivative (24): a polyethylene glycol derivative having a structure in which five polyethylene glycol chains are linked by four oligopeptides Then, a degradable polyethylene glycol derivative can be obtained by performing the following reaction J and deprotection K using polyethylene glycol derivatives (20), (22), (23), (24) obtained in Process drawing (IV) as starting materials. The following process shows when polyethylene glycol derivative (24) was used.

Process drawing (IV)

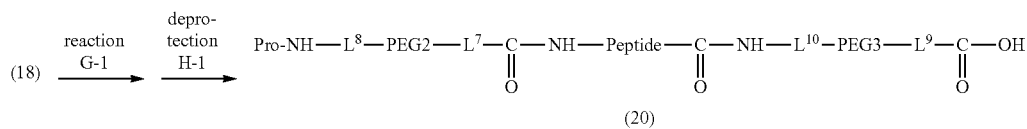

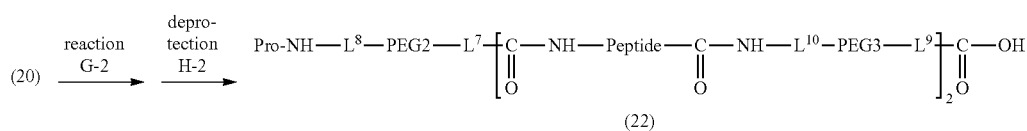

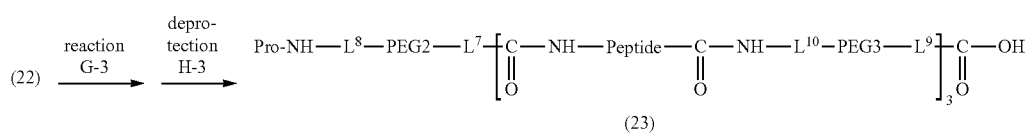

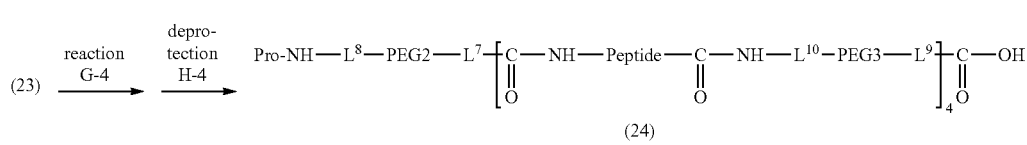

reaction J (6) + (24) →

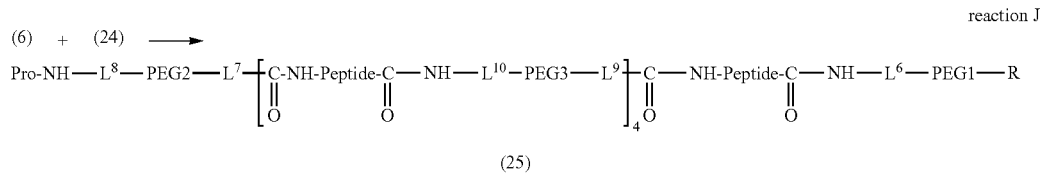

(25)

Reaction J is a process for a condensation reaction of an amino group of polyethylene glycol derivative (6) obtained in the aforementioned deprotection B-1 and a carboxyl group of polyethylene glycol derivative (24) obtained in deprotection H-4 to give polyethylene glycol derivative (25) having a structure in which six polyethylene glycol chains are linked by five oligopeptides. The reaction and purification can be performed under the same conditions as in the aforementioned reaction C-1.

Similar to the aforementioned reaction A-1, a reaction using a condensing agent is desirable. To promote the reaction, a base such as triethylamine, dimethylaminopyridine and the like may also be used.

Impurities by-produced in the reaction, or polyethylene glycol derivative and the like which were not consumed and remain in the reaction are preferably removed by purification. The purification is not particularly limited, and extraction, recrystallization, adsorption treatment, reprecipitation, column chromatography, supercritical extraction, and the like can be used for purification.

As a method for removing polyethylene glycol impurities having different molecular weight and different functional group from polyethylene glycol derivative (25), the purification techniques described in JP-A-2014-208786, JP-A-2011-79934 can be used.

Process drawing (V)

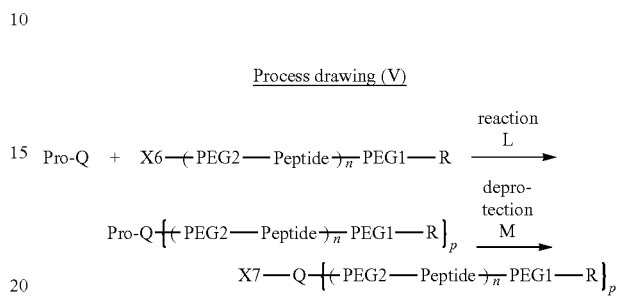

wherein PEG1, PEG2 are polyethylene glycol derivatives, Peptide is oligopeptide, Q is a residue of a compound having 3-5 active hydrogens, X6 and X7 are functional groups, Pro is a protecting group, p is 2-4, and R is as defined above.

In Process drawing (V), PEG1, PEG2 are polyethylene glycol derivatives, and the molecular weight of each is as defined for the aforementioned n1, n2 as the number of repeating units of polyethylene glycol, namely, since n is 45-682, the molecular weight thereof is within the range of 2000-30000.

Peptide in Process drawing (V) is an oligopeptide defined for the aforementioned Z.

deprotection K

(25) →

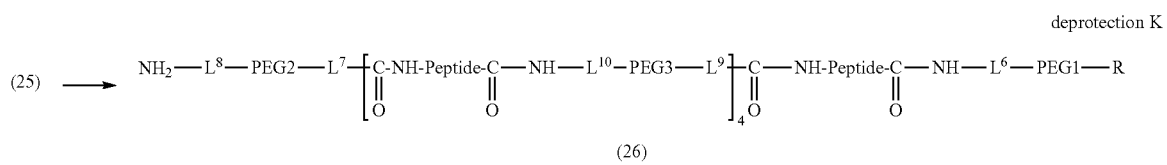

(26)

Deprotection K is a process for removing the protecting group of polyethylene glycol derivative (25) obtained in reaction J to give polyethylene glycol derivative (26). For the deprotection reaction, a conventionally-known method can be used. It is necessary to use conditions that do not cause degradation of oligopeptide and divalent spacer for $L^6$, $L^7$, $L^8$, $L^9$, $L^{10}$. The reaction and purification can be performed under the same conditions as in the aforementioned deprotection D-1.

As a different production method of the degradable polyethylene glycol derivative to be used for the bio-related substance bonded to the polyethylene glycol derivative of the present invention when it is a branched, for example, it can also be produced by the route shown in the following Process drawing (Process drawing (V)). Here, a branched degradable polyethylene glycol is obtained by a reaction between a degradable polyethylene glycol obtained in process (I) or process (III) and Q which is a residue of a compound having 3-5 active hydrogens.

In Process drawing (V), Q is a residue of a compound having 3-5 active hydrogens as defined for the aforementioned Q.

In Process drawing (V), X6 is a functional group of a polyethylene glycol derivative capable of reacting with a hydroxyl group, a carboxyl group, an amino group and the like which are functional groups having active hydrogen for Q, and X7 is a functional group capable of reacting with a bio-related substance bonded to Q.

The reaction of Q and the degradable polyethylene glycol derivative in Process drawing (V) is not particularly limited, and Q and the degradable polyethylene glycol derivative are bonded by a covalent bond by a chemical reaction. The bond between Q and the degradable polyethylene glycol derivative is determined by the combination of the functional group to be used for the reaction. Basically, a bond formed by an alkylene group containing a urethane bond and an amide bond which is a divalent spacer shown by the aforementioned $L^1$, $L^2$, $L^3$, $L^4$, $L^5$ and the like is used.

In Process drawing (V), reaction L is a reaction between Q which is a residue of a compound having 3-5 active hydrogens wherein one functional group with an active hydrogen is protected by protecting group Pro, and a degradable polyethylene glycol derivative having R at one terminal obtained in the aforementioned process (I) or process (III). In the subsequent deprotection M, protecting group Pro of Q can be deprotected to give a branched degradable polyethylene glycol derivative. In the degradable polyethylene glycol derivative, the terminal functional group can be chemically converted as necessary. For the reaction used for the functional group conversion, conventionally known methods can be used. It is necessary to appropriately select conditions that do not cause degradation of oligopeptides and the aforementioned divalent spacers.

As a typical example of the synthesis of the degradable polyethylene glycol derivative, the following process can be mentioned. Here, as a typical example of Process drawing (V), a synthesis method using, as Q, a residue of glutamic acid which is a compound having 3 active hydrogens is explained.

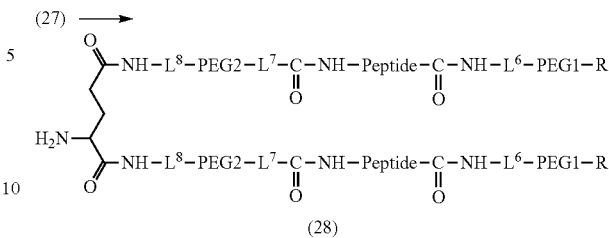

Deprotection M is a process for removing the protecting group of polyethylene glycol derivative (27) obtained in reaction L to give polyethylene glycol derivative (28). For the deprotection reaction, a conventionally-known method can be used. It is necessary to use conditions that do not cause degradation of oligopeptide and divalent spacer for $L^6$, $L^7$, $L^8$. The reaction and purification can be performed under the same conditions as in the aforementioned deprotection D-1.

As a different production method of the branched degradable polyethylene glycol derivative of the present invention, for example, it can also be produced by the route shown in the following Process drawing (Process drawing (VI)). Here, a branched degradable polyethylene glycol is obtained by a reaction between a polyethylene glycol derivative having

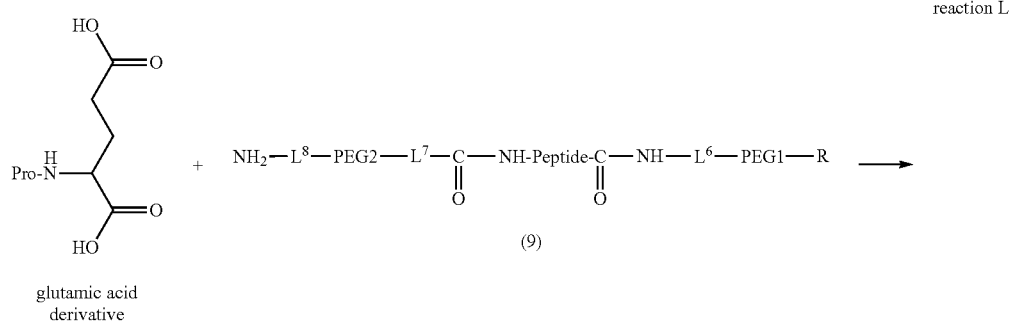

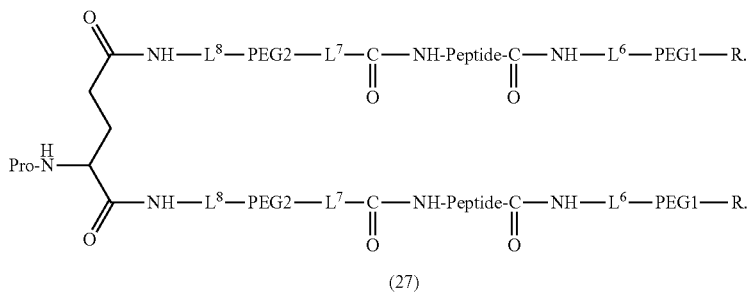

Reaction L is a process for binding, for example, an amino group of polyethylene glycol derivative (9) obtained in deprotection D-1, and two carboxyl groups of a glutamic acid derivative in which an amino group is protected by a protecting group by a condensation reaction to give branched polyethylene glycol derivative (27) having a structure in which two degradable polyethylene glycol chains are linked by a glutamic acid residue. The reaction and purification can be performed under the same conditions as in the aforementioned reaction G-2.

peptide at one terminal which is obtained in process (I) and process (III), and a branched polyethylene glycol derivative wherein polyethylene glycol is bonded to Q which is a residue of a compound having 3-5 active hydrogens.

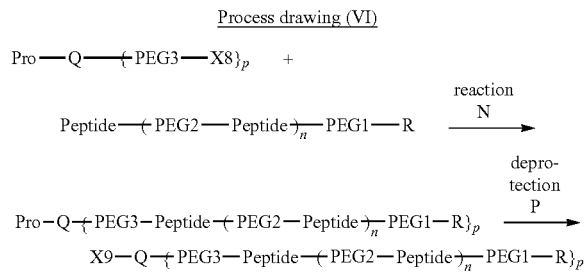

wherein PEG1, PEG2, PEG3 are polyethylene glycol derivatives, Peptide is oligopeptide, Q is a residue of a compound having 3-5 active hydrogens, X8 and X9 are functional groups, Pro is a protecting group, p is 2-4, and R is as defined above.

In Process drawing (VI), PEG1, PEG2, PEG3 are polyethylene glycol derivatives, and the molecular weight of each is as defined for the aforementioned n1, n2 as the number of repeating units of polyethylene glycol, namely, since n is 45-682, the molecular weight thereof is within the range of 2000-30000.

In Process drawing (VI), Peptide is an oligopeptide defined for the aforementioned Z.

compound having 3-5 active hydrogens is not particularly limited, and these polyethylene glycol derivatives are bonded by a covalent bond by a chemical reaction. The bond between the branched polyethylene glycol derivative and the degradable polyethylene glycol derivative is determined by the combination of the functional group to be used for the reaction. Basically, a bond formed by an alkylene group containing a urethane bond and an amide bond which is a divalent spacer shown by the aforementioned $L^1$, $L^2$, $L^3$, $L^4$, $L^5$ and the like is used.

In Process drawing (VI), reaction N is a reaction between a branched polyethylene glycol derivative wherein one functional group of Q which is a residue of a compound having 3-5 active hydrogens is protected by protecting group Pro and a polyethylene glycol derivative having peptide at one terminal and R at the other terminal, which is obtained in the aforementioned step (I) or step (III). In the subsequent deprotection P, protecting group Pro of Q can be deprotected to give a branched degradable polyethylene glycol derivative. In the degradable polyethylene glycol derivative, the terminal functional group can be chemically converted as necessary. For the reaction used for the functional group conversion, conventionally known methods can be used. It is necessary to appropriately select conditions that do not cause degradation of oligopeptides and the aforementioned divalent spacers.

As a typical example of the synthesis of the degradable polyethylene glycol derivative, the following process can be mentioned. Here, as a typical example of Process drawing (VI), a synthesis method using branched polyethylene glycol derivative wherein Q is a glycerol residue is explained.

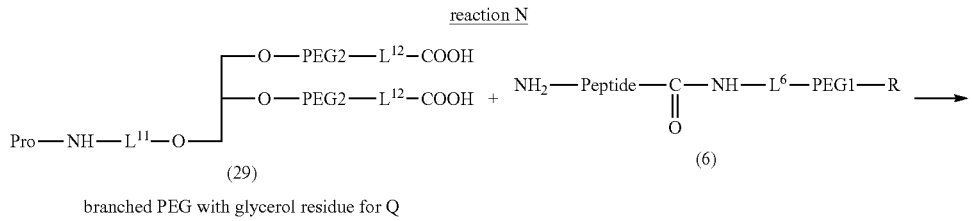

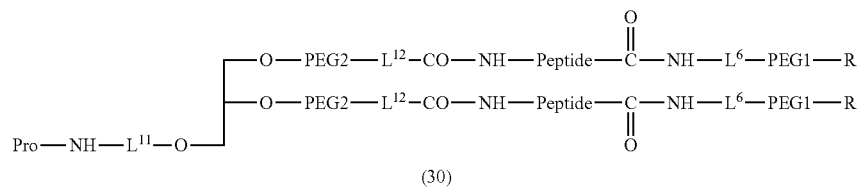

In Process drawing (VI), X8 is a functional group of a polyethylene glycol derivative capable of reacting with a carboxyl group or an amino group of Peptide, and X9 is a functional group capable of reacting with a bio-related substance bonded to Q.

In Process drawing (VI), the reaction between polyethylene glycol derivative having peptide at one terminal and a branched polyethylene glycol derivative in which polyethylene glycol is bonded to Q which is a residue of a Reaction N is a process for binding two carboxyl groups of branched polyethylene glycol derivative (29) obtained according to, for example, the Examples of patent document JP-A-2012-25932 with an amino group of a polyethylene glycol derivative (6) obtained in deprotection B-1 by a condensation reaction to give branched polyethylene glycol derivative (30). The reaction and purification can be performed under the same conditions as in the aforementioned reaction G-2.

deprotection P

(30) ⟶

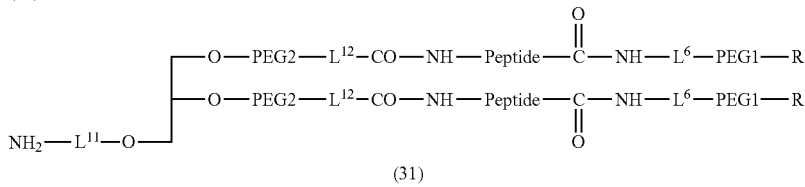

(31)

Deprotection P is a process for removing the protecting group of polyethylene glycol derivative (30) obtained in reaction N to give polyethylene glycol derivative (31). For the deprotection reaction, a conventionally-known method can be used. It is necessary to use conditions that do not cause degradation of oligopeptide and divalent spacer for $L^6$, $L^{11}$, $L^{12}$. The reaction and purification can be performed under the same conditions as in the aforementioned deprotection D-1.

The polyethylene glycol derivatives obtained in deprotection D, deprotection K, deprotection M, deprotection P have an amino group at the terminal. Utilizing this, conversion to various functional groups is possible.

The step of converting the terminal amino group of the polyethylene glycol derivative into another functional group is not particularly limited. Basically, conversion to various functional groups can be easily performed using a compound having an active ester group capable of reacting with an amino group, or a general reaction reagent such as acid anhydride, acid chloride, or the like.

For example, when conversion of the terminal amino group of a polyethylene glycol derivative to a maleimide group is desired, the desired product can be obtained by reacting with the following reagents.

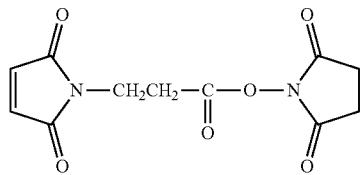

For example, when conversion of the terminal amino group of a polyethylene glycol derivative to a carboxyl group is desired, the desired product can be obtained by reacting with succinic anhydride or glutaric anhydride.

Since these reaction reagents are low-molecular-weight reagents and have solubility vastly differences from that of polyethylene glycol derivatives, they can be easily removed by general purification methods such as extraction and crystallization.

The degradable polyethylene glycol obtained through the above steps is required to be stable in blood and have the property of being degraded only in cells. To properly evaluate the property, for example, the following test is performed, based on which the stability in blood and degradability in cells of the degradable polyethylene glycol can be evaluated.

The test method for evaluating the stability of degradable polyethylene glycol derivative in blood is not particularly limited. For example, a test using serum of mouse, rat, human or the like can be mentioned. Specifically, a polyethylene glycol derivative is dissolved in serum to a concentration of 1-10 mg/mL, incubated at 37° C. for 96 hr, the polyethylene glycol derivative contained in the serum is recovered and GPC is measured to evaluate the degradation rate. The degradation rate is calculated from the peak area % of the GPC main fraction of the polyethylene glycol derivative before the stability test and the peak area % of the GPC main fraction of the polyethylene glycol derivative after the stability test. Specifically, the following formula is used.

degradation rate=(peak area % before test−peak area % after test)÷peak area % before test×100

For example, when the peak area % of the GPC main fraction of the degradable polyethylene glycol derivative before the stability test is 95% and the peak area % of the GPC main fraction of the degradable polyethylene glycol derivative after the stability test is 90%, the degradation rate is calculated as follows.

degradation rate=(95−90)÷95×100=5.26(%)

When the degradable polyethylene glycol derivative is degraded in blood, the desired half-life in blood cannot be achieved. Thus, in the stability test, the degradation rate after 96 hr is preferably not more than 10%, more preferably not more than 5%.

The test method for evaluating the intracellular degradability of the degradable polyethylene glycol derivative is not particularly limited. For example, a test including culturing cells in a medium containing a degradable polyethylene glycol derivative and the like can be mentioned. The cells and medium to be used here are not particularly limited. Specifically, a polyethylene glycol derivative is dissolved in RPMI-1640 medium to a concentration of 1-20 mg/mL, macrophage cells RAW264.7 are cultured in the medium at 37° C. for 96 hr, the polyethylene glycol derivative in the cells is recovered, and GPC is measured to evaluate the degradation rate. The degradation rate is calculated using the peak area % of the GPC main fraction of the polyethylene glycol derivative before and after the test.

For example, when the peak area % of the GPC main fraction of the degradable polyethylene glycol derivative before the degradability test is 95% and the peak area % of the GPC main fraction of the degradable polyethylene glycol derivative after the test is 5%, the degradation rate is calculated as follows.

degradation rate=(95−5)÷95×100=94.7(%)

When the degradable polyethylene glycol derivative is not efficiently degraded in cells, the desired suppression of cell vacuoles cannot be achieved. Thus, in the degradability test, the degradation rate after 96 hr is preferably not less than 90%, more preferably not less than 95%.

The method for binding the obtained degradable polyethylene glycol derivative to a bio-related substance is not particularly limited, and for example, the methods described in "Hermanson, G. T. Bioconjugate Techniques, 3rd ed.; Academic Press: San Diego, CA, 2013" and "Mark, Sonny S. Bioconjugate protocols, strategies and methods; 2011" can be used. Among them, for example, when targeting an amino group of a lysine residue of a protein or peptide, which is a bio-related substance, a polyethylene glycol derivative having an activated ester group or an activated carbonate group is used. When targeting a thiol group of a cysteine residue of a protein or peptide, which is a bio-related substance, a polyethylene glycol derivative having a maleimide group or an iodoacetamide group is used. Since the number of free cysteine residues contained in a natural bio-related substance is extremely small, polyethylene glycol can be more selectively bound to the bio-related substance by this method. Furthermore, as a method of generating or introducing a thiol group, a method of cleaving a disulfide bond of a bio-related substance, a method of modifying a bio-related substance by genetic engineering to introduce a cysteine residue, and the like are available. It is known that, by combining with these techniques, a desired number of polyethylene glycol derivatives can be bonded to a desired site of a bio-related substance.

Next, when targeting the N-terminal amino group of a protein or peptide, which is a bio-related substance, a polyethylene glycol derivative having an aldehyde group is used. Specifically, a polyethylene glycol derivative can be selectively bonded to the N-terminal amino group of a protein or peptide by using a polyethylene glycol derivative having an aldehyde group and a suitable reducing agent in a low pH buffer solution.

Bio-related substances bonded to these polyethylene glycol derivatives can be purified by dialysis, gel permeation chromatography (GPC), ion exchange chromatography (IEC), and the like, which are known as general methods. In addition, the obtained bio-related substances can be generally evaluated by analytical methods such as matrix-assisted laser desorption/ionization time-of-flight mass spectrometer (MALDI-TOF-MS), polyacrylamide gel electrophoresis (SDS-PAGE), reverse phase chromatography (RPLC) and the like.

The method for evaluating the physiological activity of a bio-related substance bonded to a degradable polyethylene glycol derivative is not particular limited. For example, when the bio-related substance is insulin, blood sugar concentration is measured, and when it is calcitonin, blood calcium concentration is measured, by periodically collecting blood from the animal that received administration and measuring the substance in the blood by using an appropriate analytical instrument, and the like, based on which the evaluation can be performed. Specifically, in the case of insulin, a glucose measurement kit is used to monitor a decrease in glucose concentration after administration and, in the case of calcitonin, a decrease in calcium concentration after administration is monitored using a calcium measurement kit, based on which the evaluation can be performed.

The test method for evaluating the half-life in blood and distribution in vivo of a bio-related substance bonded to a degradable polyethylene glycol derivative is not particularly limited. For example, a test including labeling with radioactive isotope or fluorescent substance, administering to mice and rats, followed by monitoring and the like can be mentioned.

A degradable peptide introduced into a polyethylene glycol derivative imparts intracellular degradability to polyethylene glycol. However, the peptide structure thereof may change the pharmacokinetics of a bio-related substance bonded to polyethylene glycol. To confirm the effect of the so introduced peptide structure on the pharmacokinetics, it is necessary to compare the blood half-life and distribution thereof in the body with those of a bio-related substance modified with a polyethylene glycol derivative with the same molecular weight and free of degradability. Specifically, radioisotope-labeled bio-related substances are respectively bonded with a nondegradable polyethylene glycol derivative and a degradable polyethylene glycol derivative, the obtained two kinds of bio-related substances are administered to mice, the radiation dose of blood and each organ is measured at plural time points, and quantification measurement can be performed.

The test method for evaluating suppression of cell vacuoles by a degradable polyethylene glycol derivative is not particularly limited. For example, as described in non-patent document 2, a test including continuing administration to mice and rats at high frequency and high dose for a long period of time and confirming images of the sections of organ and internal organ that are said to be susceptible to vacuole formation can be mentioned.

Specifically, a polyethylene glycol derivative is dissolved in saline to a concentration of 10-250 mg/mL, 20-100 μL thereof is continuously administered from the mouse tail vein 3 times per week for 4 weeks or longer, paraffin sections of choroid plexus, spleen, and the like that are organs said to be susceptible to vacuole formation are prepared and stained, and the images of the sections are confirmed by a pathological method to evaluate suppression of vacuoles.

In this evaluation, the dose of polyethylene glycol needs to be in large excess compared to the dose of polyethylene glycol that is generally used in the art.

Non-patent document 2 describes that vacuolization of cells by high-molecular-weight polyethylene glycol is related to accumulation of polyethylene glycol in tissue. The test method for evaluating accumulation of a degradable polyethylene glycol derivative in cells is not particularly limited, and evaluation can be made using section images prepared by the same method as the above-mentioned evaluation of vacuole. Stained section images of choroid plexus, spleen, and the like that are organs said to be susceptible to polyethylene glycol accumulation are confirmed by a pathological method, and accumulation of polyethylene glycol can be evaluated.

In this evaluation, the dose of polyethylene glycol needs to be in large excess compared to the dose of polyethylene glycol that is generally used in the art.

EXAMPLE $^1$H-NMR obtained in the following Examples was obtained from JNM-ECP400 or JNM-ECA600 manufactured by JEOL Datam Co., Ltd. A φ5 mm tube was used for the measurement, and $D_2O$ and $CDCl_3$ and $d_6$-DMSO containing tetramethylsilane (TMS) as an internal standard substance were used as deuterated solvents. The molecular weight and amine purity of the obtained polyethylene glycol derivative were calculated using liquid chromatography (GPC and HPLC). As a liquid chromatography system, "HLC-8320GPC EcoSEC" manufactured by Tosoh Corporation was used for GPC, and "ALLIANCE" manufactured by WATERS was used for HPLC. The analysis conditions of GPC and HPLC are shown below.

GPC Analysis (Molecular Weight Measurement)
  detector: differential refractometer
  column: ultrahydrogel 500 and ultrahydrogel 250 (WATERS)
  mobile phase: 100 mM Acetate buffer+0.02% $NaN_3$ (pH 5.2)
  flow rate: 0.5 mL/min
  sample volume: 5 mg/mL, 20 μL
  column temperature: 30° C.
HPLC Analysis (Amine Purity Measurement)
  detector: differential refractometer
  column: TSKgel SP-5PW (Tosoh Corporation)
  mobile phase: 1 mM Sodium phosphate buffer (pH 6.5)
  flow rate: 0.5 mL/min injection volume: 5 mg/mL, 20 μL
column temperature: 40° C.

Example 1

Synthesis of Compound (p1) (ME-200GLFG (SEQ ID NO: 4) (L)-200PA)

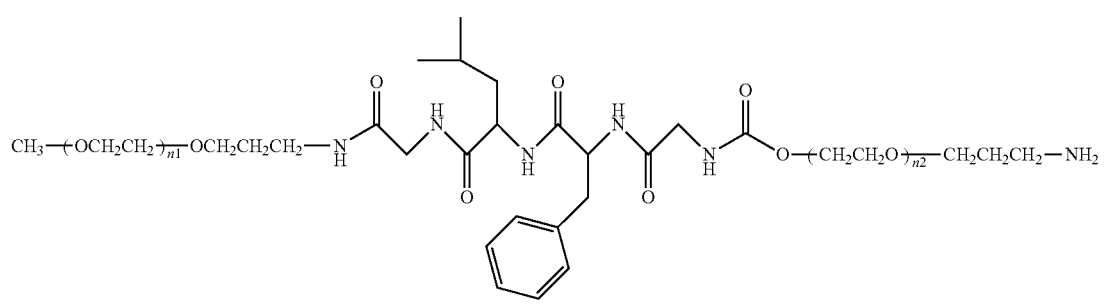

(p1)

n1 = about 480, n2 = about 430

Example 1-1

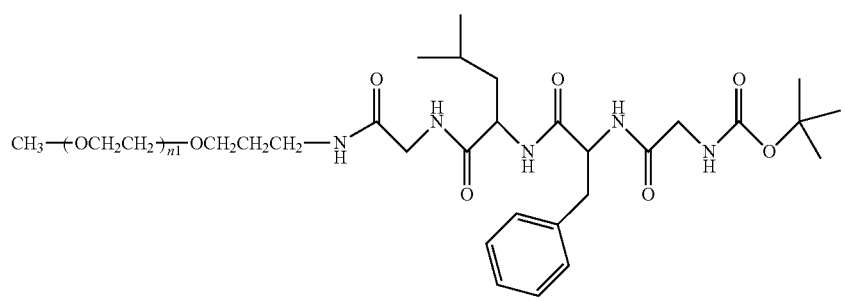

(p2)

n1 = about 480

Glycyl-L-phenylalanyl-L-leucyl-glycine (SEQ ID NO: 4) with N-terminal protected by a tert-butoxycarbonyl group (Boc group) (Boc-Gly-Phe-Leu-Gly (SEQ ID NO: 4)) (0.197 g, $4.0 \times 10^{-4}$ mol, manufactured by GenScript Biotech) and N-hydroxysuccinimide (57.5 mg, $5.0 \times 10^{-4}$ mol, manufactured by Midori Kagaku Co., Ltd.) were dissolved in dehydrated N,N'-dimethylformamide (1.0 g), N,N'-dicyclohexylcarbodiimide (0.103 g, $5.0 \times 10^{-4}$ mol, manufactured by Tama Kagaku Kogyo Co., Ltd.) was added, and the mixture was reacted at room temperature under a nitrogen atmosphere for 1 hr. After diluting with dehydrated N,N'-dimethylformamide (3.0 g), methoxy PEG having a propylamino group at the terminal (2.0 g, $9.5 \times 10^{-5}$ mol, average molecular weight=about 21,000, "SUNBRIGHT MEPA-20T" manufactured by NOF CORPORATION) was added, and the mixture was reacted at room temperature under a nitrogen atmosphere for 1 hr. Thereafter, ethyl acetate (20 g) was added to dilute the reaction mixture, and suction filtration was performed using a Kiriyama funnel lined with LS100 filter paper. Ethyl acetate (30 g) was added to the filtrate, and the mixture was stirred to uniformity, hexane (25 g) was added, and the mixture was stirred at room temperature for 15 min to cause precipitation of the resultant product. Suction filtration was performed using 5A filter paper, the precipitate was recovered, dissolved again in ethyl acetate (50 g), hexane (25 g) was added, and the mixture was stirred at room temperature for 15 min to cause precipitation of the resultant product. Suction filtration was performed using 5A filter paper, the precipitate was recovered and washed with hexane (25 g). Suction filtration was performed using 5A filter paper, and the precipitate was dried in vacuo to give the above-mentioned compound (p2) (ME-200GLFG (SEQ ID NO: 4) (L)-Boc). yield 1.8 g.

NMR (CDCl$_3$): 0.89 ppm (d, 3H, —NH—CO—CH—CH$_2$—CH(CH$_3$)$_2$), 0.92 ppm (d, 3H, —NH—CO—CH—CH$_2$—CH(CH$_3$)$_2$), 1.36 ppm (s, 9H, —NH—CO—O—C(CH$_3$)$_3$), 1.48 ppm (m, 1H, —NH—CO—CH—CH$_2$—CH(CH$_3$)$_2$), 1.55 ppm (m, 1H, —NH—CO—CH-CH$_2$—CH(CH$_3$)$_2$), 1.80 ppm (m, 3H), 3.13 ppm (dd, 1H, —NH—CO—CH—CH$_2$—C$_6$H$_5$), 3.21 ppm (dd, 1H, —NH—CO—CH—CH$_2$—C$_6$H$_5$), 3.33 ppm (m, 2H, —CO—NH—CH$_2$—CH$_2$—CH$_2$—O—(CH$_2$—CH$_2$—O)n-CH$_3$), 3.38 ppm (s, 3H, —CO—NH—CH$_2$—CH$_2$—CH$_2$—O—(CH$_2$—CH$_2$—O)n-CH$_3$), 3.65 ppm (m, about 2,000H, —CO—NH—CH$_2$—CH$_2$—CH$_2$—O—(CH$_2$—CH$_2$—O)n-CH$_3$), 3.91 ppm (t, 1H, —NH—CO—CH—CH$_2$—CH(CH$_3$)$_2$), 4.43 ppm (broad, 1H), 4.55 ppm (q, 1H, —NH—CO—CH—CH$_2$—C$_6$H$_5$), 5.77 ppm (broad, 1H), 6.76 ppm (broad, 1H), 6.86 ppm (broad, 1H), 6.90 ppm (broad, 1H), 7.14 ppm (broad, 1H), 7.20 ppm (d, 2H, —NH—CO—CH—CH$_2$—C$_6$H$_5$), 7.32 ppm (m, 3H, —NH—CO—CH—CH$_2$-C$_6$H$_5$)

Example 1-2

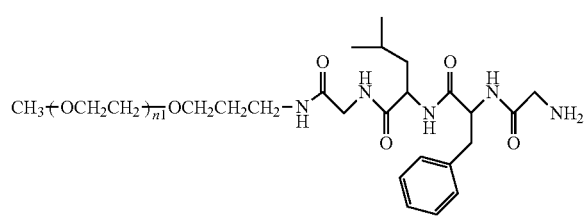

n1 = about 480

ME-200GLFG (SEQ ID NO: 4) (L)-Boc (1.8 g, 8.6×10$^{-5}$ mol) obtained in Example 1-1 was dissolved in dichloromethane (9.0 g), methanesulfonic acid (584 µL, 9.0×10$^{-3}$ mol, manufactured by KANTO CHEMICAL CO., INC.) was added, and the mixture was reacted at room temperature under a nitrogen atmosphere for 2 hr. Thereafter, the reaction mixture was diluted with toluene (18 g), ion exchange water (18 g) was added, and the mixture was stirred at room temperature for 15 min. The resultant product was extracted into the aqueous layer. To the obtained aqueous layer was added an appropriate amount of 1 mol/L aqueous sodium hydroxide solution, the pH was adjusted to 12, and sodium chloride (4.5 g) was dissolved. Chloroform (18 g) was added, and the mixture was stirred at room temperature for 15 min, and the resultant product was extracted into the organic layer. The aqueous layer and the organic layer were separated, chloroform (18 g) was added to the aqueous layer again, and the mixture was stirred at room temperature for 15 min, and the resultant product was extracted into the organic layer. The organic layer obtained by the first and the second extraction was concentrated at 40° C., and ethyl acetate (36 g) was added to the obtained concentrate. Sodium sulfate (0.90 g) was added to the obtained ethyl acetate solution, and the mixture was stirred at 30° C. for 15 min, and suction filtration was performed using a Kiriyama funnel lined with Oplite on 5A filter paper. To the obtained filtrate was added hexane (18 g), and the mixture was stirred at room temperature for 15 min to cause precipitation of the resultant product. Suction filtration was performed using 5A filter paper, and the precipitate was washed with hexane (18 g). Suction filtration was performed using 5A filter paper, and the filtrate was dried in vacuo to give the above-mentioned compound (p3) (ME-200GLFG (SEQ ID NO: 4) (L)-NH$_2$). yield 1.4 g.

NMR (CDCl$_3$): 0.89 ppm (d, 3H, —NH—CO—CH—CH$_2$—CH(CH$_3$)$_2$), 0.91 ppm (d, 3H, —NH—CO—CH—CH$_2$—CH(CH$_3$)$_2$), 1.53 ppm (m, 2H, —NH—CO—CH—CH$_2$—CH(CH$_3$)$_2$), 1, 70 ppm (m, 1H, —NH—CO—CH—CH$_2$—CH(CH$_3$)$_2$), 1.80 ppm (m, 2H, —CO—NH—CH$_2$—CH$_2$—CH$_2$—O—(CH$_2$—CH$_2$—O)n-CH$_3$), 3.10 ppm (dd, 1H, —NH—CO—CH—CH$_2$—C$_6$H$_5$), 3.18 ppm (dd, 1H, —NH—CO—CH—CH$_2$—C$_6$H$_5$), 3.33 ppm (m, 7H), 3.74 ppm (m, about 1,900H, —CO—NH—CH$_2$—CH$_2$—CH$_2$—O—(CH$_2$—CH$_2$—O)n-CH$_3$), 4.31 ppm (broad, 1H), 4.55 ppm (t, 1H, —NH—CO—CH—CH$_2$—C$_6$H$_5$), 6.91 ppm (broad, 1H), 7.00 ppm (broad, 1H), 7.28 ppm (m, 5H, —NH—CO—CH—CH$_2$—C$_6$H$_5$), 7.98 ppm (broad, 1H)

Example 1-3

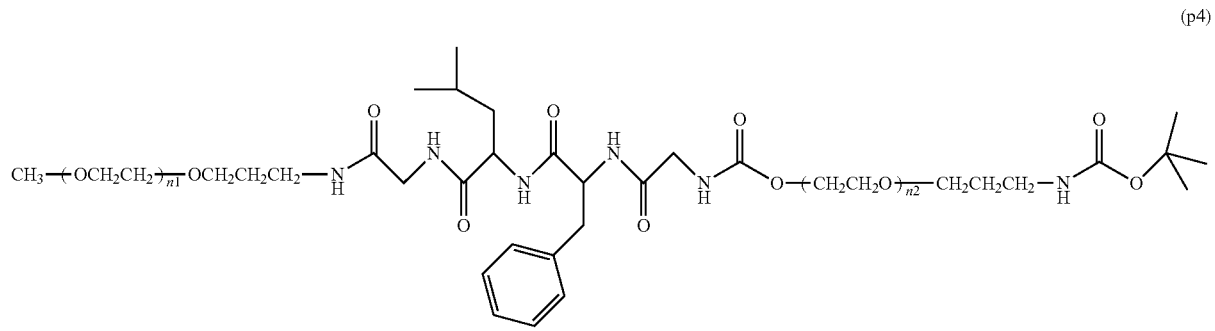

n1 = about 480, n2 = about 430

ME-200GLFG (SEQ ID NO: 4) (L)-NH$_2$ (1.2 g, 5.7×10$^{-5}$ mol) obtained in Example 1-2 was dissolved in chloroform (14.4 g), triethylamine (10 µL, 7.1×10$^{-5}$ mol, KANTO CHEMICAL CO., INC.), and heterobifunctional PEG having a propylamino group protected by a tert-butoxycarbonyl group at one terminal and a carbonate succinimidyl group at the other terminal (1.3 g, 6.2×10$^{-5}$ mol, average molecular weight=about 19,000, "SUNBRIGHT BO-200TS" manufactured by NOF CORPORATION) were added, and the mixture was reacted at room temperature under a nitrogen atmosphere for 2 hr. After the reaction, the mixture was concentrated at 40° C., the obtained concentrate was dissolved in ethyl acetate (48 g), hexane (24 g) was added, and the mixture was stirred at room temperature for 15 min. The resultant product was precipitated and suction filtered using 5A filter paper. The obtained precipitate was dissolved again in ethyl acetate (48 g), hexane (24 g) was added, and the mixture was stirred at room temperature for 15 min. The resultant product was precipitated and suction filtered using 5A filter paper. The precipitate was recovered, washed with hexane (24 g), suction filtered using 5A filter paper, and dried in vacuo to give the above-mentioned compound (p4) (ME-200GLFG (SEQ ID NO: 4) (L)-200Boc). yield 2.0 g.

NMR (CDCl$_3$): 0.90 ppm (t, 6H, —NH—CO—CH—CH$_2$—CH(CH$_3$)$_2$), 1.44 ppm (s, 9H, —CH$_2$—CH$_2$—CH$_2$—

NH—CO—O—C(CH₃)₃), 1.64 ppm (m, 1H), 1.76 ppm (m, 5H), 3.20 ppm (m, 4H), 3.33 ppm (m, 2H, —CO—NH—CH₂—CH₂—CH₂—O—(CH₂—CH₂—O)n-CH₃), 3.38 ppm (s, 3H, —CO—NH—CH₂—CH₂—CH₂—O—(CH₂—CH₂—O)n-CH₃), 3.64 ppm (m, about 3,800H, —NH—CH₂—CH₂—CH₂—O—(CH₂—CH₂—O)n-CH₃, —NH—CO—O—CH₂—CH₂—O—(CH₂—CH₂—O)n-CH₂—CH₂—), 4.10 ppm (m, 2H, —NH—CO—O—CH₂—CH₂—O—(CH₂—CH₂—O)n-CH₂—CH₂—), 4.32 ppm (m, 1H), 4.50 ppm (q, 1H), 5.02 ppm (broad, 1H), 6.45 ppm (broad, 1H), 6.93 ppm (broad, 1H), 7.06 ppm (broad, 1H), 7.13 ppm (broad, 1H), 7.27 ppm (m, 5H, —NH—CO—CH—CH₂—C₆H₅)

Example 1-4

ME-200GLFG (SEQ ID NO: 4) (L)-200Boc (1.8 g, 4.3×10⁻⁵ mol) obtained in Example 1-3 was dissolved in dichloromethane (9.0 g), methanesulfonic acid (292 μL, 4.5×10⁻³ mol, manufactured by KANTO CHEMICAL CO., INC.) was added, and the mixture was reacted at room temperature under a nitrogen atmosphere for 2 hr. Thereafter, the reaction mixture was diluted with toluene (18 g), ion exchange water (18 g) was added, and the mixture was stirred at room temperature for 15 min. The resultant product was extracted into the aqueous layer. According to the conditions described in JP-A-2014-208786, the pH of the aqueous layer was adjusted to 2.0 with 1 mol/L hydrochloric acid, the aqueous layer was washed with a mixed solution of toluene and chloroform, whereby polyethylene glycol impurity without an amino group was removed. Successively, the aqueous layer was adjusted to pH 12 by adding an appropriate amount of 1 mol/L aqueous sodium hydroxide solution, and sodium chloride (4.5 g) was dissolved. Chloroform (18 g) was added thereto, the mixture was stirred at room temperature for 15 min, and the resultant product was extracted into the organic layer. The aqueous layer and the organic layer were separated, chloroform (18 g) was added again to the aqueous layer, and the mixture was stirred at room temperature for 15 min, and the resultant product was extracted into the organic layer. The organic layer obtained by the first and the second extraction was concentrated at 40° C., and ethyl acetate (27 g) was added to the obtained concentrate. Sodium sulfate (0.90 g) was added to the obtained ethyl acetate solution, and the mixture was stirred at 30° C. for 30 min, and suction filtration was performed using a Kiriyama funnel lined with Oplite on 5A filter paper. Hexane (18 g) was added to the obtained filtrate, and the mixture was stirred at room temperature for 15 min. The resultant product was precipitated and suction filtered using 5A filter paper. The precipitate was washed with hexane (18 g), suction filtered using 5A filter paper, and dried in vacuo to give the above-mentioned compound (p1) (ME-200GLFG (SEQ ID NO: 4) (L)-200PA). yield 1.5 g. The molecular weight is shown in Table 1. HPLC: amine purity 91%.

NMR (CDCl₃): 0.90 ppm (t, 6H, —NH—CO—CH—CH₂—CH(CH₃)₂), 1.48 ppm (broad, 1H), 1.62 ppm (t, 1H), 1.71 ppm (m, 1H), 1.82 ppm (m, 2H), 3.12 ppm (m, 2H), 3.19 ppm (d, 2H), 3.34 ppm (m, 2H), 3.38 ppm (s, 3H, —CO—NH—CH₂—CH₂—CH₂—O—(CH₂—CH₂—O)n-CH₃), 3.64 ppm (m, about 3,800H, —NH—CH₂—CH₂—CH₂—O—(CH₂—CH₂—O)n-CH₃, —NH—CO—O—CH₂—CH₂—O—(CH₂—CH₂—O)n-CH₂—CH₂—), 4.10 ppm (m, 2H), 4.34 ppm (m, 1H), 4.50 ppm (q, 1H), 6.46 ppm (broad, 1H), 6.94 ppm (broad, 1H), 7.08 ppm (broad, 1H), 7.27 ppm (m, 5H, —NH—CO—CH—CH₂—C₆H₅)

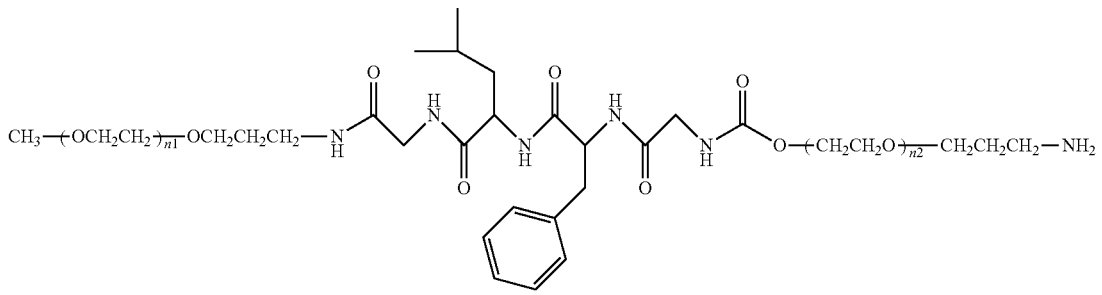

(p1)

n1 = about 480, n2 = about 430

Example 2

Synthesis of Compound (p5) (ME-200GLFG (SEQ ID NO: 4) (L)-200AL)

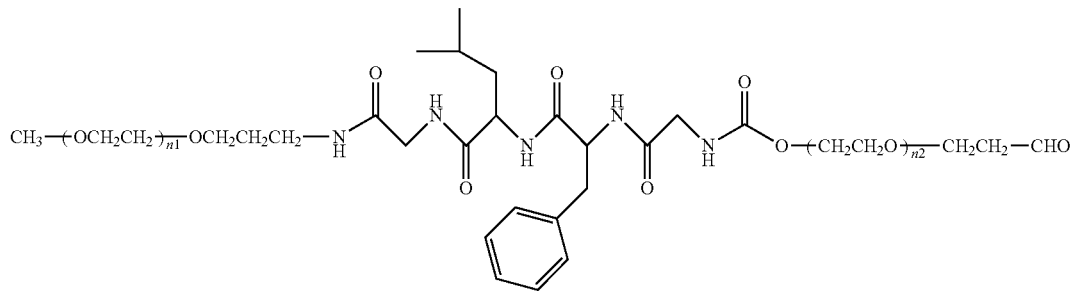

(p5)

n1 = about 480, n2 = about 450

Example 2-1

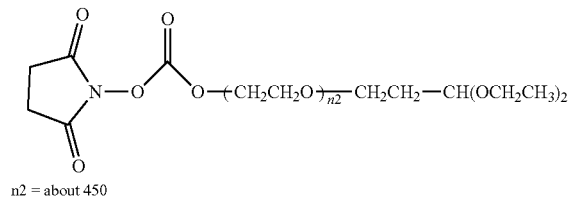

(p6)

n2 = about 450

Heterobifunctional PEG having a 3,3-diethoxypropyl group at one terminal and a hydroxyl group at one terminal (15.0 g, $7.5 \times 10^{-4}$ mol, average molecular weight=about 20,000) synthesized using the production method described in JP-B-3508207 and the like was dissolved in dehydrated dichloromethane (75 g), N,N'-disuccinimidyl carbonate (1.2 g, $4.7 \times 10^{-3}$ mol, manufactured by Tokyo Chemical Industry Co., Ltd.) and triethylamine (836 μL, $6.0 \times 10^{-3}$ mol, KANTO CHEMICAL CO., INC.) were added, and the mixture was reacted at room temperature under a nitrogen atmosphere for 5 hr. After suction filtration using 5A filter paper, the filtrate was concentrated at 40° C., ethyl acetate (150 g) and 2,6-di-tert-butyl-p-cresol (30 mg) were added to the obtained concentrate and the mixture was stirred to uniformity. Hexane (75 g) was added, and the mixture was stirred at room temperature for 15 min. The resultant product was precipitated and suction filtered using 5A filter paper. The precipitate was recovered and dissolved again in ethyl acetate (150 g) and 2,6-di-tert-butyl-p-cresol (30 mg). Hexane (75 g) was added, and the mixture was stirred at room temperature for 15 min. The resultant product was precipitated and suction filtered using 5A filter paper. A similar operation was performed 4 times, and the obtained precipitate was washed with hexane (90 g). After suction filtration using 5A filter paper, the precipitate was dried in vacuo to give the above-mentioned compound (p6). yield 11.8 g.

NMR (CDCl$_3$): 1.20 ppm (t, 6H, —CH$_2$—CH$_2$—CH(OCH$_2$CH$_3$)$_2$), 1.90 ppm (q, 2H, —CH$_2$—CH$_2$—CH(OCH$_2$CH$_3$)$_2$), 2.84 ppm (s, 4H, —O—CO—O—NC$_4$H$_4$O$_2$), 3.65 ppm (m, about 1,900H, —O—CO—O—CH$_2$—CH$_2$—O—(CH$_2$CH$_2$O)n-CH$_2$—), 4.46 ppm (t, 2H, —O—CO—O—CH$_2$—CH$_2$—O—(CH$_2$CH$_2$O)n-CH$_2$—), 4.64 ppm (t, 1H, —CH$_2$—CH$_2$—CH(OCH$_2$CH$_3$)$_2$)

Example 2-2

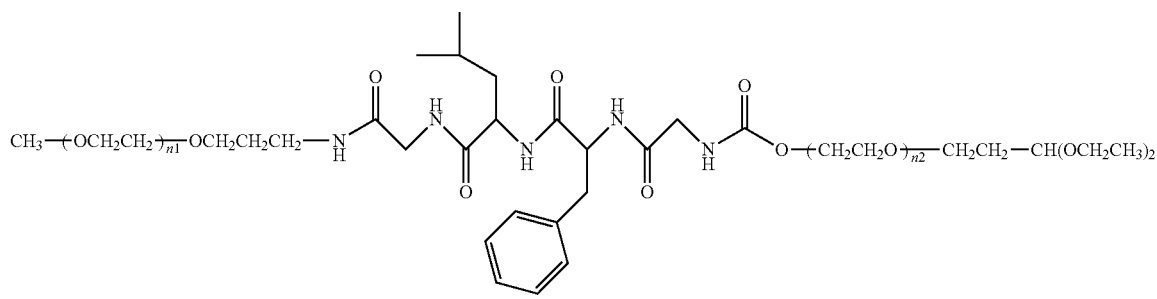

(p7)

n1 = about 480, n2 = about 450

ME-200GLFG (SEQ ID NO: 4) (L)-NH$_2$ (1.9 g, $9.0 \times 10^{-5}$ mol) obtained in Example 1-2 was dissolved in chloroform (18 g), triethylamine (13 μL, $9.3 \times 10^{-5}$ mol, KANTO CHEMICAL CO., INC.) and succinimidyl group-PEG-3,3-diethoxypropyl group (1.5 g, $7.5 \times 10^{-5}$ mol, average molecular weight=about 21,000) obtained in Example 2-1 were added, and the mixture was reacted at room temperature under a nitrogen atmosphere for 2 hr. After the reaction, the mixture was concentrated at 40° C. and, according to the conditions described in JP-A-2011-79934, the obtained concentrate was dissolved in a mixed solution of toluene and chloroform, the organic layer was washed with 5% brine, and polyethylene glycol impurity with a molecular weight of about 21,000 was removed. The organic layer was concentrated at 40° C., the obtained concentrate was dissolved in ethyl acetate (60 g), hexane (30 g) was added and the mixture was stirred at room temperature for 15 min. The resultant product was precipitated and suction filtered using 5A filter paper. The obtained precipitate was dissolved again in ethyl acetate (60 g), hexane (30 g) was added, and the mixture was stirred at room temperature for 15 min. The resultant product was precipitated and suction filtered using 5A filter paper. The precipitate was recovered, washed with hexane (30 g), suction filtered using 5A filter paper, and dried in vacuo to give the above-mentioned compound (p7) (ME-200GLFG (SEQ ID NO: 4) (L)-200DE). yield 3.1 g.

NMR (CDCl$_3$): 0.90 ppm (t, 6H, —NH—CO—CH—CH$_2$—CH(C$\underline{H}_3$)$_2$), 1.20 ppm (t, 6H, —CH$_2$—CH$_2$—CH(OCH$_2$C$\underline{H}_3$)$_2$), 1.47 ppm (m, 1H, —NH—CO—CH—C$\underline{H}_2$—CH(CH$_3$)$_2$), 1.61 ppm (m, 1H, —NH—CO—CH—C$\underline{H}_2$—CH(CH$_3$)$_2$), 1.72 ppm (m, 1H), 1.82 ppm (m, 2H), 1.90 ppm (q, 2H, —CH$_2$—C$\underline{H}_2$—CH(OCH$_2$CH$_3$)$_2$), 2.58 ppm (m, 1H), 3.19 ppm (d, 2$\overline{H}$, —NH—CO—CH—C$\underline{H}_2$—C$_6$H$_5$), 3.33 ppm (m, 2H, —CO—NH—C$\underline{H}_2$—$\overline{CH}_2$—CH$_2$—O—(CH$_2$—CH$_2$—O)n-CH$_3$), 3.38 ppm (—CO—NH—CH$_2$—CH$_2$—CH$_2$—O—(CH$_2$—CH$_2$—O)n-C$\underline{H}_3$), 4.29 ppm (m, 1H), 4.50 ppm (q, 1H), 4.64 ppm (t, 1H, —CH$_2$—CH$_2$—C$\underline{H}$(OCH$_2$CH$_3$)$_2$), 6.38 ppm (broad, 1H), 6.89 ppm (broad, 1H), 6.99 ppm (broad, 1H), 7.10 ppm (broad, 1H), 7.29 ppm (m, 5H)

Example 2-3 dropwise to the obtained solution to adjust the pH to 7.05, chloroform (15 g) in which 2,6-di-tert-butyl-p-cresol (1.5 mg) was dissolved in advance was added, and the mixture was stirred at room temperature for 20 min. The resultant product was extracted into the organic layer. The organic layer and the aqueous layer were separated, and the organic layer was recovered. Chloroform (15 g) in which 2,6-di-tert-butyl-p-cresol (1.5 mg) was dissolved in advance was added again to the aqueous layer, and the mixture was stirred at room temperature for 20 min. The resultant product was extracted into the organic layer. The organic layer obtained by the first and the second extraction was concentrated at 50° C., and ethyl acetate (10 g) was added to the obtained concentrate, and the mixture was stirred to uniformity. Magnesium sulfate (0.25 g) was added, and the mixture was stirred at 30° C. for 15 min, and suction filtration was performed using a Kiriyama funnel lined with Oplite on 5A filter paper, followed by washing with ethyl acetate (10 g). Hexane (15 g) was added to the obtained filtrate, the mixture was stirred at room temperature for 15 min. The resultant product was precipitated and suction filtered using 5A filter paper. The precipitate was washed with hexane (10 g) in which 2,6-di-tert-butyl-p-cresol (1.0 mg) was dissolved in advance, suction filtered using 5A filter paper, and dried in vacuo to give the above-mentioned compound (p5) (ME-200GLFG (SEQ ID NO: 4) (L)-200AL). yield 0.65 g. The molecular weight is shown in Table 1. The aldehyde purity was 86% ($^1$H-NMR).

NMR (CDCl$_3$): 0.90 ppm (t, 6H, —NH—CO—CH—CH$_2$—CH(C$\underline{H}_3$)$_2$), 1.47 ppm (m, 1H, —NH—CO—CH—C$\underline{H}_2$—CH(CH$_3$)$_2$), 1.61 ppm (m, 1H, —NH—CO—CH—C$\underline{H}_2$—CH(CH$_3$)$_2$), 1.72 ppm (m, 1H), 1.84 ppm (m, 5H), 2.68 ppm (m, 2H), 3.19 ppm (d, 2H, —NH—CO—CH—C$\underline{H}_2$—C$_6$H$_5$), 3.33 ppm (m, 2H, —CO—NH—C$\underline{H}_2$—$\overline{CH}_2$—CH$_2$—O—(CH$_2$—CH$_2$—O)n-CH$_3$), 3.38 ppm (—CO—NH—CH$_2$—CH$_2$—CH$_2$—O—(CH$_2$—CH$_2$—O)n-C$\underline{H}_3$), 4.06 ppm (m, 1H, —NH—CO—O—C$\underline{H}_2$—CH$_2$—O—(CH$_2$CH$_2$O)n-CH$_2$CH$_2$—), 4.12 ppm (m, 1H, —NH—CO—O—C$\underline{H}_2$—CH$_2$—O—(CH$_2$CH$_2$O)n-CH$_2$CH$_2$—), 4.32 ppm (m, 1H), 4.51 ppm (q, 1H), 6.36 ppm (broad, 1H), 6.87 ppm (broad, 1H), 6.99 ppm (broad, 2H), 7.14 ppm (broad, 1H), 7.29 ppm (m, 5H), 9.80 ppm (s, 1H, —CH$_2$CH$_2$—C$\underline{H}$O)

(p5)

CH$_3$—(OCH$_2$CH$_2$)$_{\overline{n1}}$OCH$_2$CH$_2$CH$_2$—NH—CH$_2$—CO—NH—CH(CH$_2$CH(CH$_3$)$_2$)—CO—NH—CH(CH$_2$C$_6$H$_5$)—CO—NH—CH$_2$—CO—NH—O—(CH$_2$CH$_2$O)$_{\overline{n2}}$—CH$_2$CH$_2$—CHO n1 = about 480, n2 = about 450

ME-200GLFG (SEQ ID NO: 4) (L)-200DE (1.0 g, 2.4×10$^{-5}$ mol) obtained in Example 2-2 was dissolved in injectable distilled water (20 g), the pH was adjusted to 1.50 with 85% phosphoric acid (0.46 g), and the mixture was reacted at 20-25° C. for 2 hr. After the reaction, 400 g/L aqueous sodium hydroxide solution (0.69 g) was added to adjust the pH to 6.70, and sodium chloride (4.0 g) was dissolved. 1 M aqueous sodium hydroxide solution (1.76 g) was added

Example 3

Synthesis of Compound (p8) (ME-100GLFG (SEQ ID NO: 4) (L)-100GLFG (SEQ ID NO: 4) (L)-100GLFG (SEQ ID NO: 4) (L)-100PA)

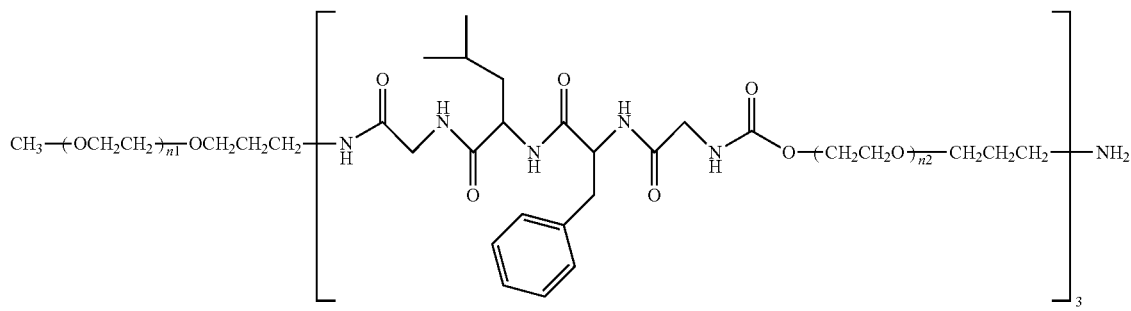

n1 = about 230, n2 = about 230

Example 3-1

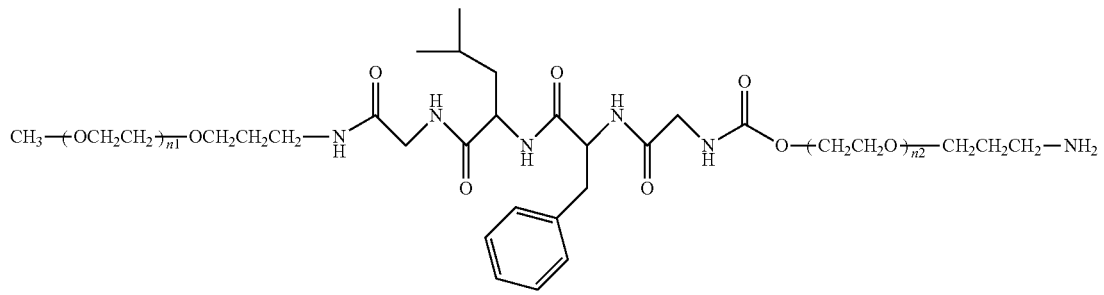

n1 = about 230, n2 = about 230

By the same production method as in Example 1 and using glycyl-L-phenylalanyl-L-leucyl-glycine (SEQ ID NO: 4) with the N terminal protected by a tert-butoxycarbonyl group (Boc group) (Boc-Gly-Phe-Leu-Gly (SEQ ID NO: 4)), methoxy PEG having a propylamino group at the terminal (average molecular weight=about 10,000, "SUN-BRIGHT MEPA-10T" manufactured by NOF CORPORATION), and heterobifunctional PEG having a propylamino group protected by a tert-butoxycarbonyl group at one terminal and a carbonate succinimidyl group at the other terminal (average molecular weight=about 10,000, "SUN-BRIGHT BO-100TS" manufactured by NOF CORPORATION) as starting materials, the above-mentioned compound (p9) (ME-100GLFG (SEQ ID NO: 4) (L)-100PA) was obtained. yield 1.0 g.

NMR (CDCl$_3$): 0.90 ppm (t, 6H, —NH—CO—CH—CH$_2$—CH(C$\underline{H_3}$)$_2$), 1.48 ppm (broad, 1H), 1.62 ppm (t, 1H), 1.71 ppm (m, 1H), 1.82 ppm (m, 2H), 3.12 ppm (m, 2H), 3.19 ppm (d, 2H), 3.34 ppm (m, 2H), 3.38 ppm (s, 3H, —CO—NH—CH$_2$—CH$_2$—CH$_2$—O—(CH$_2$—CH$_2$—O)n-C$\underline{H_3}$), 3.64 ppm (m, about 1,800H, —NH—CH$_2$—CH$_2$—CH$_2$—O—(C$\underline{H_2}$—C$\underline{H_2}$—O)n-CH$_3$, —NH—CO—O—CH$_2$—CH$_2$—O—(C$\underline{H_2}$—C$\underline{H_2}$—O)n-CH$_2$—CH$_2$—), 4.10 ppm (m, 2H), 4.34 ppm (m, 1H), 4.50 ppm (q, 1H), 6.46 ppm (broad, 1H), 6.94 ppm (broad, 1H), 7.08 ppm (broad, 1H), 7.27 ppm (m, 5H, —NH—CO—CH—CH$_2$—C$\underline{_6H_5}$)

Example 3-2

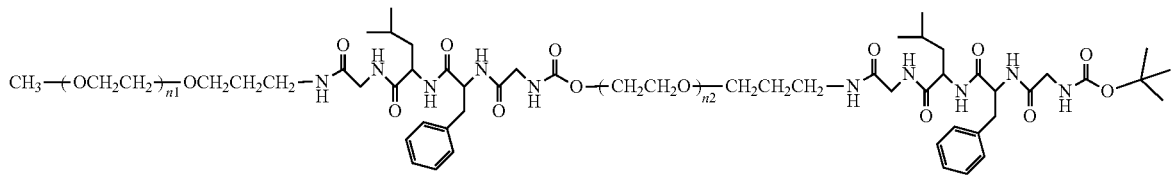

n1 = about 230, n2 = about 230

To ME-100GLFG (SEQ ID NO: 4) (L)-100PA (1.0 g, $5.0 \times 10^{-5}$ mol) obtained in Example 3-1 and Boc-Gly-Phe-Leu-Gly (SEQ ID NO: 4) (0.99 g, $2.0 \times 10^{-4}$ mol, manufactured by GenScript Biotech) was added dehydrated N,N'-dimethylformamide (10 g), and the mixture was dissolved by heating at 30° C. Thereafter, diisopropylethylamine (65 μL, $3.8 \times 10^{-4}$ mol, manufactured by KANTO CHEMICAL CO., INC.) and (1-cyano-2-ethoxy-2-oxoethylideneaminooxy)dimethylamino-morpholino-carbenium hexafluorophosphate (COMU) (0.106 g, $2.5 \times 10^{-4}$ mol, manufactured by Sigma Ltd. Aldrich) were added, and the mixture was reacted at room temperature under a nitrogen atmosphere for 1 hr. After completion of the reaction, the mixture was diluted with chloroform (100 g), saturated aqueous sodium hydrogen carbonate solution (50 g) was added, and the mixture was stirred at room temperature for 15 min for washing. The aqueous layer and the organic layer were separated, saturated aqueous sodium hydrogen carbonate solution (50 g) was added again to the organic layer, the mixture was stirred at room temperature for 15 min for washing, and the organic layer was recovered. Magnesium sulfate (1.0 g) was added to the obtained organic layer, and the mixture was stirred for 30 min for dehydration, and suction filtration was performed using a Kiriyama funnel lined with Oplite on 5A filter paper. The obtained filtrate was concentrated at 40° C., ethyl acetate (50 g) was added to the concentrate and the mixture was stirred to uniformity. Hexane (25 g) was added, and the mixture was stirred at room temperature for 15 min. The resultant product was precipitated and suction filtered using 5A filter paper. The precipitate was recovered, dissolved again in ethyl acetate (50 g). Hexane (25 g) was added at room temperature, and the mixture was stirred at room temperature for 15 min. The resultant product was precipitated and suction filtered using 5A filter paper. The precipitate was recovered, washed with hexane (25 g), suction filtered using 5A filter paper, and dried in vacuo to give the above-mentioned compound (p10) (ME-100GLFG (SEQ ID NO: 4) (L)-100GLFG (SEQ ID NO: 4) (L)-Boc). yield 0.9 g.

NMR (CDCl$_3$): 0.90 ppm (t, 12H, —NH—CO—CH—CH$_2$—CH(CH$_3$)$_2$), 1.44 ppm (s, 9H, —CH$_2$—CH$_2$—CH$_2$—NH—CO—O—C(CH$_3$)$_3$), 1.64 ppm (m, 2H), 1.76 ppm (m, 5H), 3.20 ppm (m, 4H), 3.33 ppm (m, 4H, —CO—NH—CH$_2$—CH$_2$—CH$_2$—O—(CH$_2$—CH$_2$—O)n-), 3.38 ppm (s, 3H, —O—(CH$_2$—CH$_2$—O)n-CH$_3$), 3.64 ppm (m, about 1,800H, —O—(CH$_2$—CH$_2$—O)n-CH$_3$, —NH—CO—O—CH$_2$—CH$_2$—O—(CH$_2$—CH$_2$—O)n-CH$_2$—CH$_2$—), 4.10 ppm (m, 2H, —NH—CO—O—CH$_2$—CH$_2$—O—(CH$_2$—CH$_2$—O)n-CH$_2$—CH$_2$—), 4.32 ppm (m, 2H), 4.50 ppm (q, 2H), 5.02 ppm (broad, 2H), 6.45 ppm (broad, 2H), 6.93 ppm (broad, 2H), 7.06 ppm (broad, 2H), 7.13 ppm (broad, 2H), 7.27 ppm (m, 10H, —NH—CO—CH—CH$_2$—C$_6$H$_5$)

Example 3-3

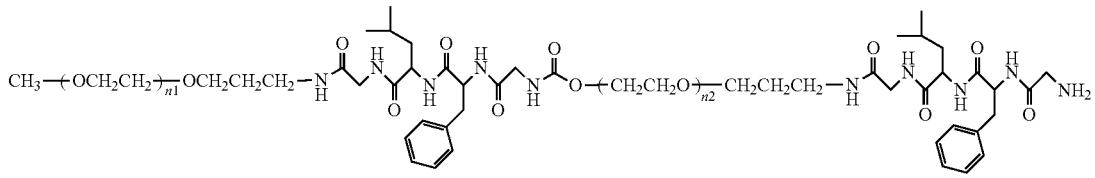

n1 = about 230, n2 = about 230

By the same production method as in Example 1-2, ME-100GLFG (SEQ ID NO: 4) (L)-100GLFG (SEQ ID NO: 4) (L)-Boc (0.9 g, $4.5 \times 10^{-5}$ mol) obtained in Example 3-2 was subjected to deprotection of Boc group to give the above-mentioned compound (p11) (ME-100GLFG (SEQ ID NO: 4) (L)-100GLFG (SEQ ID NO: 4) (L)-NH$_2$). yield 0.8 g.

NMR (CDCl$_3$): 0.89 ppm (d, 6H, —NH—CO—CH—CH$_2$—CH(CH$_3$)$_2$), 0.91 ppm (d, 6H, —NH—CO—CH—CH$_2$—CH(CH$_3$)$_2$), 1.53 ppm (m, 4H, —NH—CO—CH—CH$_2$—CH(CH$_3$)$_2$), 1, 70 ppm (m, 2H, —NH—CO—CH—CH$_2$—CH(CH$_3$)$_2$), 1.80 ppm (m, 4H, —CO—NH—CH$_2$—CH$_2$—CH$_2$—O—(CH$_2$—CH$_2$—O)n-), 3.10 ppm (dd, 2H, —NH—CO—CH—CH$_2$—C$_6$H$_5$), 3.18 ppm (dd, 2H, —NH—CO—CH—CH$_2$—C$_6$H$_5$), 3.33 ppm (m, 14H), 3.74 ppm (m, about 1,800H, —CO—NH—CH$_2$—CH$_2$—CH$_2$—O—(CH$_2$—CH$_2$—O)n-), 4.31 ppm (broad, 2H), 4.55 ppm (t, 2H, —NH—CO—CH—CH$_2$—C$_6$H$_5$), 6.91 ppm (broad, 2H), 7.00 ppm (broad, 2H), 7.28 ppm (m, 10H, —NH—CO—CH—CH$_2$—C$_6$H$_5$), 7.98 ppm (broad, 2H)

Example 3-4

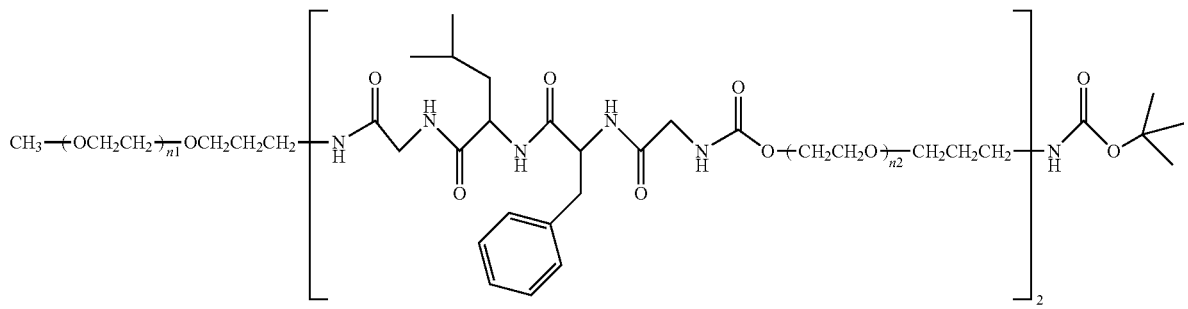

n1 = about 230, n2 = about 230

By the same production method as in Example 1-3, ME-100GLFG (SEQ ID NO: 4) (L)-100GLFG (SEQ ID NO: 4) (L)-NH$_2$ (0.8 g, 4.0×10$^{-5}$ mol) obtained in Example 3-3 was reacted with heterobifunctional PEG having a propylamino group protected by a tert-butoxycarbonyl group at one terminal and a carbonate succinimidyl group at the other terminal (average molecular weight=about 10,000, "SUNBRIGHT BO-100TS" manufactured by NOF CORPORATION) to give the above-mentioned compound (p12) (ME-100GLFG (SEQ ID NO: 4) (L)-100GLFG (SEQ ID NO: 4) (L)-100Boc). yield 1.0 g.

NMR (CDCl$_3$): 0.90 ppm (t, 12H, —NH—CO—CH—CH$_2$—CH(CH$_3$)$_2$), 1.44 ppm (s, 9H, —CH$_2$—CH$_2$—CH$_2$—NH—CO—O—C(CH$_3$)$_3$), 1.64 ppm (m, 2H), 1.76 ppm (m, 10H), 3.20 ppm (m, 8H), 3.33 ppm (m, 6H, —CO—NH—CH$_2$—CH$_2$—CH$_2$—O—(CH$_2$—CH$_2$—O)n-), 3.38 ppm (s, 3H, —(CH$_2$—CH$_2$—O)n-CH$_3$), 3.64 ppm (m, about 2,700H, —NH—CH$_2$—CH$_2$—CH$_2$—O—(CH$_2$—CH$_2$—O)n-CH$_3$, —NH—CO—O—CH$_2$—CH$_2$—O—(CH$_2$—CH$_2$—O)n-CH$_2$—CH$_2$—), 4.10 ppm (m, 4H, —NH—CO—O—CH$_2$—CH$_2$—O—(CH$_2$—CH$_2$—O)n-CH$_2$—CH$_2$—), 4.32 ppm (m, 2H), 4.50 ppm (q, 2H), 5.02 ppm (broad, 2H), 6.45 ppm (broad, 2H), 6.93 ppm (broad, 2H), 7.06 ppm (broad, 2H), 7.13 ppm (broad, 2H), 7.27 ppm (m, 10H, —NH—CO—CH—CH$_2$—C$_6$H$_5$)

Example 3-5

By the same production method as in Example 1-4, ME-100GLFG (SEQ ID NO: 4) (L)-100GLFG (SEQ ID NO: 4) (L)-100Boc (1.0 g, 3.3×10$^{-5}$ mol) obtained in Example 3-4 was subjected to deprotection of Boc group. The obtained crude product was purified by ion exchange chromatography filled with SP Sepharose FF (manufactured by GE Healthcare) as cation exchange resin to give the above-mentioned compound (p13) (ME-100GLFG (SEQ ID NO: 4) (L)-100GLFG (SEQ ID NO: 4) (L)-100PA). yield 0.8 g.

NMR (CDCl$_3$): 0.90 ppm (t, 12H, —NH—CO—CH—CH$_2$—CH(CH$_3$)$_2$), 1.48 ppm (broad, 2H), 1.62 ppm (t, 2H), 1.71 ppm (m, 2H), 1.82 ppm (m, 4H), 3.12 ppm (m, 4H), 3.19 ppm (d, 4H), 3.34 ppm (m, 4H), 3.38 ppm (s, 3H, —O—(CH$_2$—CH$_2$—O)n-CH$_3$), 3.64 ppm (m, about 2,700H, —NH—CH$_2$—CH$_2$—CH$_2$—O—(CH$_2$—CH$_2$—O)n-CH$_3$, —NH—CO—O—CH$_2$—CH$_2$—O—(CH$_2$—CH$_2$—O)n-CH$_2$—CH$_2$—), 4.10 ppm (m, 4H), 4.34 ppm (m, 2H), 4.50 ppm (q, 2H), 6.46 ppm (broad, 2H), 6.94 ppm (broad, 2H), 7.08 ppm (broad, 2H), 7.27 ppm (m, 10H, —NH—CO—CH—CH$_2$—C$_6$H$_5$)

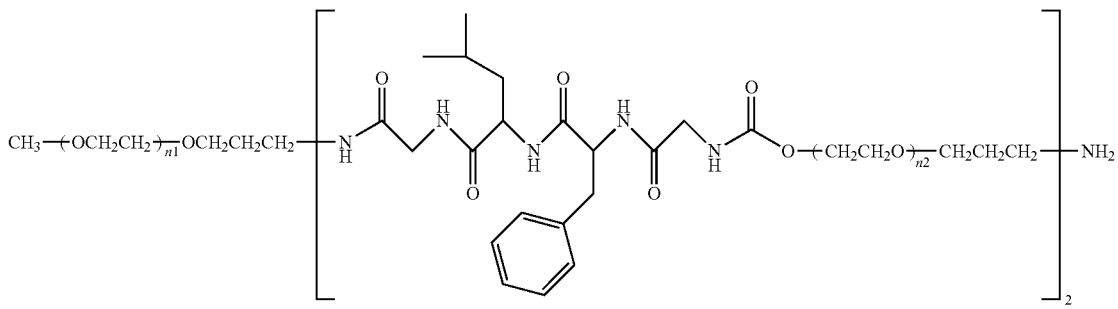

n1 = about 230, n2 = about 230

Example 3-6

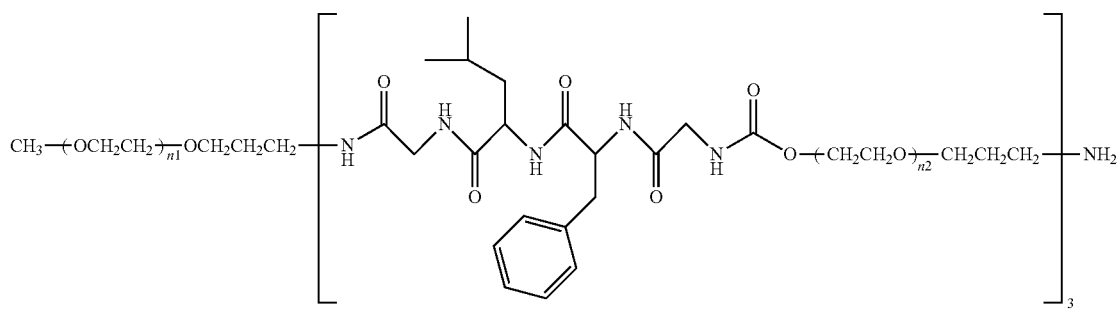

n1 = about 230, n2 = about 230

Using ME-100GLFG (SEQ ID NO: 4) (L)-100GLFG (SEQ ID NO: 4) (L)-100PA (0.8 g, 2.7×10$^{-5}$ mol) obtained in Example 3-5 as a starting material, the reaction was repeated in the order of Example 3-2, Example 3-3, Example 3-4, Example 3-5 by the same production methods to give the above-mentioned compound (p8) (ME-100GLFG (SEQ ID NO: 4) (L)-100GLFG (SEQ ID NO: 4) (L)-100GLFG (SEQ ID NO: 4) (L)-100PA). yield 0.4 g. The molecular weight is shown in Table 1. HPLC: amine purity 90%.

NMR (CDCl$_3$): 0.90 ppm (t, 18H, —NH—CO—CH—CH$_2$—CH(CH$_3$)$_2$), 1.48 ppm (broad, 3H), 1.62 ppm (t, 3H), 1.71 ppm (m, 3H), 1.82 ppm (m, 6H), 3.12 ppm (m, 6H), 3.19 ppm (d, 6H), 3.34 ppm (m, 6H), 3.38 ppm (s, 3H, —O—(CH$_2$—CH$_2$—O)n-CH$_3$), 3.64 ppm (m, about 3,600H, —O—(CH$_2$—CH$_2$—O)n-CH$_3$, —NH—CO—O—CH$_2$—CH$_2$—O—(CH$_2$—CH$_2$—O)n-CH$_2$—CH$_2$—), 4.10 ppm (m, 8H), 4.34 ppm (m, 3H), 4.50 ppm (q, 3H), 6.46 ppm (broad, 3H), 6.94 ppm (broad, 3H), 7.08 ppm (broad, 3H), 7.27 ppm (m, 15H, —NH—CO—CH—CH$_2$—C$_6$H$_5$)

Example 4

Synthesis of Compound (p14) (ME-200G(Cit)V-200PA)

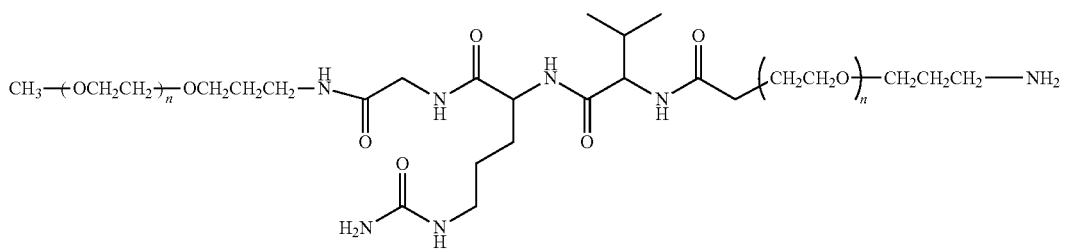

n1 = about 480, n2 = about 520

Example 4-1

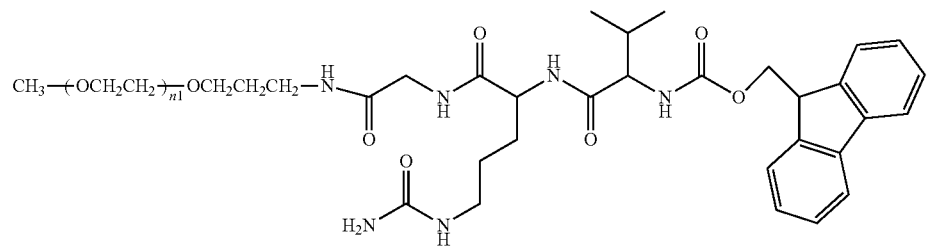

n1 = about 480

To L-valyl-L-citrullyl-glycine with the N terminal protected by a 9-fluorenylmethyloxycarbonyl group (Fmoc group) (Fmoc-Val-(Cit)-Gly) (0.299 g, $5.4 \times 10^{-4}$ mol, manufactured by GenScript Biotech) and methoxy PEG having a propylamino group at the terminal (2.7 g, $1.3 \times 10^{-4}$ mol, average molecular weight=about 21,000, "SUNBRIGHT MEPA-20T" manufactured by NOF CORPORATION) was added dehydrated N,N'-dimethylformamide (27 g), and the mixture was dissolved by heating at 30° C. Thereafter, diisopropylethylamine (172 μL, $1.0 \times 10^{-3}$ mol, manufactured by KANTO CHEMICAL CO., INC.) and (1-cyano-2-ethoxy-2-oxoethylideneaminooxy)dimethylamino-morpholino-carbenium hexafluorophosphate (COMU) (0.289 g, 6.810-4 mol, manufactured by Sigma Ltd. Aldrich) were added, and the mixture was reacted at room temperature under a nitrogen atmosphere for 1 hr. After completion of the reaction, the mixture was diluted with chloroform (270 g), saturated aqueous sodium hydrogen carbonate solution (108 g) was added, and the mixture was stirred at room temperature for 15 min for washing. The aqueous layer and the organic layer were separated, saturated aqueous sodium hydrogen carbonate solution (108 g) was added again to the organic layer, the mixture was stirred at room temperature for 15 min for washing, and the organic layer was recovered. Magnesium sulfate (2.7 g) was added to the obtained organic layer, and the mixture was stirred for 30 min for dehydration, and suction filtration was performed using a Kiriyama funnel lined with Oplite on 5A filter paper. The obtained filtrate was concentrated at 40° C., ethyl acetate (108 g) was added to the concentrate and the mixture was stirred to uniformity. Hexane (54 g) was added, and the mixture was stirred at room temperature for 15 min. The resultant product was precipitated and suction filtered using 5A filter paper. The precipitate was recovered, dissolved again in ethyl acetate (108 g), hexane (54 g) was added at room temperature, and the mixture was stirred at room temperature for 15 min. The resultant product was precipitated and suction filtered using 5A filter paper. The precipitate was recovered, washed with hexane (54 g), suction filtered using 5A filter paper, and dried in vacuo to give the above-mentioned compound (p15) (ME-200G(Cit)V-Fmoc). yield 2.3 g.

NMR ($d_6$-DMSO): 0.84 ppm (d, 3H, —NH—CO—CH—CH(C$\underline{H_3}$)$_2$), 0.85 ppm (d, 3H, —NH—CO—CH—CH (C$\underline{H_3}$)$_2$), 1.37 ppm (m, 2H), 1.52 ppm (m, 1H), 1.63 ppm (m, 3H), 1.98 ppm (m, 1H, —O—CO—NH—CH—C$\underline{H}$(CH$_3$)$_2$), 2.93 ppm (m, 4H), 3.09 ppm (m, 2H, —NH—C$\overline{H}$—CH$_2$—CH$_2$—C$\overline{H_2}$—NH—CO—N$\underline{H_2}$), 3.24 ppm (s, 3H, —N$\underline{H}$—CH$_2$—C$\overline{H_2}$—CH$_2$—O—(CH$_2$—CH$_2$—O)n-C$\underline{H_3}$), 3.48 ppm (m, about 1,900H, —NH—CH$_2$—C$\overline{H_2}$—CH$_2$—O—(C$\underline{H_2}$—C$\underline{H_2}$—O)n-CH$_3$), 3.89 ppm (m, 2H), 4.25 ppm (m, 3H, —N$\overline{H}$—CO—O—CH$_2$—C$\underline{H}$<), 5.35 ppm (broad, 2H, —NH—CH—CH$_2$—C$\overline{H_2}$—C$\overline{H_2}$—NH—CO—N$\underline{H_2}$), 5.91 ppm (broad, 1H), 7.33 ppm (t, 2H, Ar), 7.41 ppm (m, 3H, Ar), 7.73 ppm (m, 3H, Ar), 7.89 ppm (d, 2H, Ar), 8.10 ppm (d, 1H), 8.20 ppm (broad, 1H)

Example 4-2

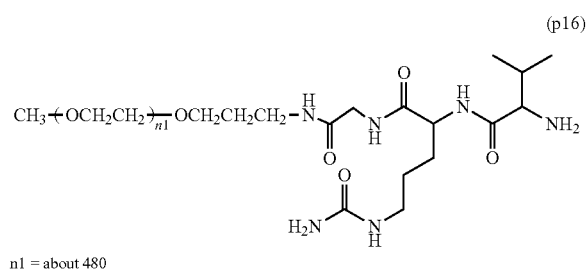

(p16)

n1 = about 480

To ME-200G(Cit)V-Fmoc (2.1 g, $1.0 \times 10^{-4}$ mol) obtained in Example 4-1 was added N,N'-dimethylformamide (12.6 g), and the mixture was dissolved by heating at 30° C. Piperidine (0.66 g, $7.8 \times 10^{-3}$ mol, manufactured by Wako Pure Chemical Industries, Ltd.) was added, and the mixture was reacted at room temperature under a nitrogen atmosphere for 2 hr. After completion of the reaction, ethyl acetate (150 g) was added, and the mixture was stirred to uniformity. Hexane (75 g) was added, and the mixture was stirred at room temperature for 15 min. The resultant product was precipitated and suction filtered using 5A filter paper. The precipitate was recovered, dissolved again in ethyl acetate (150 g), hexane (75 g) was added, and the mixture was stirred at room temperature for 15 min. The resultant product was precipitated and suction filtered using 5A filter paper. The precipitate was recovered, washed with hexane (75 g), suction filtered using 5A filter paper, and dried in vacuo to give the above-mentioned compound (p16) (ME-200G(Cit)V-N$\underline{H_2}$). yield 1.8 g.

NMR ($d_6$-DMSO): 0.77 ppm (d, 3H, —NH—CO—CH—CH(C$\underline{H_3}$)$_2$), 0.87 ppm (d, 3H, —NH—CO—CH—CH (C$\underline{H_3}$)$_2$), 1.35 ppm (m, 2H), 1.51 ppm (m, 1H), 1.64 ppm (m, 4H), 1.93 ppm (m, 1H, —O—CO—NH—CH—C$\underline{H}$(CH$_3$)$_2$), 2.96 ppm (m, 4H), 3.10 ppm (m, 2H, —NH—C$\overline{H}$—CH$_2$—CH$_2$—C$\overline{H_2}$—NH—CO—N$\underline{H_2}$), 3.24 ppm (s, 3H, —N$\underline{H}$—CH$_2$—C$\overline{H_2}$—CH$_2$—O—(CH$_2$—CH$_2$—O)n-C$\underline{H_3}$), 3.48 ppm (m, about 1,900H, —NH—CH$_2$—C$\overline{H_2}$—CH$_2$—O—(C$\underline{H_2}$—C$\underline{H_2}$—O)n-CH$_3$), 4.21 ppm (broad, 1H), 5.34 ppm (broad, 2H, —NH—CH—CH$_2$—CH$_2$—CH$_2$—NH—CO—N$\underline{H_2}$), 5.91 ppm (broad, 1H), 7.73 ppm (t, 1H), 8.08 ppm (broad, 1H), 8.23 ppm (t, 1H)

Example 4-3

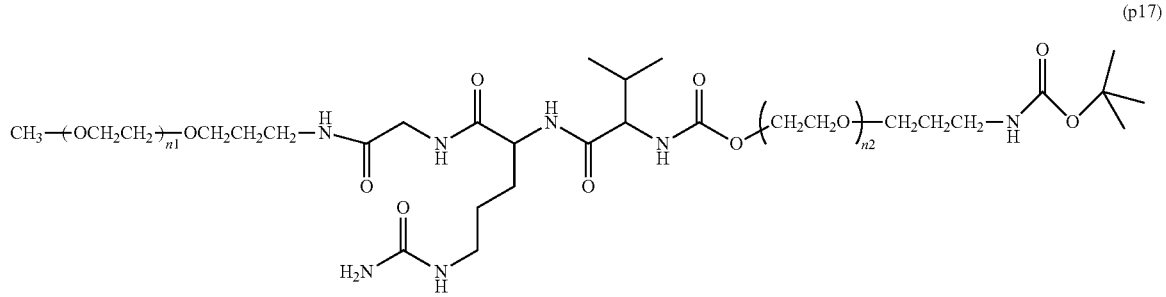

(p17)

n1 = about 480, n2 = about 520

ME-200G(Cit)V-NH$_2$ (1.2 g, 5.7×10$^{-5}$ mol) obtained in Example 4-2 was dissolved in chloroform (7.2 g), triethylamine (9.2 µL, 6.7×10$^{-5}$ mol, manufactured by KANTO CHEMICAL CO., INC.) and heterobifunctional PEG having a propylamino group protected by a tert-butoxycarbonyl group at one terminal and a carbonate succinimidyl group at the other terminal (1.2 g, 5.2×10$^{-5}$ mol, average molecular weight=about 23,000, "SUNBRIGHT BO-200TS" manufactured by NOF CORPORATION) were added, and the mixture was reacted at room temperature under a nitrogen atmosphere for 2 hr. After the reaction, the mixture was concentrated at 40° C., the obtained concentrate was dissolved in ethyl acetate (120 g), hexane (60 g) was added and the mixture was stirred at room temperature for 15 min. The resultant product was precipitated and suction filtered using 5A filter paper. The obtained precipitate was washed with hexane (12 g), suction filtered using 5A filter paper, and dried in vacuo to give the above-mentioned compound (p17) (ME-200G(Cit)V-200Boc). yield 2.1 g.

NMR (CDCl$_3$): 0.96 ppm (d, 3H, —NH—CO—CH—CH(CH$_3$)$_2$), 1.01 ppm (d, 3H, —NH—CO—CH—CH(CH$_3$)$_2$), 1.44 ppm (s, 9H, —CH$_2$—CH$_2$—NH—CO—O—C(CH$_3$)$_3$), 1.59 ppm (m, 2H), 1.76 ppm (m, 3H), 1.82 ppm (q, 2H), 1.92 ppm (m, 1H), 3.09 ppm (m, 1H), 3.23 ppm (m, 2H, —NH—CH—CH$_2$—CH$_2$—CH$_2$—NH—CO—NH$_2$), 3.38 ppm (s, 3H, —NH—CH$_2$—CH$_2$—CH$_2$—O—(CH$_2$—CH$_2$—O)n-CH$_3$), 3.64 ppm (m, about 3,800H, —NH—CH$_2$—CH$_2$—CH$_2$—O—(CH$_2$—CH$_2$—O)n-CH$_3$, —NH—CO—O—CH$_2$—CH$_2$—O—(CH$_2$—CH$_2$—O)n-CH$_2$—CH$_2$—), 4.07 ppm (dd, 1H), 4.15 ppm (m, 2H), 4.31 ppm (m, 1H), 4.38 ppm (m, 1H), 5.02 ppm (broad, 1H), 5.24 ppm (broad, 2H, —NH—CH—CH$_2$—CH$_2$—CH$_2$—NH—CO—NH$_2$), 5.74 ppm (broad, 1H), 5.81 ppm (d, 1H), 7.05 ppm (broad, 1H), 7.46 ppm (broad, 1H), 8.30 ppm (broad, 1H)

Example 4-4

15 min. The resultant product was extracted into the aqueous layer. According to the conditions described in JP-A-2014-208786, the pH of the aqueous layer was adjusted to 2.0 with 1 mol/L hydrochloric acid, the aqueous layer was washed with a mixed solution of toluene and chloroform, whereby polyethylene glycol impurity without an amino group was removed. Successively, the aqueous layer was adjusted to pH 12 by adding an appropriate amount of 1 mol/L aqueous sodium hydroxide solution, sodium chloride (5.0 g) was dissolved. Chloroform (10 g) was added, and the mixture was stirred at room temperature for 15 min. The resultant product was extracted into the organic layer. The aqueous layer and the organic layer were separated, chloroform (10 g) was again added to the aqueous layer, and the mixture was stirred at room temperature for 15 min. The resultant product was extracted into the organic layer. The organic layer obtained by the first and the second extraction was concentrated at 40° C., and ethyl acetate (100 g) was added to the obtained concentrate. Sodium sulfate (2.0 g) was added to the obtained ethyl acetate solution, and the mixture was stirred at 30° C. for 15 min, and suction filtration was performed using a Kiriyama funnel lined with Oplite on 5A filter paper. Hexane (50 g) was added to the obtained filtrate, and the mixture was stirred at room temperature for 15 min. The resultant product was precipitated and suction filtered using 5A filter paper. The precipitate was washed with hexane (20 g), suction filtered using 5A filter paper, and dried in vacuo to give the above-mentioned compound (p14) (ME-200G(Cit)V-200PA). yield 1.7 g. The molecular weight is shown in Table 1. HPLC: amine purity 92%.

NMR (CDCl$_3$): 0.96 ppm (d, 3H, —NH—CO—CH—CH(CH$_3$)$_2$), 1.01 ppm (d, 3H, —NH—CO—CH—CH(CH$_3$)$_2$), 1.60 ppm (m, 2H), 1.75 ppm (m, 3H), 1.82 ppm (m, 2H), 1.93 ppm (m, 1H), 2.23 ppm (m, 1H), 2.82 ppm (t, 2H, —CH$_2$—CH$_2$—CH$_2$—NH$_2$), 3.10 ppm (m, 1H), 3.30 ppm (m, 2H), 3.38 ppm (m, 4H), 3.64 ppm (m, about 3,800H,

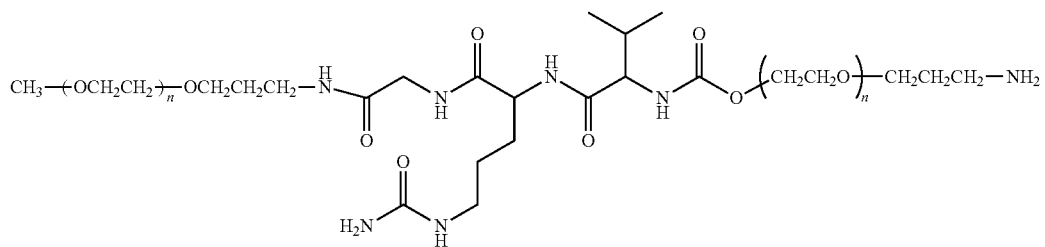

(p14)

n1 = about 480, n2 = about 520

ME-200G(Cit)V-200Boc (2.0 g, 4.5×10$^{-5}$ mol) obtained in Example 4-3 was dissolved in dichloromethane (10 g), methanesulfonic acid (291 µL, 4.5×10$^{-3}$ mol, manufactured by KANTO CHEMICAL CO., INC.) was added, and the mixture was reacted at room temperature under a nitrogen atmosphere for 2 hr. Thereafter, the reaction mixture was diluted with toluene (20 g), ion exchange water (20 g) was added, and the mixture was stirred at room temperature for —NH—CH$_2$—CH$_2$—CH$_2$—O—(CH$_2$—CH$_2$—O)n-CH$_3$, —NH—CO—O—CH$_2$—CH$_2$—O—(CH$_2$—CH$_2$—O)n-CH$_2$—CH$_2$—), 3.95 ppm (m, 1H), 4.07 ppm (dd, 1H), 4.15 ppm (m, 1H), 4.31 ppm (m, 1H), 4.38 ppm (m, 1H), 5.24 ppm (broad, 2H, —NH—CH—CH$_2$—CH$_2$—CH$_2$—NH—CO—NH$_2$), 5.79 ppm (broad, 1H), 5.82 ppm (broad, 1H), 7.06 ppm (broad, 1H), 7.48 ppm (broad, 1H), 8.31 ppm (broad, 1H)

Example 5

Synthesis of Compound (p18)
(ME-200G(Cit)V-200 MA)

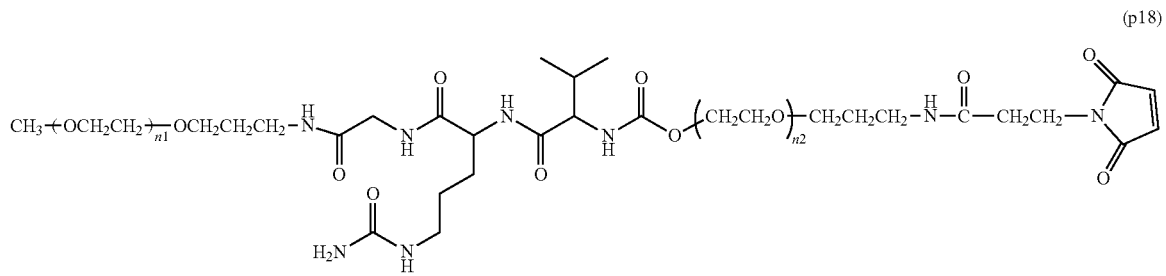

(p18)

n1 = about 480, n2 = about 520

To ME-200G(Cit)V-200PA (0.2 g, 4.5×10⁻⁶ mol) obtained in Example 4-4 were added toluene (1.1 g) and acetonitrile (0.16 g) and the mixture was dissolved by heating at 40° C. To the obtained solution were added N-methylmorpholine (2.5 µL, 2.2×10⁻⁵ mol, manufactured by KANTO CHEMICAL CO., INC.) and N-succinimidyl-3-maleimidopropionate (1.8 mg, 6.8×10⁻⁶ mol, manufactured by Osaka Synthetic Chemical Laboratories, Inc.), and the mixture was reacted at 40° C. under a nitrogen atmosphere for 1 hr. Ethyl acetate (6.0 g) was added to the reaction solution, and the mixture was stirred to uniformity, hexane (8.0 g) was added at 17° C., the mixture was stirred at 17° C. for 15 min, and the resultant product was precipitated. After suction filtration using 5A filter paper, the precipitate was washed with hexane (8.0 g), suction filtered using 5A filter paper, and dried in vacuo to give the above-mentioned compound (p18) (ME-200G(Cit)V-200 MA). yield 0.12 g. The molecular weight is shown in Table 1. The maleimide purity was 88% ($^1$H-NMR).

NMR (CDCl$_3$): 0.96 ppm (d, 3H, —NH—CO—CH—CH(CH$_3$)$_2$), 1.01 ppm (d, 3H, —NH—CO—CH—CH(CH$_3$)$_2$), 1.59 ppm (broad, 2H), 1.76 ppm (m, 5H), 2.46 ppm (t, 2H, —CH$_2$—CH$_2$—CH$_2$—C$_4$NO$_2$H$_2$), 3.12 ppm (m, 1H), 3.34 ppm (m, 5H), 3.64 ppm (m, about 3,800H, —NH—CH$_2$—CH$_2$—CH$_2$—O—(CH$_2$—CH$_2$—O)n-CH$_3$, —NH—CO—O—CH$_2$—CH$_2$—O—(CH$_2$—CH$_2$—O)n-CH$_2$—CH$_2$—), 4.02 ppm (m, 1H), 4.13 ppm (m, 1H), 4.28 ppm (m, 1H), 4.37 ppm (m, 1H), 5.86 ppm (broad, 1H), 6.42 ppm (broad, 1H), 6.68 ppm (s, 2H, —CH$_2$—CH$_2$—CH$_2$—NH—CO—CH$_2$—CH$_2$—C$_4$NO$_2$H$_2$), 7.04 ppm (broad, 1H), 7.46 ppm (broad, 1H), 8.20 ppm (broad, 1H)

Example 6

Synthesis of Compound (p19)
(ME-200GGG-200PA)

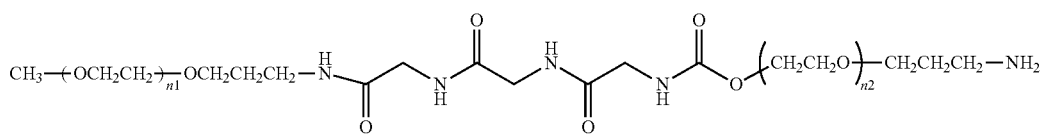

(p19)

n1 = about 480, n2 = about 520

Example 6-1

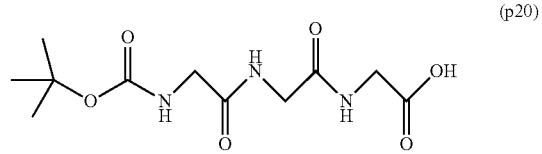 [SMILES: CC(C)(C)OC(=O)NCC(=O)NCC(=O)NCC(=O)O]

(p20)

To Glycyl-glycyl-glycine (2.0 g, 1.1×10⁻² mol, manufactured by KANTO CHEMICAL CO., INC.) were added ion exchange water (60 g) and sodium hydrogen carbonate (4.5 g), and the mixture was dissolved. Tetrahydro furan (60 g) and di-tert-butyl dicarbonate (Boc$_2$O) (4.6 g, 2.1×10⁻² mol, manufactured by Tokyo Chemical Industry Co., Ltd.) were added, and the mixture was reacted at 40° C. for 23 hr. Water (120 g) was added to the reaction solution, and the mixture was cooled to 5° C. An appropriate amount of phosphoric acid was added to adjust the pH to 7, hexane (120 g) was added and the mixture was stirred at room temperature for 15 min. The organic layer and the aqueous layer were separated, hexane (120 g) was added again to the aqueous layer, and the mixture was stirred at room temperature for 15 min. The aqueous layer was recovered, ethanol (100 g) was added and the mixture was concentrated at 50° C., ethanol (100 g) was added again and the mixture was concentrated at 50° C. Ethanol (100 g) was added to the obtained concentrate, and the mixture was dissolved by heating at 50° C., and suction filtration was performed using a Kiriyama funnel lined with Oplite on 5A filter paper. The obtained filtrate was concentrated at 50° C. and dried in vacuo to give Boc-glycyl-glycyl-glycine. yield 1.5 g.

NMR (D$_2$O): 1.45 ppm (s, 9H, —NH—CO—O—C(CH$_3$)$_3$), 3.78 ppm (s, 2H, —CH$_2$—NH—CO—O—C(CH$_3$)$_3$), 3.84 ppm (s, 2H, —CO—NH—CH$_2$—COOH), 4.00 ppm (s, 2H, —CO—NH—CH$_2$—CO—NH—)

Example 6-2

To Boc-glycyl-glycyl-glycine (0.174 g, 6.0×10$^{-4}$ mol) and methoxy PEG having a propylamino group at the terminal (3.0 g, 1.4×10$^{-4}$ mol, average molecular weight=about 21,000, "SUNBRIGHT MEPA-20T" manufactured by NOF CORPORATION) was added dehydrated N,N'-dimethylformamide (27 g), and the mixture was dissolved by heating at 30° C. Thereafter, diisopropylethylamine (191 μL, 1.1×10$^{-3}$ mol, manufactured by KANTO CHEMICAL CO., INC.) and (1-cyano-2-ethoxy-2-oxoethylideneaminooxy)dimethylamino-morpholino-carbenium hexafluorophosphate (COMU) (0.321 g, 7.5×10$^{-4}$ mol, manufactured by Sigma Ltd. Aldrich) were added, and the mixture was reacted at room temperature under a nitrogen atmosphere for 1 hr. After completion of the reaction, the mixture was diluted with chloroform (300 g), saturated aqueous sodium hydrogen carbonate solution (120 g) was added, and the mixture was stirred at room temperature for 15 min for washing. The aqueous layer and the organic layer were separated, saturated aqueous sodium hydrogen carbonate solution (120 g) was added again to the organic layer, the mixture was stirred at room temperature for 15 min for washing, and the organic layer was recovered. Magnesium sulfate (3.0 g) was added to the obtained chloroform solution. The mixture was stirred for 30 min for dehydration, and suction filtration was performed using a Kiriyama funnel lined with Oplite on 5A filter paper. The obtained filtrate was concentrated at 40° C., ethyl acetate (120 g) was added to the concentrate and the mixture was stirred to uniformity. Hexane (60 g) was added, and the mixture was stirred at room temperature for 15 min. The resultant product was precipitated and suction filtered using 5A filter paper. The precipitate was recovered, dissolved again in ethyl acetate (120 g), hexane (60 g) was added, and the mixture was stirred at room temperature for 15 min. The resultant product was precipitated and suction filtered using 5A filter paper. The precipitate was recovered, washed with hexane (60 g), suction filtered using 5A filter paper, and dried in vacuo to give the above-mentioned compound (p21) (ME-200GGG-Boc). yield 2.6 g.

NMR (CDCl$_3$): 1.45 ppm (s, 9H, —NH—CO—O—C(CH$_3$)$_3$), 1.80 ppm (m, 2H, —CO—NH—CH$_2$—CH$_2$—CH$_2$—O—(CH$_2$—CH$_2$—O)n-CH$_3$), 3.38 ppm (m, 5H), 3.64 ppm (m, about 1,900H, —CO—NH—CH$_2$—CH$_2$—CH$_2$—O—(CH$_2$—CH$_2$—O)n-CH$_3$), 3.86 ppm (d, 2H, —CH$_2$—NH—CO—O—C(CH$_3$)$_3$), 3.91 ppm (d, 2H), 3.99 ppm (d, 2H), 5.69 ppm (broad, 1H), 7.10 ppm (broad, 1H), 7.44 ppm (broad, 2H)

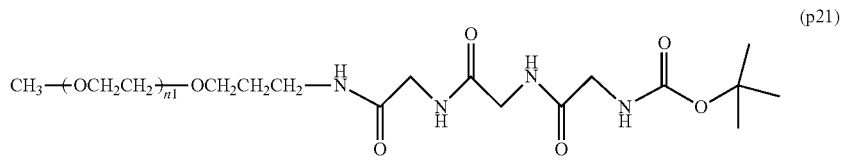

(p21)

n1 = about 480

Example 6-3

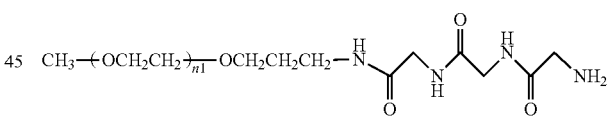

(p22)

n1 = about 480

ME-200GGG-Boc (2.4 g, 1.1×10$^{-4}$ mol) obtained in Example 6-2 was dissolved in dichloromethane (12 g), methanesulfonic acid (723 μL, 1.1×10$^{-2}$ mol, manufactured by KANTO CHEMICAL CO., INC.) was added, and the mixture was reacted at room temperature under a nitrogen atmosphere for 2 hr. Thereafter, the reaction mixture was diluted with toluene (24 g), ion exchange water (24 g) was added, and the mixture was stirred at room temperature for 15 min. The resultant product was extracted into the aqueous layer. To the obtained aqueous layer was added an appropriate amount of 1 mol/L aqueous sodium hydroxide solution to adjust the pH to 12, and sodium chloride (6.0 g) was dissolved. Chloroform (12 g) was added thereto, and the mixture was stirred at room temperature for 15 min. The resultant product was extracted into the organic layer. The aqueous layer and the organic layer were separated, chloroform (12 g) was added again to the aqueous layer, and the mixture was stirred at room temperature for 15 min. The resultant product was extracted into the organic layer. The organic layer obtained by the first and the second extraction was concentrated at 40° C., and ethyl acetate (120 g) was added to the obtained concentrate. Sodium sulfate (2.4 g) was added to the obtained ethyl acetate solution, and the mixture was stirred at 30° C. for 15 min, and suction filtration was performed using a Kiriyama funnel lined with Oplite on 5A filter paper. Hexane (60 g) was added to the obtained filtrate, and the mixture was stirred at room temperature for 15 min. The resultant product was precipitated and suction filtered using 5A filter paper. The precipitate was washed with hexane (24 g), suction filtered using 5A filter paper, and dried in vacuo to give the above-mentioned compound (p22) (ME-200GGG-NH$_2$). yield 2.2 g.

NMR (CDCl$_3$): 1.53 ppm (broad, 1H), 1.79 ppm (m, 2H, —CO—NH—CH$_2$—CH$_2$—CH$_2$—O—(CH$_2$—CH$_2$—O)n-CH$_3$), 3.38 ppm (m, 5H), 3.64 ppm (m, about 1,900H, —CO—NH—CH$_2$—CH$_2$—CH$_2$—O—(CH$_2$—CH$_2$—O)n-CH$_3$), 3.92 ppm (d, 2H), 4.01 ppm (broad, 1H), 7.06 ppm (broad, 1H), 7.24 ppm (broad, 1H), 7.86 ppm (broad, 1H)

Example 6-4

(p23)

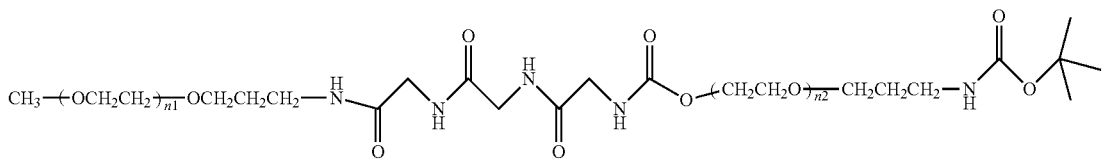

n1 = about 480, n2 = about 520

ME-200GGG-NH$_2$ (1.5 g, 7.1×10$^{-5}$ mol) obtained in Example 6-3 was dissolved in chloroform (7.5 g), triethylamine (11.6 L, 8.4×10$^{-5}$ mol, manufactured by KANTO CHEMICAL CO., INC.) and heterobifunctional PEG having a propylamino group protected by a tert-butoxycarbonyl group at one terminal and a carbonate succinimidyl group at the other terminal (1.8 g, 7.8×10$^{-5}$ mol, average molecular weight=about 23,000, "SUNBRIGHT BO-200TS" manufactured by NOF CORPORATION) were added, and the mixture was reacted at room temperature under a nitrogen atmosphere for 2 hr. After the reaction, the mixture was concentrated at 40° C., the obtained concentrate was dissolved in ethyl acetate (150 g), hexane (75 g) was added and the mixture was stirred at room temperature for 15 min. The resultant product was precipitated and suction filtered using 5A filter paper. The obtained precipitate was washed with hexane (75 g), suction filtered using 5A filter paper, and dried in vacuo to give the above-mentioned compound (p23) (ME-200GGG-200Boc). yield 3.0 g.

NMR (CDCl$_3$): 1.44 ppm (s, 9H, —CH$_2$—CH$_2$—CH$_2$—NH—CO—O—C(CH$_3$)$_3$), 1.78 ppm (m, 4H, —CO—NH—CH$_2$—CH$_2$—CH$_2$—O—(CH$_2$—CH$_2$—O)n-CH$_3$, —CH$_2$—CH$_2$—CH$_2$—NH—CO—O—C(CH$_3$)$_3$), 3.23 ppm (m, 2H, —CH$_2$—CH$_2$—CH$_2$—NH—CO—O—C(CH$_3$)$_3$), 3.35 ppm (m, 2H), 3.38 ppm (s, 3H, —CO—NH—CH$_2$—CH$_2$—CH$_2$—O—(CH$_2$—CH$_2$—O)n-CH$_3$), 3.65 ppm (m, about 3,800H, —NH—CH$_2$—CH$_2$—CH$_2$—O—(CH$_2$—CH$_2$—O)n-CH$_3$, —NH—CO—O—CH$_2$—CH$_2$—O—(CH$_2$—CH$_2$—O)n-CH$_2$—CH$_2$—), 3.97 ppm (d, 2H), 4.23 ppm (broad, 2H, —NH—CO—O—CH$_2$—CH$_2$—O—(CH$_2$—CH$_2$—O)n-CH$_2$—CH$_2$—), 5.01 ppm (broad, 1H), 6.21 ppm (broad, 1H), 7.00 ppm (broad, 1H), 7.47 ppm (broad, 1H), 7.61 ppm (broad, 1H)

Example 6-5

(p19)

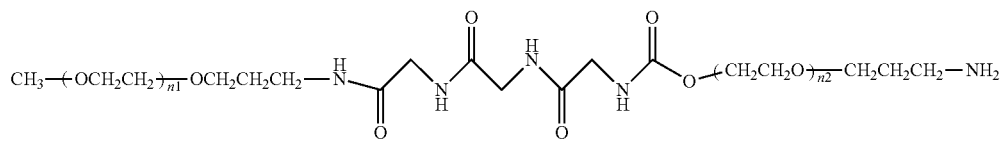

n1 = about 480, n2 = about 520

ME-200GGG-200Boc (2.5 g, 5.8×10⁻⁵ mol) obtained in Example 6-4 was dissolved in dichloromethane (12.5 g), methanesulfonic acid (365 μL, 5.6×10⁻³ mol, manufactured by KANTO CHEMICAL CO., INC.) was added, and the mixture was reacted at room temperature under a nitrogen atmosphere for 2 hr. Thereafter, the reaction mixture was diluted with toluene (25 g), ion exchange water (25 g) was added, and the mixture was stirred at room temperature for 15 min. The resultant product was extracted into the aqueous layer. According to the conditions described in JP-A-2014-208786, the pH of the aqueous layer was adjusted to 2.0 with 1 mol/L hydrochloric acid, and the aqueous layer was washed with a mixed solution of toluene and chloroform, whereby polyethylene glycol impurity without an amino group was removed. Successively, the aqueous layer was adjusted to pH 12 by adding an appropriate amount of 1 mol/L aqueous sodium hydroxide solution, and sodium chloride (6.3 g) was dissolved. Chloroform (12.5 g) was added thereto, and the mixture was stirred at room temperature for 15 min. The resultant product was extracted into the organic layer. The aqueous layer and the organic layer were separated, chloroform (12.5 g) was added again to the aqueous layer, and the mixture was stirred at room temperature for 15 min. The resultant product was extracted into the organic layer. The organic layer obtained by the first and the second extraction was concentrated at 40° C., and ethyl acetate (125 g) was added to the obtained concentrate. Sodium sulfate (2.5 g) was added to the obtained ethyl acetate solution, and the mixture was stirred at 30° C. for 15 min, and suction filtration was performed using a Kiriyama funnel lined with Oplite on 5A filter paper. Hexane (62.5 g) was added to the obtained filtrate, and the mixture was stirred at room temperature for 15 min. The resultant product was precipitated and suction filtered using 5A filter paper. The precipitate was washed with hexane (25 g), suction filtered using 5A filter paper, and dried in vacuo to give the above-mentioned compound (p19) (ME-200GGG-200PA). yield 2.4 g. The molecular weight is shown in Table 1. HPLC: amine purity 91%.

NMR (CDCl₃): 1.79 ppm (m, 4H, —CO—NH—CH₂—CH₂—CH₂—O—(CH₂—CH₂—O)n-CH₃, —CH₂—CH₂—CH₂—NH₂), 2.91 ppm (broad, 2H), 3.37 ppm (m, 5H), 3.65 ppm (m, about 3,800H, —NH—CH₂—CH₂—CH₂—O—(CH₂—CH₂—O)n-CH₃, —NH—CO—O—CH₂—CH₂—O—(CH₂—CH₂—O)n-CH₂—CH₂—), 3.90 ppm (t, 3H), 3.97 ppm (d, 2H), 4.23 ppm (broad, 2H, —NH—CO—O—CH₂—CH₂—O—(CH₂—CH₂—O)n-CH₂—CH₂—), 6.19 ppm (broad, 1H), 7.00 ppm (broad, 1H), 7.45 ppm (broad, 1H), 7.61 ppm (broad, 1H)

Example 7

Synthesis of Compound (p24) (ME-200GF-200PA)

(p24)

CH₃—(OCH₂CH₂)$_{n1}$—OCH₂CH₂CH₂—NH—... —O—(CH₂CH₂O)$_{n2}$—CH₂CH₂CH₂—NH₂ n1 = about 480, n2 = about 520

Example 7-1

(p25)

CH₃—(OCH₂CH₂)$_{n1}$—OCH₂CH₂CH₂—NH—...

n1 = about 480

To L-phenylalanyl-glycine with the N terminal protected by a 9-fluorenylmethyloxycarbonyl group (Fmoc group) (Fmoc-Phe-Gly) (0.533 g, $1.2\times10^{-3}$ mol, manufactured by WATANABE CHEMICAL INDUSTRIES, LTD.) and methoxy PEG having a propylamino group at the terminal (6.0 g, $2.9\times10^{-4}$ mol, average molecular weight=about 21,000, "SUNBRIGHT MEPA-20T" manufactured by NOF CORPORATION) was added dehydrated N,N'-dimethylformamide (60 g), and the mixture was dissolved by heating at 30° C. Thereafter, diisopropylethylamine (383 μL, $2.3\times10^{-3}$ mol, manufactured by KANTO CHEMICAL CO., INC.) and (1-cyano-2-ethoxy-2-oxoethylideneaminooxy)dimethylamino-morpholino-carbenium hexafluorophosphate (COMU) (0.642 g, $1.5\times10^{-3}$ mol, manufactured by Sigma Ltd. Aldrich) were added, and the mixture was reacted at room temperature under a nitrogen atmosphere for 1 hr. After completion of the reaction, the mixture was diluted with chloroform (600 g), saturated aqueous sodium hydrogen carbonate solution (240 g) was added, and the mixture was stirred at room temperature for 15 min for washing. The aqueous layer and the organic layer were separated, saturated aqueous sodium hydrogen carbonate solution (240 g) was added again to the organic layer, the mixture was stirred at room temperature for 15 min for washing, and the organic layer was recovered. To the obtained chloroform solution was added magnesium sulfate (2.4 g), and the mixture was stirred for 30 min for dehydration, and suction filtration was performed using a Kiriyama funnel lined with Oplite on 5A filter paper. The obtained filtrate was concentrated at 40° C., ethyl acetate (240 g) was added to the concentrate, and the mixture was stirred to uniformity. Hexane (120 g) was added, and the mixture was stirred at room temperature for 15 min. The resultant product was precipitated and suction filtered using 5A filter paper. The precipitate was recovered, dissolved again in ethyl acetate (240 g), hexane (120 g) was added, and the mixture was stirred at room temperature for 15 min. The resultant product was precipitated and suction filtered using 5A filter paper. The precipitate was recovered, washed with hexane (120 g), suction filtered using 5A filter paper, and dried in vacuo to give the above-mentioned compound (p25) (ME-200GF-Fmoc). yield 5.1 g.

NMR ($d_6$-DMSO): 1.62 ppm (m, 2H, —CO—NH—$CH_2$—$\underline{CH_2}$—$CH_2$—O—($CH_2$—$CH_2$—O)n-$CH_3$), 2.80 ppm (m, 1H, —NH—CO—CH—$\underline{CH_2}$—$C_6H_5$), 3.04 ppm (m, 1H, —NH—CO—CH—$\underline{CH_2}$—$C_6H_5$), 3.10 ppm (m, 2H, —CO—NH—$\underline{CH_2}$—$CH_2$—$CH_2$—O—($CH_2$—$CH_2$—O)n-$CH_3$), 3.24 ppm (s, 3H, —CO—NH—$CH_2$—$CH_2$—$CH_2$—O—($CH_2$—$CH_2$—O)n-$\underline{CH_3}$), 3.48 ppm (m, about 1,900H, —CO—NH—$CH_2$—$CH_2$—$CH_2$—O—($\underline{CH_2}$—$\underline{CH_2}$—O)n-$CH_3$), 4.20 ppm (m, 4H), 7.33 ppm (m, 9H), 7.66 ppm (m, 4H, Ar), 7.88 ppm (d, 2H, Ar), 8.27 ppm (t, 1H)

Example 7-2

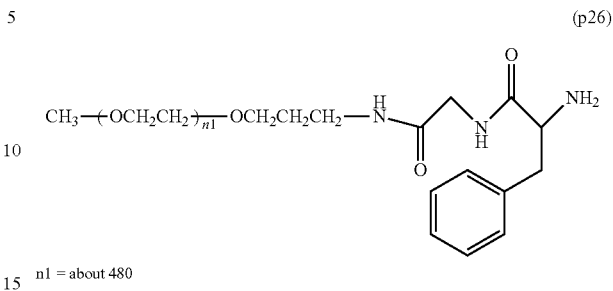

n1 = about 480

To ME-200GF-Fmoc (4.9 g, $2.3\times10^{-4}$ mol) obtained in Example 7-1 was added N,N'-dimethylformamide (29.4 g), and the mixture was dissolved by heating at 30° C. Piperidine (1.55 g, $1.8\times10^{-2}$ mol, manufactured by Wako Pure Chemical Industries, Ltd.) was added, and the mixture was reacted at room temperature under a nitrogen atmosphere for 2 hr. After completion of the reaction, ethyl acetate (300 g) was added and the mixture was stirred to uniformity. Hexane (150 g) was added, and the mixture was stirred at room temperature for 15 min. The resultant product was precipitated and suction filtered using 5A filter paper. The precipitate was recovered, dissolved again in ethyl acetate (300 g), hexane (150 g) was added, and the mixture was stirred at room temperature for 15 min. The resultant product was precipitated and suction filtered using 5A filter paper. The precipitate was recovered, washed with hexane (150 g), suction filtered using 5A filter paper, and dried in vacuo to give the above-mentioned compound (p26) (ME-200GF-$\underline{NH_2}$). yield 3.9 g.

NMR ($d_6$-DMSO): 1.62 ppm (m, 2H, —CO—NH—$CH_2$—$\underline{CH_2}$—$CH_2$—O—($CH_2$—$CH_2$—O)n-$CH_3$), 1.64 ppm (broad, 1H), 2.59 ppm (dd, 1H, —NH—CO—CH—$\underline{CH_2}$—$C_6H_5$), 2.98 ppm (dd, 1H, —NH—CO—CH—$\underline{CH_2}$—$C_6H_5$), 3.10 ppm (q, 2H, —CO—NH-$\underline{CH_2}$—$CH_2$—$CH_2$—O—($CH_2$—$CH_2$—O)n-$CH_3$), 3.24 ppm (s, 3H, —CO—NH—$CH_2$—$CH_2$—$CH_2$—O—($CH_2$—$CH_2$—O)n-$\underline{CH_3}$), 3.48 ppm (m, about 1,900H, —CO—NH—$CH_2$—$CH_2$—$CH_2$—O—($\underline{CH_2}$—$\underline{CH_2}$—O)n-$CH_3$), 7.24 ppm (m, 6H, —NH—CO—CH—$CH_2$—$C_6H_5$, —NH—), 7.73 ppm (t, 1H), 8.12 ppm (broad, 1H)

Example 7-3

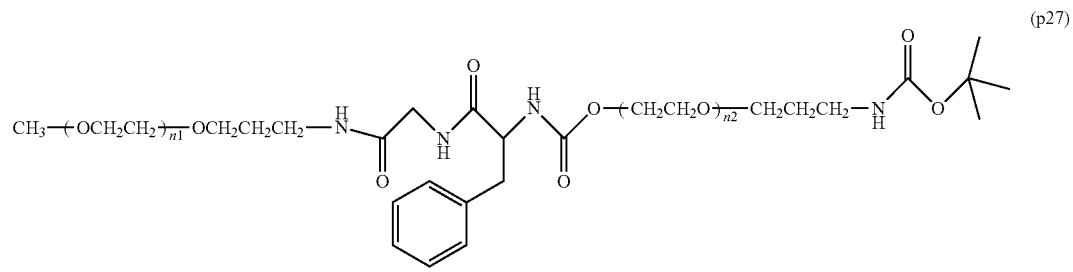

n1 = about 480, n2 = about 520

ME-200GF-NH$_2$ (0.98 g, 4.7×10$^{-5}$ mol) obtained in Example 7-2 was dissolved in chloroform (4.9 g), triethylamine (7.5 L, 5.4×10$^{-5}$ mol, manufactured by KANTO CHEMICAL CO., INC.) and heterobifunctional PEG having a propylamino group protected by a tert-butoxycarbonyl group at one terminal and a carbonate succinimidyl group at the other terminal (1.3 g, 6.2×10$^{-5}$ mol, average molecular weight=about 23,000, "SUNBRIGHT BO-200TS" manufactured by NOF CORPORATION) were added, and the mixture was reacted at room temperature under a nitrogen atmosphere for 2 hr. After the reaction, the mixture was concentrated at 40° C., the obtained concentrate was dissolved in ethyl acetate (98 g), hexane (49 g) was added and the mixture was stirred at room temperature for 15 min. The resultant product was precipitated and suction filtered using 5A filter paper. The obtained precipitate was washed with hexane (49 g), suction filtered using 5A filter paper, and dried in vacuo to give the above-mentioned compound (p27) (ME-200GF-200Boc). yield 2.0 g.

NMR (CDCl$_3$): 1.44 ppm (s, 9H, —CH$_2$—CH$_2$—CH$_2$—NH—CO—O—C(CH$_3$)$_3$), 1.77 ppm (m, 4H, —CO—NH—CH$_2$—CH$_2$—CH$_2$—O—(CH$_2$—CH$_2$—O)n-CH$_3$, —CH$_2$—CH$_2$—CH$_2$—NH—CO—O—C(CH$_3$)$_3$), 3.02 ppm (m, 1H), 3.21 ppm (m, 3H), 3.36 ppm (m, 4H), 3.65 ppm (m, about 3,800H, —NH—CH$_2$—CH$_2$—CH$_2$—O—(CH$_2$—CH$_2$—O)n-CH$_3$, —NH—CO—O—CH$_2$—CH$_2$—O—(CH$_2$—CH$_2$—O)n-CH$_2$—CH$_2$—), 4.18 ppm (m, 2H, —NH—CO—O—CH$_2$—CH$_2$—O—(CH$_2$—CH$_2$—O)n-CH$_2$—CH$_2$—), 4.39 ppm (q, 1H, —NH—CO—CH—CH$_2$—C$_6$H$_5$), 5.03 ppm (broad, 1H), 5.55 ppm (d, 1H), 6.86 ppm (broad, 1H), 7.02 ppm (broad, 1H), 7.25 ppm (m, 5H, —NH—CO—CH—CH$_2$—C$_6$H$_5$)

Example 7-4 layer. According to the conditions described in JP-A-2014-208786, the pH of the aqueous layer was adjusted to 2.0 with 1 mol/L hydrochloric acid, the aqueous layer was washed with a mixed solution of toluene and chloroform, whereby polyethylene glycol impurity without an amino group was removed. Successively, the aqueous layer was adjusted to pH 12 by adding an appropriate amount of 1 mol/L aqueous sodium hydroxide solution, and sodium chloride (4.5 g) was dissolved. Chloroform (18 g) was added thereto, and the mixture was stirred at room temperature for 15 min. The resultant product was extracted into the organic layer. The aqueous layer and the organic layer were separated, chloroform (18 g) was added again to the aqueous layer, and the mixture was stirred at room temperature for 15 min. The resultant product was extracted into the organic layer. The organic layer obtained by the first and the second extraction was concentrated at 40° C., and ethyl acetate (90 g) was added to the obtained concentrate. Sodium sulfate (1.8 g) was added to the obtained ethyl acetate solution, and the mixture was stirred at 30° C. for 15 min, and suction filtration was performed using a Kiriyama funnel lined with Oplite on 5A filter paper. Hexane (45 g) was added to the obtained filtrate, and the mixture was stirred at room temperature for 15 min. The resultant product was precipitated and suction filtered using 5A filter paper. The precipitate was washed with hexane (18 g), suction filtered using 5A filter paper, and dried in vacuo to give the above-mentioned compound (p24) (ME-200GF-200PA). yield 1.7 g. The molecular weight is shown in Table 1. HPLC: amine purity 87%.

NMR (CDCl$_3$): 1.77 ppm (m, 4H, —CO—NH—CH$_2$—CH$_2$—CH$_2$—O—(CH$_2$—CH$_2$—O)n-CH$_3$, —CH$_2$—CH$_2$—CH$_2$—NH$_2$), 2.87 ppm (m, 2H), 3.07 ppm (m, 1H), 3.30 ppm (m, 3H), 3.38 ppm (s, 3H, —NH—CH$_2$—CH$_2$—

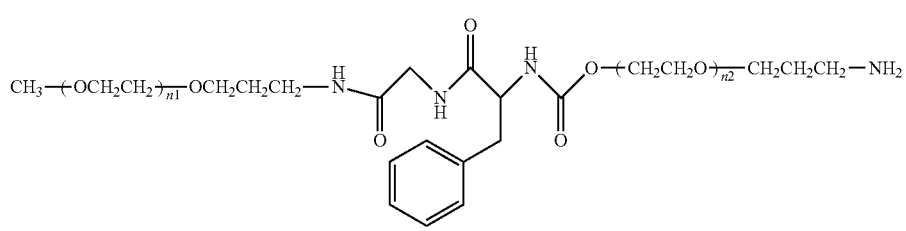

(p24)

n1 = about 480, n2 = about 520

ME-200GF-200Boc (1.8 g, 4.1×10$^{-5}$ mol) obtained in Example 7-3 was dissolved in dichloromethane (9.0 g), methanesulfonic acid (262 μL, 4.3×10$^{-3}$ mol, manufactured by KANTO CHEMICAL CO., INC.) was added, and the mixture was reacted at room temperature under a nitrogen atmosphere for 2 hr. Thereafter, the reaction mixture was diluted with toluene (18 g), ion exchange water (18 g) was added, and the mixture was stirred at room temperature for 15 min. The resultant product was extracted into the aqueous CH$_2$—O—(CH$_2$—CH$_2$—O)n-CH$_3$), 3.64 ppm (m, about 3,800H, —NH—CH$_2$—CH$_2$—CH$_2$—O—(CH$_2$—CH$_2$—O)n-CH$_3$, —NH—CO—O—CH$_2$—CH$_2$—O—(CH$_2$—CH$_2$—O)n-CH$_2$—CH$_2$—), 4.18 ppm (m, 2H, —NH—CO—O—CH$_2$—CH$_2$—O—(CH$_2$—CH$_2$—O)n-CH$_2$—CH$_2$—), 4.32 ppm (q, 1H, —NH—CO—CH—CH$_2$—C$_6$H$_5$), 5.56 ppm (broad, 1H), 6.83 ppm (broad, 1H), 6.96 ppm (broad, 1H), 7.25 ppm (m, 5H, —NH—CO—CH—CH$_2$—C$_6$H$_5$)

Example 8

Synthesis of Compound (p28) (ME-200GAV-200PA)

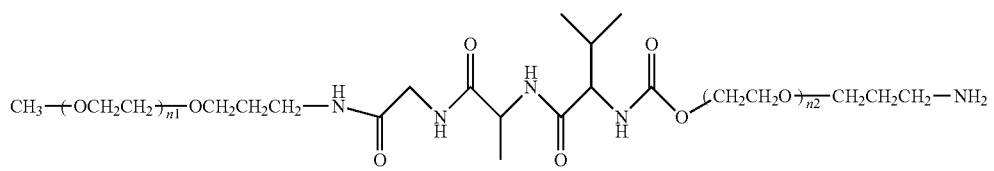

n1 = about 480, n2 = about 450

By the same production method as in Example 4 and using L-valine-L-alanine-glycine with the N terminal protected by a 9-fluorenylmethyloxycarbonyl group (Fmoc group) (Fmoc-Val-Ala-Gly) as the starting material, the above-mentioned compound (p28) (ME-200GAV-200PA) was obtained. yield 1.0 g. The molecular weight is shown in Table 1. HPLC: amine purity 90%.

NMR ($d_6$-DMSO): 0.82 ppm (dd, 6H, —NH—CO—CH—CH$_2$—CH(CH$_3$)$_2$), 1.21 ppm (d, 3H, —NH—CO—CH(CH$_3$)—), 1.62 ppm (m, 4H, —CO—NH—CH$_2$—CH$_2$—CH$_2$—O—(CH$_2$—CH$_2$—O)n-CH$_3$, —CH$_2$—CH$_2$—CH$_2$—NH$_2$), 1.95 ppm (m, 1H), 3.10 ppm (m, 2H), 3.23 ppm (s, 3H, —O—(CH$_2$—CH$_2$—O)n-CH$_3$), 3.60 ppm (m, about 3,800H, —NH—CH$_2$—CH$_2$—CH$_2$—O—(CH$_2$—CH$_2$—O)n-CH$_3$, —NH—CO—O—CH$_2$—CH$_2$—O—(CH$_2$—CH$_2$—O)n-CH$_2$—CH$_2$—), 4.05 ppm (m, 2H), 4.22 ppm (m, 1H), 7.24 ppm (broad, 1H), 7.69 ppm (broad, 1H), 8.10 ppm (broad, 2H)

Example 9

Synthesis of Compound (p29) (ME-200GFGG (SEQ ID NO: 5)-200PA)

By the same production method as in Example 4 and using glycine-glycine-L-phenylalanine-glycine (SEQ ID NO: 5) with the N terminal protected by a 9-fluorenylmethyloxycarbonyl group (Fmoc group) (Fmoc-Gly-Gly-Phe-Gly (SEQ ID NO: 5)) as the starting material, the above-mentioned compound (p29) (ME-200GFGG (SEQ ID NO: 5)-200PA) was obtained. yield 1.2 g. The molecular weight is shown in Table 1. HPLC: amine purity 91%.

NMR ($d_6$-DMSO): 1.62 ppm (m, 4H, —CO—NH—CH$_2$—CH$_2$—CH$_2$—O—(CH$_2$—CH$_2$—O)n-CH$_3$, —CH$_2$—CH$_2$—CH$_2$—NH$_2$), 2.80 ppm (m, 1H), 3.10 ppm (m, 2H), 3.23 ppm (s, 3H, —O—(CH$_2$—CH$_2$—O)n-CH$_3$), 3.60 ppm (m, about 3,800H, —NH—CH$_2$—CH$_2$—CH$_2$—O—(CH$_2$—CH$_2$—O)n-CH$_3$, —NH—CO—O—CH$_2$—CH$_2$—O—(CH$_2$—CH$_2$—O)n-CH$_2$—CH$_2$—), 4.05 ppm (m, 2H), 4.47 ppm (m, 1H), 7.20 ppm (m, 5H, —NH—CO—CH—CH$_2$—C$_6$H$_5$), 7.43 ppm (broad, 1H), 7.62 ppm (broad, 1H), 8.00 ppm (broad, 1H), 8.12 ppm (broad, 1H), 8.24 ppm (broad, 1H)

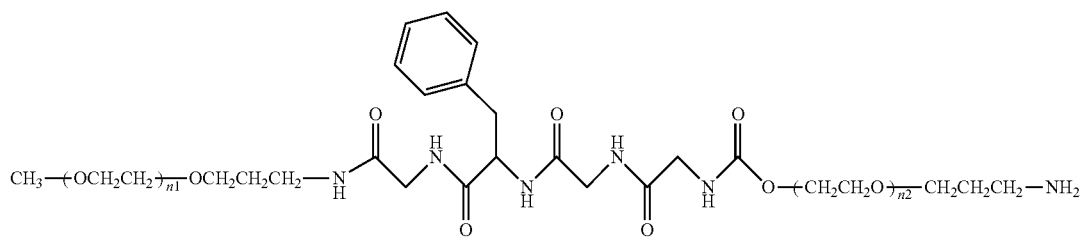

n1 = about 480, n2 = about 450

Example 10

Synthesis of Compound (p30)
(ME-200GFG-200PA)

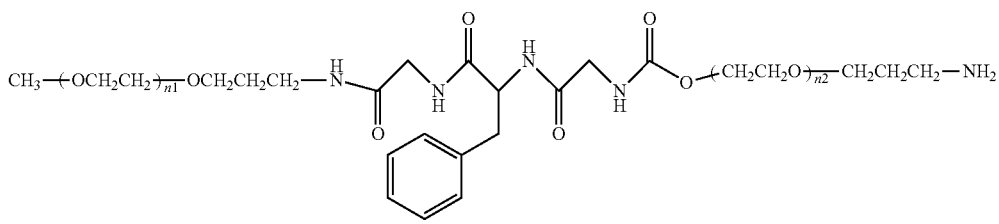

n1 = about 480, n2 = about 450

By the same production method as in Example 4 and using glycine-L-phenylalanine-glycine with the N terminal protected by a 9-fluorenylmethyloxycarbonyl group (Fmoc group) (Fmoc-Gly-Phe-Gly) as the starting material, the above-mentioned compound (p30) (ME-200GFG-200PA) was obtained. yield 1.1 g. The molecular weight is shown in Table 1. HPLC: amine purity 89%.

NMR ($d_6$-DMSO): 1.62 ppm (m, 4H, —CO—NH—CH$_2$—CH$_2$—CH$_2$—O—(CH$_2$—CH$_2$—O)n-CH$_3$, —CH$_2$—CH$_2$—CH$_2$—NH$_2$), 2.80 ppm (m, 1H), 3.10 ppm (m, 2H), 3.23 ppm (s, 3H, —O—(CH$_2$—CH$_2$—O)n-CH$_3$), 3.60 ppm (m, about 3,800H, —NH—CH$_2$—CH$_2$—CH$_2$—O—(CH$_2$—CH$_2$—O)n-CH$_3$, —NH—CO—O—CH$_2$—CH$_2$—O—(CH$_2$—CH$_2$—O)n-CH$_2$—CH$_2$—), 4.05 ppm (m, 2H), 4.47 ppm (m, 1H), 7.20 ppm (m, 5H, —NH—CO—CH—CH$_2$—C$_6$H$_5$), 7.34 ppm (broad, 1H), 7.64 ppm (broad, 1H), 8.10 ppm (broad, 1H), 8.30 ppm (broad, 1H)

Example 11

Synthesis of Compound (p31)
(ME-200GF-200PA(amide))

By the same production method as in Example 7 and using L-phenylalanyl-glycine with the N terminal protected by a 9-fluorenylmethyloxycarbonyl group (Fmoc group) (Fmoc-Phe-Gly), and heterobifunctional PEG having a propylamino group protected by a tert-butoxycarbonyl group at one terminal and hexanoate N-succinimidyl active ester at the other terminal (average molecular weight=about 21,000, "SUNBRIGHT BO-200HS" manufactured by NOF CORPORATION) as the starting materials, the above-mentioned compound (p31) (ME-200GF-200PA(amide)) into which heterobifunctional PEG was introduced by an amide bond rather than the urethane bond in Example 7 was obtained. yield 1.0 g. The molecular weight is shown in Table 1. HPLC: amine purity 91%.

NMR ($d_6$-DMSO): 1.11 ppm (m, 2H, —NH—CO—CH$_2$—CH$_2$—CH$_2$—CH$_2$—CH$_2$—O—(CH$_2$—CH$_2$—O)n-), 1.38 ppm (m, 2H, —NH—CO—CH$_2$—CH$_2$—CH$_2$—CH$_2$—CH$_2$—O—(CH$_2$—CH$_2$—O)n-), 1.62 ppm (m, 6H, —NH—CO—CH$_2$—CH$_2$—CH$_2$—CH$_2$—CH$_2$—O—(CH$_2$—CH$_2$—O)n-, —CO—NH—CH$_2$—CH$_2$—O—(CH$_2$—CH$_2$—O)n-CH$_3$, —CH$_2$—CH$_2$—CH$_2$—NH$_2$), 2.02 ppm (m, 2H, —NH—CO—CH$_2$—CH$_2$—CH$_2$—CH$_2$—CH$_2$—O—(CH$_2$—CH$_2$—O)n-), 2.80 ppm (m, 1H), 3.10 ppm (m, 2H), 3.23 ppm (s, 3H, —O—(CH$_2$—CH$_2$—O)n-CH$_3$), 3.60 ppm (m, about 3,800H, —NH—CH$_2$—CH$_2$—CH$_2$—O—(CH$_2$—CH$_2$—O)n-CH$_3$, —NH—CO—O—CH$_2$—CH$_2$—O—(CH$_2$—CH$_2$—O)n-CH$_2$—CH$_2$—), 4.47 ppm (m, 1H), 7.20 ppm (m, 5H, —NH—CO—CH—CH$_2$—C$_6$H$_5$), 7.26 ppm (broad, 1H), 7.64 ppm (broad, 1H), 8.10 ppm (broad, 1H), 8.30 ppm (broad, 1H)

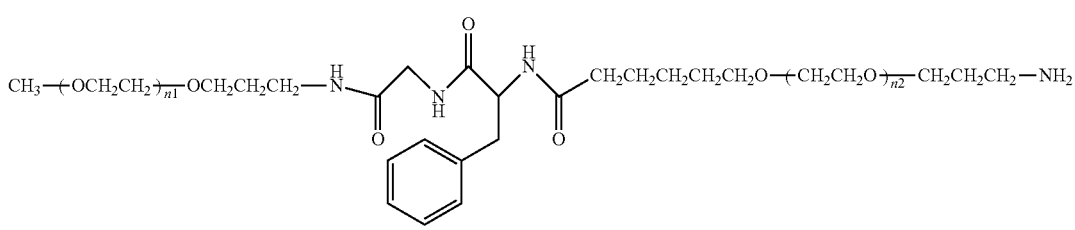

n1 = about 480, n2 = about 450

Example 12

Synthesis of Compound (p32) (ME-200GLFG (SEQ ID NO: 4) (D)-200PA)

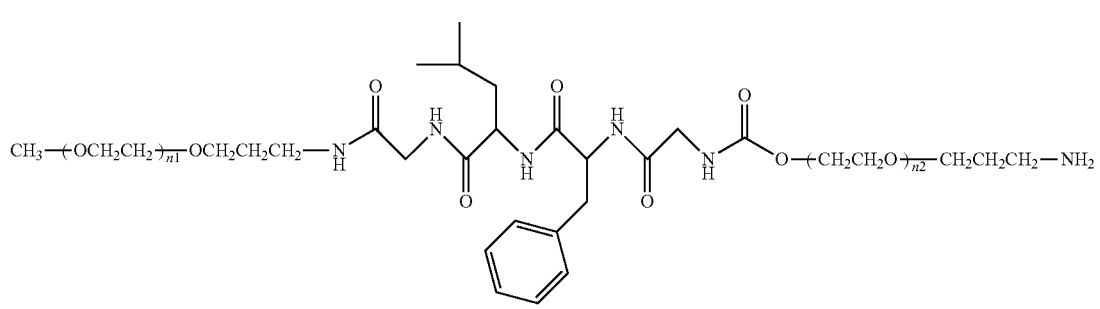

(p32)

n1 = about 480, n2 = about 450

By the same production method as in Example 1 and using glycine-D-phenylalanine-D-leucine-glycine (SEQ ID NO: 4) with the N terminal protected by a tert-butoxycarbonyl group (Boc group) as the starting material, the above-mentioned compound (p32) (ME-200GLFG (SEQ ID NO: 4) (D)-200PA) having a D-type amino acid which is an optical isomer was obtained. yield 1.1 g. The molecular weight is shown in Table 1. HPLC: amine purity 93%.

NMR (CDCl$_3$): 0.90 ppm (t, 6H, —NH—CO—CH—CH$_2$—CH(CH$_3$)$_2$), 1.48 ppm (broad, 1H), 1.62 ppm (t, 1H), 1.71 ppm (m, 1H), 1.82 ppm (m, 2H), 3.12 ppm (m, 2H), 3.19 ppm (d, 2H), 3.34 ppm (m, 2H), 3.38 ppm (s, 3H, —CO—NH—CH$_2$—CH$_2$—CH$_2$—O—(CH$_2$—CH$_2$—O)n—CH$_3$), 3.64 ppm (m, about 3,800H, —NH—CH$_2$—CH$_2$—CH$_2$—O—(CH$_2$—CH$_2$—O)n-CH$_3$, —NH—CO—O—CH$_2$—CH$_2$—O—(CH$_2$—CH$_2$—O)n-CH$_2$—CH$_2$—), 4.10 ppm (m, 2H), 4.34 ppm (m, 1H), 4.50 ppm (q, 1H), 6.46 ppm (broad, 1H), 6.94 ppm (broad, 1H), 7.08 ppm (broad, 1H), 7.27 ppm (m, 5H, —NH—CO—CH—CH$_2$—C$_6$H$_5$)

Example 13

Synthesis of Compound (p34) (LY-(ME-100GLFG (SEQ ID NO: 4) (L)-100)$_2$-PA)

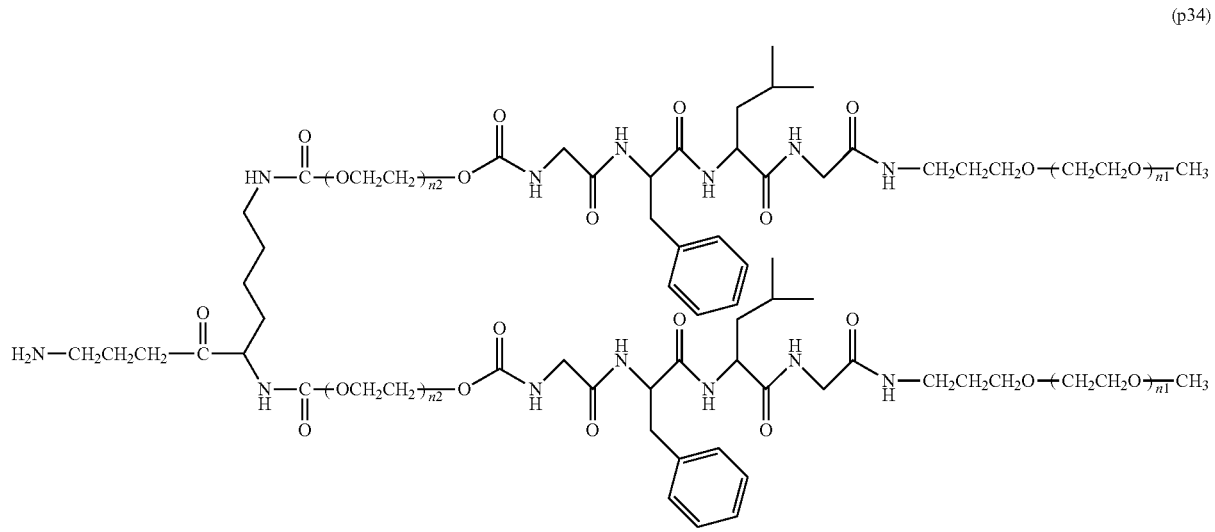

(p34)

n1 = about 205, n2 = about 205

Example 13-1

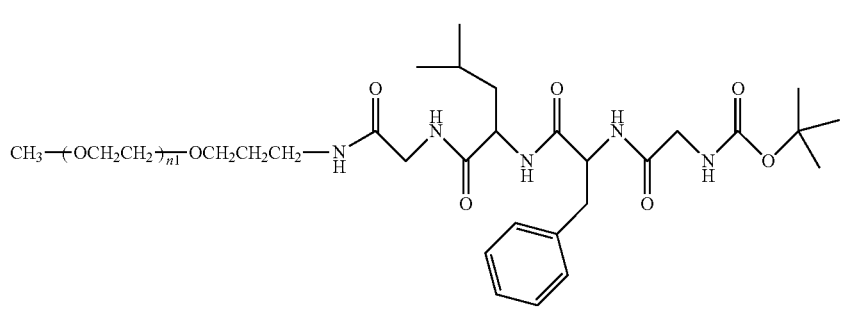

(p35)

n1 = about 205

Glycyl-L-phenylalanyl-L-leucyl-glycine (SEQ ID NO: 4) with the N terminal protected by a tert-butoxycarbonyl group (Boc group) (Boc-Gly-Phe-Leu-Gly (SEQ ID NO: 4)) (0.438 g, $8.8 \times 10^{-4}$ mol, manufactured by GenScript Biotech) and N-hydroxysuccinimide (0.128 g, $1.1 \times 10^{-3}$ mol, manufactured by Midori Kagaku Co., Ltd.) were dissolved in dehydrated N,N'-dimethylformamide (1.0 g), N,N'-dicyclohexylcarbodiimide (0.229 g, $1.1 \times 10^{-3}$ mol, manufactured by Tama Kagaku Kogyo Co., Ltd.) was added, and the mixture was reacted at room temperature under a nitrogen atmosphere for 1 hr. Dehydrated N,N'-dimethylformamide (3.0 g) was added to dilute the mixture, methoxy PEG having a propylamino group at the terminal (2.0 g, $2.2 \times 10^{-4}$ mol, average molecular weight=about 9,000, "SUNBRIGHT MEPA-10T" manufactured by NOF CORPORATION) was added, and the mixture was reacted at room temperature under a nitrogen atmosphere for 1 hr. Thereafter, the reaction mixture was diluted with ethyl acetate (20 g), and suction filtration was performed using a Kiriyama funnel lined with LS100 filter paper. Ethyl acetate (30 g) was added to the filtrate, and the mixture was stirred to uniformity. Hexane (25 g) was added, and the mixture was stirred at room temperature for 15 min. The resultant product was precipitated and suction filtered using 5A filter paper. The precipitate was recovered, dissolved again in ethyl acetate (50 g), hexane (25 g) was added, and the mixture was stirred at room temperature for 15 min. The resultant product was precipitated and suction filtered using 5A filter paper. The precipitate was recovered, washed with hexane (25 g), suction filtered using 5A filter paper, and dried in vacuo to give the above-mentioned compound (p35) (ME-100GLFG (SEQ ID NO: 4) (L)-Boc). yield 1.8 g.

NMR (CDCl$_3$): 0.89 ppm (d, 3H, —NH—CO—CH—CH$_2$—CH(CH$_3$)$_2$), 0.92 ppm (d, 3H, —NH—CO—CH—CH$_2$—CH(CH$_3$)$_2$), 1.36 ppm (s, 9H, —NH—CO—O—C(CH$_3$)$_3$) 1.48 ppm (m, 1H, —NH—CO—CH—CH$_2$—CH(CH$_3$)$_2$), 1.55 ppm (m, 1H, —NH—CO—CH—CH$_2$—CH(CH$_3$)$_2$), 1.80 ppm (m, 3H), 3.13 ppm (dd, 1H, —NH—CO—CH—CH$_2$—C$_6$H$_5$), 3.21 ppm (dd, 1H, —NH—CO—CH—CH$_2$—C$_6$H$_5$), 3.33 ppm (m, 2H, —CO—NH—CH$_2$—CH$_2$—CH$_2$—O—(CH$_2$—CH$_2$—O)n-CH$_3$), 3.38 ppm (s, 3H, —CO—NH—CH$_2$—CH$_2$—CH$_2$—O—(CH$_2$—CH$_2$—O)n-CH$_3$), 3.65 ppm (m, about 820H, —CO—NH—CH$_2$—CH$_2$—CH$_2$—O—(CH$_2$—CH$_2$—O)n-CH$_3$), 3.91 ppm (t, 1H, —NH—CO—CH—CH$_2$—CH(CH$_3$)$_2$), 4.43 ppm (broad, 1H), 4.55 ppm (q, 1H, —NH—CO—CH—CH$_2$—C$_6$H$_5$), 5.77 ppm (broad, 1H), 6.76 ppm (broad, 1H), 6.86 ppm (broad, 1H), 6.90 ppm (broad, 1H), 7.14 ppm (broad, 1H), 7.20 ppm (d, 2H, —NH—CO—CH—CH$_2$—C$_6$H$_5$), 7.32 ppm (m, 3H, —NH—CO—CH—CH$_2$-C$_6$H$_5$)

Example 13-2

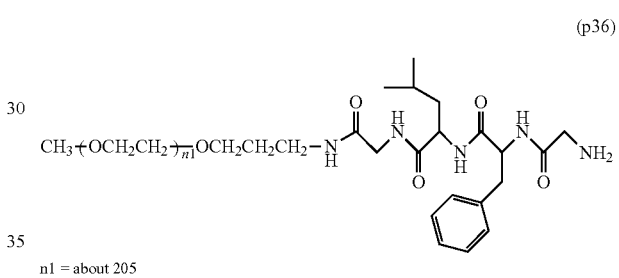

(p36)

n1 = about 205

ME-100GLFG (SEQ ID NO: 4) (L)-Boc (1.8 g, $2.0 \times 10^{-4}$ mol) obtained in Example 13-1 was dissolved in dichloromethane (9.0 g), methanesulfonic acid (1.3 mL, $2.0 \times 10^{-2}$ mol, manufactured by KANTO CHEMICAL CO., INC.) was added, and the mixture was reacted at room temperature under a nitrogen atmosphere for 2 hr. Thereafter, the reaction mixture was diluted with toluene (18 g), ion exchange water (18 g) was added, and the mixture was stirred at room temperature for 15 min. The resultant product was extracted into the aqueous layer. An appropriate amount of 1 mol/L aqueous sodium hydroxide solution was added to the obtained aqueous layer to adjust the pH to 12, and sodium chloride (4.5 g) was dissolved. Chloroform (18 g) was added thereto, and the mixture was stirred at room temperature for 15 min. The resultant product was extracted into the organic layer. The aqueous layer and the organic layer were separated, chloroform (18 g) was added again to the aqueous layer, and the mixture was stirred at room temperature for 15 min. The resultant product was extracted into the organic layer. The organic layer obtained by the first and the second extraction was concentrated at 40° C., and ethyl acetate (36 g) was added to the obtained concentrate. Sodium sulfate (0.90 g) was added to the obtained ethyl acetate solution, and the mixture was stirred at 30° C. for 15 min, and suction filtration was performed using a Kiriyama funnel lined with Oplite on 5A filter paper. Hexane (18 g) was added to the obtained filtrate, and the mixture was stirred at room temperature for 15 min. The resultant product was precipitated and suction filtered using 5A filter paper. The precipitate was washed with hexane (18 g), suction filtered using 5A filter paper, and dried in vacuo to give the above-mentioned compound (p36) (ME-100GLFG (SEQ ID NO: 4) (L)-NH$_2$). yield 1.4 g.

NMR (CDCl$_3$): 0.89 ppm (d, 3H, —NH—CO—CH—CH$_2$—CH(C$\underline{H}_3$)$_2$), 0.91 ppm (d, 3H, —NH—CO—CH—CH$_2$—CH(C$\underline{H}_3$)$_2$), 1.53 ppm (m, 2H, —NH—CO—CH—C$\underline{H}_2$—CH(CH$_3$)$_2$), 1, 70 ppm (m, 1H, —NH—CO—CH—C$\underline{H}_2$—CH(CH$_3$)$_2$), 1.80 ppm (m, 2H, —CO—NH—CH$_2$—C$\underline{H}_2$—CH$_2$—O—(CH$_2$—CH$_2$—O)n-CH$_3$), 3.10 ppm (dd, 1H, —NH—CO—CH—C$\underline{H}_2$—C$_6$H$_5$), 3.18 ppm (dd, 1H, —NH—CO—CH—C$\underline{H}_2$—C$_6$H$_5$), 3.33 ppm (m, 7H), 3.74 ppm (m, about 820$\underline{H}$, —CO—NH—CH$_2$—CH$_2$—CH$_2$—O—(C$\underline{H}_2$—C$\underline{H}_2$—O)n-CH$_3$), 4.31 ppm (broad, 1H), 4.55 ppm (t, 1H, —NH—CO—C$\underline{H}$—CH$_2$—C$_6$H$_5$), 6.91 ppm (broad, 1H), 7.00 ppm (broad, 1H), 7.28 ppm (m, 5H, —NH—CO—CH—CH$_2$—C$_\underline{6}\underline{H}_5$), 7.98 ppm (broad, 1H)

Example 13-3

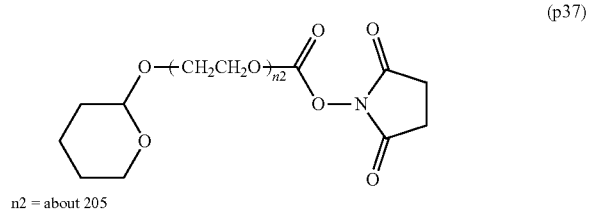

(p37)

n2 = about 205 filtered using 5A filter paper. To the obtained filtrate was added 2,6-di-tert-butyl-p-cresol (4.3 mg) and the mixture was stirred for 5 min. Thereafter, 5 wt % aqueous sodium chloride solution (6 g, pH 5) was added, and the mixture was stirred at room temperature for 15 min for washing. The aqueous layer and the organic layer were separated, magnesium sulfate (1.0 g) was added to the organic layer, the mixture was stirred at room temperature for 30 min, and suction filtration was performed using a Kiriyama funnel lined with Oplite on 5A filter paper. The obtained filtrate was concentrated at 35° C., and the obtained concentrate was dissolved in ethyl acetate (50 g). After dissolution, hexane (25 g) was added, and the mixture was stirred at room temperature for 30 min. The resultant product was precipitated and suction filtered using 5A filter paper. Hexane (25 g) was added to the obtained precipitate and the mixture was stirred for 30 min, suction filtered using 5A filter paper, and dried in vacuo to give the above-mentioned compound (p37) (THP-10TS). yield 4.3 g.

NMR (CDCl$_3$): 1.52 ppm (m, 2H, -tetrahydropyranyl), 1.59 ppm (m, 2H, -tetrahydropyranyl), 1.73 ppm (m, 1H, -tetrahydropyranyl), 1.85 ppm (m, 1H, -tetrahydropyranyl), 2.85 ppm (t, 4H, -succinimide), 3.64 ppm (m, about 820H, —NH—CH$_2$—CH$_2$—CH$_2$—O—(CH$_2$—CH$_2$—O)n-CH$_3$, —NH—CO—O—CH$_2$—CH$_2$—O—(CH$_2$—CH$_2$—O)n-CH$_2$—CH$_2$—), 3.80 ppm (m, 2H), 3.88 ppm (m, 2H, -tetrahydropyranyl), 4.47 ppm (m, 2H), 4.64 ppm (t, 1H, -tetrahydropyranyl)

Example 13-4

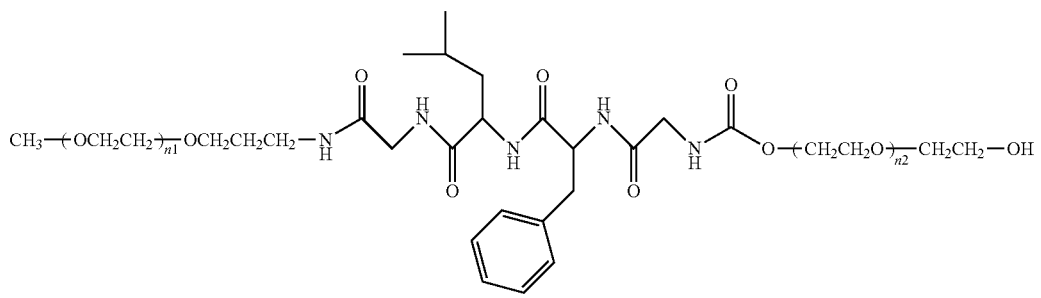

(p38)

n1 = about 205, n2 = about 205

Heterobifunctional PEG having a tetrahydropyranyl group at one terminal and a hydroxy group at one terminal (5 g, 6.0×10$^{-5}$ mol), synthesized using the production method described in non-patent document (Bioconjugate Chem., 21(2010), pp. 248-254) and the like, was dissolved in dichloromethane (12 g), di(N-succinimidyl) carbonate (0.513 g, 2.0×10$^{-3}$ mol, manufactured by Tokyo Chemical Industry Co., Ltd.) and pyridine (243 μL, 3.0×10$^{-3}$ mol, manufactured by KANTO CHEMICAL CO., INC.) were added, and the mixture was reacted at 27° C. under a nitrogen atmosphere for 7 hr. Thereafter, the reaction mixture was diluted with dichloromethane (20 g), and suction ME-100GLFG (SEQ ID NO: 4) (L)-NH$_2$ (3.64 g, 3.4×10$^{-4}$ mol) obtained in Example 13-2 was dissolved in chloroform (17 g), triethylamine (56.5 μL, 4.1×10$^{-4}$ mol, KANTO CHEMICAL CO., INC.) and THP-10TS obtained in Example 13-3 (2.80 g, 3.1×10$^{-4}$ mol) were added, and the mixture was reacted at room temperature under a nitrogen atmosphere for 2 hr. After the reaction, the mixture was concentrated at 40° C., the obtained concentrate was dissolved in 0.1 mol/L aqueous sodium citrate solution (120 g, pH 2.5), and the mixture was reacted at room temperature under a nitrogen atmosphere for 4 hr. After the reaction, chloroform (50 g) and 2,6-di tert butyl-p-cresol (5.0 mg)

were added and the mixture was stirred for 10 min. The aqueous layer and the organic layer were separated, magnesium sulfate (3.2 g) was added to the organic layer and the mixture was stirred at 40° C. for 30 min, and suction filtration was performed using a Kiriyama funnel lined with Oplite on 5A filter paper. The obtained filtrate was concentrated, and the obtained concentrate was dissolved in ethyl acetate (50 g). After dissolution, hexane (25 g) was added, and the mixture was stirred at room temperature for 15 min. The resultant product was precipitated and suction filtered using 5A filter paper. Hexane (25 g) was added to the obtained precipitate and the mixture was stirred for 15 min, suction filtered using 5A filter paper, and dried in vacuo to give the above-mentioned compound (p38) (ME-100GLFG (SEQ ID NO: 4) (L)-100HO). yield 5.30 g.

NMR (CDCl$_3$): 0.90 ppm (t, 6H, —NH—CO—CH—CH$_2$—CH(C$\underline{H_3}$)$_2$), 1.48 ppm (broad, 1H), 1.62 ppm (t, 1H), 1.71 ppm (m, 1H), 1.82 ppm (m, 2H), 3.19 ppm (d, 2H), 3.34 ppm (m, 2H), 3.38 ppm (s, 3H, —CO—NH—CH$_2$—CH$_2$—CH$_2$—O—(CH$_2$—CH$_2$—O)n-C$\underline{H_3}$), 3.64 ppm (m, about 820H, —NH—CH$_2$—CH$_2$—CH$_2$—O—(C$\underline{H_2}$—C$\underline{H_2}$—O)n-CH$_3$, —NH—CO—O—CH$_2$—CH$_2$—O—(C$\underline{H_2}$—C$\underline{H_2}$—O)n-CH$_2$—CH$_2$—), 4.10 ppm (m, 2H), 4.34 ppm (m, 1H), 4.50 ppm (q, 1H), 6.46 ppm (broad, 1H), 6.94 ppm (broad, 1H), 7.08 ppm (broad, 1H), 7.27 ppm (m, 5H, —NH—CO—CH—CH$_2$—C$\underline{_6H_5}$)

Example 13-5

ME-100GLFG (SEQ ID NO: 4) (L)-100HO (5.0 g, 2.8×10$^{-4}$ mol) obtained in Example 13-4 was dissolved in dichloromethane (12 g), di(N-succinimidyl) carbonate (0.285 g, 1.1×10$^{-3}$ mol, manufactured by Tokyo Chemical Industry Co., Ltd.) and pyridine (135 μL, 1.7×10$^{-3}$ mol, manufactured by KANTO CHEMICAL CO., INC.) were added, and the mixture was reacted at 27° C. under a nitrogen atmosphere for 7 hr. Thereafter, the reaction mixture was diluted with dichloromethane (20 g), and suction filtered using 5A filter paper. To the obtained filtrate was added 2,6-di tert butyl:4-p-cresol (4.3 mg), and the mixture was stirred for 5 min. Thereafter, 5 wt % aqueous sodium chloride solution (6 g, pH 5) was added, and the mixture was stirred at room temperature for 15 min for washing. The aqueous layer and the organic layer were separated, magnesium sulfate (1.0 g) was added to the organic layer, and the mixture was stirred at room temperature for 30 min, and suction filtration was performed using a Kiriyama funnel lined with Oplite on 5A filter paper. The obtained filtrate was concentrated at 35° C., the obtained concentrate was dissolved in ethyl acetate (50 g). After dissolution, hexane (25 g) was added, and the mixture was stirred at room temperature for 30 min. The resultant product was precipitated and suction filtered using 5A filter paper. Hexane (25 g) was added to the obtained precipitate, and the mixture was stirred for 30 min, suction filtered using 5A filter paper, and dried in vacuo to give the above-mentioned compound (p39) (ME-100GLFG (SEQ ID NO: 4) (L)-100TS). yield 4.2 g.

NMR (CDCl$_3$): 0.90 ppm (t, 6H, —NH—CO—CH—CH$_2$—CH(C$\underline{H_3}$)$_2$), 1.44 ppm (s, 9H, —CH$_2$—CH$_2$—CH$_2$—NH—CO—O—C(C$\underline{H_3}$)$_3$), 1.64 ppm (m, 1H), 1.76 ppm (m, 5H), 2.85 ppm (t, 4H, -succinimide), 3.20 ppm (m, 4H), 3.33 ppm (m, 2H, —CO—NH—CH$_2$—CH$_2$—CH$_2$—O—(CH$_2$—CH$_2$—O)n-CH$_3$), 3.38 ppm (s, 3H, —CO—NH—CH$_2$—CH$_2$—CH$_2$—O—(CH$_2$—CH$_2$—O)n-C$\underline{H_3}$), 3.64 ppm (m, about 820H, —NH—CH$_2$—CH$_2$—CH$_2$—O—(C$\underline{H_2}$—C$\underline{H_2}$—O)n-CH$_3$, —NH—CO—O—CH$_2$—CH$_2$—O—(C$\underline{H_2}$—C$\underline{H_2}$—O)n-CH$_2$—CH$_2$—), 4.10 ppm (m, 2H, —NH—CO—O—C$\underline{H_2}$—CH$_2$—O—(CH$_2$—CH$_2$—O)n-CH$_2$—CH$_2$—), 4.32 ppm (m, 1H), 4.50 ppm (q, 1H), 5.02 ppm (broad, 1H), 6.45 ppm (broad, 1H), 6.93 ppm (broad, 1H), 7.06 ppm (broad, 1H), 7.13 ppm (broad, 1H), 7.27 ppm (m, 5H, —NH—CO—CH—CH$_2$—C$\underline{_6H_5}$)

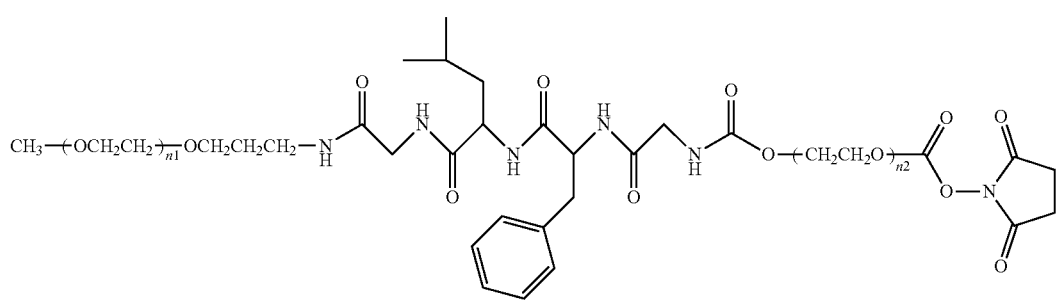

(p39)

n1 = about 205, n2 = about 205

Example 13-6

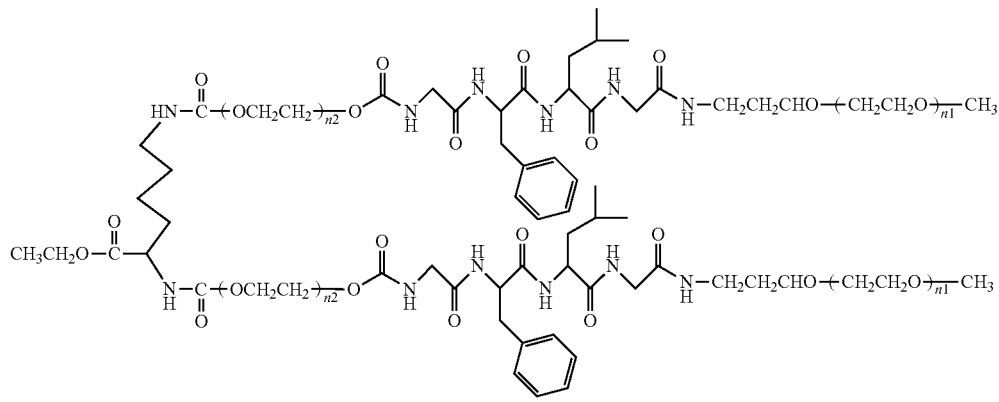

n1 = about 205, n2 = about 205

ME-100GLFG (SEQ ID NO: 4) (L)-100TS (3.6 g, 2.0× $10^{-4}$ mol) obtained in Example 13-5 was dissolved in N,N'-dimethylformamide (7.0 g), L-lysine ethyl ester 2 hydrochloride (26 mg, $1.1\times10^{-4}$ mol, manufactured by Sigma Ltd. Aldrich) and triethylamine (73 mg, $7.2\times10^{-4}$ mol) were added, and the mixture was reacted under a nitrogen atmosphere at 40° C. for 5 hr. The reaction mixture was diluted with ethyl acetate (36 g), and suction filtration was performed using a Kiriyama funnel lined with 5A filter paper. Hexane (18 g) was added to the obtained filtrate, and the mixture was stirred at room temperature for 15 min. The resultant product was precipitated and suction filtered using 5A filter paper. The precipitate was washed with hexane (18 g), suction filtered using 5A filter paper, and dried in vacuo to give the above-mentioned compound (p40) (LY-(ME-100GLFG (SEQ ID NO: 4) (L)-100)$_2$-CE). yield 3.1 g.

NMR (CDCl$_3$): 0.90 ppm (t, 6H, —NH—CO—CH—CH$_2$—CH(C$\underline{H}_3$)$_2$), 1.28 ppm (t, 3H, —CO—O—CH$_2$—C$\underline{H}_3$), 1.36 ppm (m, 2H), 1.48 ppm (broad, 1H), 1.52 ppm (m, 2H), 1.62 ppm (t, 1H), 1.70 ppm (m, 2H), 1.82 ppm (m, 3H), 3.15 ppm (q, 2H), 3.19 ppm (d, 2H), 3.34 ppm (m, 2H), 3.38 ppm (s, 6H, —CO—NH—CH$_2$—CH$_2$—CH$_2$—O—(CH$_2$—CH$_2$—O)n-C$\underline{H}_3$), 3.64 ppm (m, about 1,600H, —NH—CH$_2$—CH$_2$—CH$_2$—O—(C$\underline{H}_2$—C$\underline{H}_2$—O)n-CH$_3$, —NH—CO—O—CH$_2$—CH$_2$—O—(C$\underline{H}_2$—C$\underline{H}_2$—O)n-CH$_2$—CH$_2$—), 4.10 ppm (m, 2H), 4.21 ppm (m, 6H), 4.34 ppm (m, 2H), 4.50 ppm (q, 1H), 4.90 ppm (broad, 1H), 5.37 ppm (d, 1H), 6.46 ppm (broad, 1H), 6.94 ppm (broad, 1H), 7.08 ppm (broad, 1H), 7.27 ppm (m, 5H, —NH—CO—CH—CH$_2$—C$_6$$\underline{H}_5$)

Example 13-7

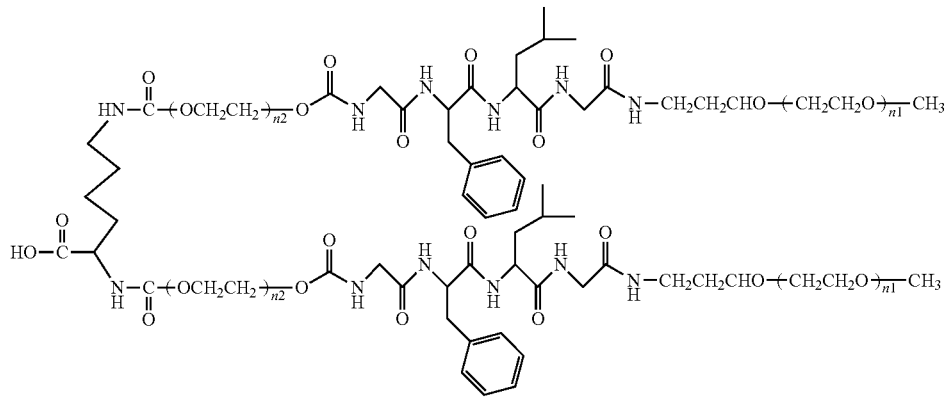

n1 = about 205, n2 = about 205

LY-(ME-100GLFG (SEQ ID NO: 4) (L)-100)$_2$-CE (1.8 g, $5.0\times10^{-5}$ mol) obtained in Example 13-6 was dissolved in 0.13 mol/L aqueous sodium hydroxide solution (18 g), and the mixture was reacted under a nitrogen atmosphere at room temperature for 3 hr. Sodium chloride (4.5 g) was dissolved in the reaction mixture, the pH of the aqueous layer was adjusted to 8.5 with 85% phosphoric acid, dichloromethane (11 g) was added thereto, and the mixture was stirred at room temperature for 15 min. The resultant product was extracted into the organic layer. The aqueous layer and the organic layer were separated, dichloromethane (11 g) was added again to the aqueous layer, and the mixture was stirred at room temperature for 15 min. The resultant product was extracted into the organic layer. The organic layer obtained by the first and the second extraction was concentrated at 40° C., and ethyl acetate (36 g) was added to the obtained concentrate. Magnesium sulfate (0.90 g) was added to the obtained ethyl acetate solution, and the mixture was stirred at 30° C. for 30 min, and suction filtration was performed using a Kiriyama funnel lined with Oplite on 5A filter paper. Hexane (18 g) was added to the obtained filtrate, and the mixture was stirred at room temperature for 15 min. The resultant product was precipitated and suction filtered using 5A filter paper. The precipitate was washed with hexane (18 g), suction filtered using 5A filter paper, and dried in vacuo to give the above-mentioned compound (p41) (LY-(ME-100GLFG (SEQ ID NO: 4) (L)-100)$_2$—C2). yield 1.4 g.

NMR (CDCl$_3$): 0.90 ppm (t, 6H, —NH—CO—CH—CH$_2$—CH(CH$_3$)$_2$), 1.36 ppm (m, 2H), 1.48 ppm (broad, 1H), 1.52 ppm (m, 2H), 1.62 ppm (t, 1H), 1.70 ppm (m, 2H), 1.82 ppm (m, 3H), 3.15 ppm (m, 2H), 3.19 ppm (d, 2H), 3.34 ppm (m, 2H), 3.38 ppm (s, 6H, —CO—NH—CH$_2$—CH$_2$—CH$_2$—O—(CH$_2$—CH$_2$—O)n-CH$_3$), 3.64 ppm (m, about 1,600H, —NH—CH$_2$—CH$_2$—CH$_2$—O—(CH$_2$—CH$_2$—O)n-CH$_3$, —NH—CO—O—CH$_2$—CH$_2$—O—(CH$_2$—CH$_2$—O)n-CH$_2$—CH$_2$—), 4.10 ppm (m, 2H), 4.21 ppm (m, 4H), 4.34 ppm (m, 2H), 4.50 ppm (q, 1H), 4.90 ppm (broad, 1H), 5.37 ppm (d, 1H), 6.46 ppm (broad, 1H), 6.94 ppm (broad, 1H), 7.08 ppm (broad, 1H), 7.27 ppm (m, 5H, —NH—CO—CH—CH$_2$—C$_6$H$_5$)

Example 13-8

4.0×10$^{-5}$ mol) obtained in Example 13-7 and 2,6-di-tert-butyl-p-cresol (1.2 mg) were dissolved in toluene (6.0 g), N-hydroxysuccinimide (16 mg, 1.4×10$^{-4}$ mol) and 1,3-dicyclohexylcarbodiimide (20 mg, 1.0×10$^{-4}$ mol) were added, and the mixture was reacted under a nitrogen atmosphere at 40° C. for 4 hr. Then, N-(tert-butoxycarbonyl)-1,3-diaminopropane was added, and the mixture was reacted under a nitrogen atmosphere at 40° C. for 4 hr. The reaction mixture was diluted with toluene (12 g), and suction filtration was performed using a Kiriyama funnel lined with Oplite on 5A filter paper. The obtained filtrate was diluted with ethyl acetate (18 g), hexane (18 g) was added, and the mixture was stirred at room temperature for 15 min. The resultant product was precipitated and suction filtered using 5A filter paper. The precipitate was washed with hexane (18 g), suction filtered using 5A filter paper, and dried in vacuo to give the above-mentioned compound (p42) (LY-(ME-100GLFG (SEQ ID NO: 4) (L)-100)$_2$-Boc). yield 1.1 g.

NMR (CDCl$_3$): 0.90 ppm (t, 6H, —NH—CO—CH—CH$_2$—CH(CH$_3$)$_2$), 1.36 ppm (m, 2H), 1.44 ppm (s, 9H), 1.48 ppm (broad, 1H), 1.52 ppm (m, 2H), 1.62 ppm (m, 3H), 1.70 ppm (m, 2H), 1.82 ppm (m, 3H), 3.15 ppm (m, 4H), 3.19 ppm (d, 2H), 3.29 ppm (m, 2H), 3.34 ppm (m, 2H), 3.38 ppm (s, 6H, —CO—NH—CH$_2$—CH$_2$—CH$_2$—O—(CH$_2$—CH$_2$—O)n-CH$_3$), 3.64 ppm (m, about 1,600H, —NH—CH$_2$—CH$_2$—CH$_2$—O—(CH$_2$—CH$_2$—O)n-CH$_3$, —NH—CO—O—CH$_2$—CH$_2$—O—(CH$_2$—CH$_2$—O)n-CH$_2$—CH$_2$—), 4.10 ppm (m, 3H), 4.21 ppm (m, 4H), 4.34 ppm (m, 1H), 4.50 ppm (q, 1H), 5.08 ppm (broad, 1H), 5.56 ppm (d, 1H), 6.46 ppm (broad, 1H), 6.94 ppm (broad, 1H), 7.08 ppm (broad, 1H), 7.27 ppm (m, 5H, —NH—CO—CH—CH$_2$—C$_6$H$_5$)

(p42)

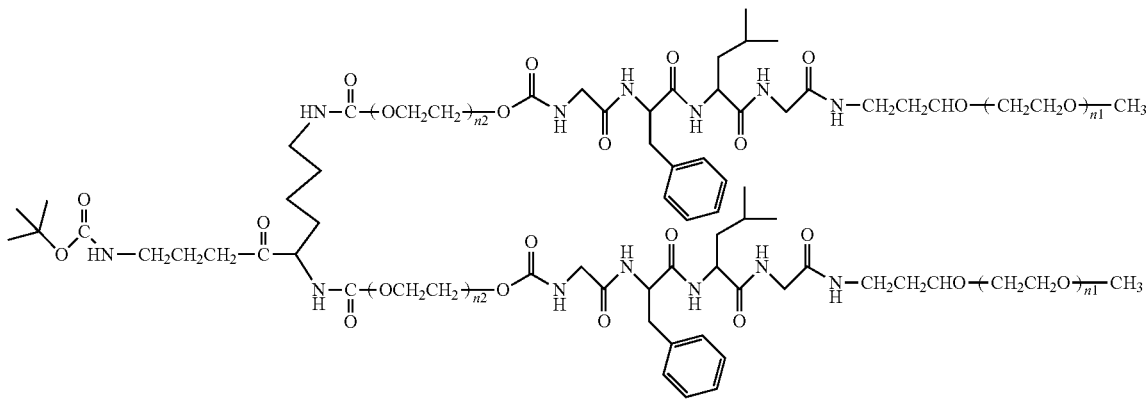

n1 = about 205, n2 = about 205

Example 13-9

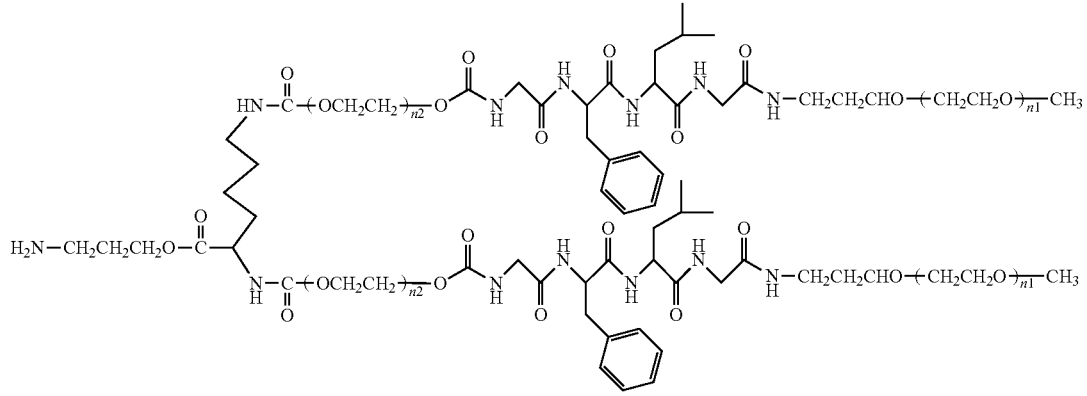
(p34)

n1 = about 205, n2 = about 205

LY-(ME-100GLFG (SEQ ID NO: 4) (L)-100)$_2$-Boc (0.90 g, 2.5×10$^{-5}$ mol) obtained in Example 13-8 was dissolved in dichloromethane (4.5 g), methanesulfonic acid (162 μL, 2.5×10$^{-3}$ mol) was added, and the mixture was reacted under a nitrogen atmosphere at room temperature for 2 hr. The reaction mixture was diluted with toluene (9.0 g), ion exchange water (23 g) was added, and the mixture was stirred at room temperature for 15 min. The resultant product was extracted into the aqueous layer. Thereafter, the aqueous layer was washed with a mixed solution of toluene and chloroform, whereby polyethylene glycol impurity without an amino group was removed. An appropriate amount of 1 mol/L aqueous sodium hydroxide solution was added to the aqueous layer to adjust the pH to 12, and sodium chloride (2.3 g) was dissolved. Chloroform (9.0 g) was added thereto, and the mixture was stirred at room temperature for 15 min. The resultant product was extracted into the organic layer. The aqueous layer and the organic layer were separated, chloroform (9.0 g) was added again to the aqueous layer, and the mixture was stirred at room temperature for 15 min. The resultant product was extracted into the organic layer. The organic layer obtained by the first and the second extraction was concentrated at 40° C., and ethyl acetate (36 g) was added to the obtained concentrate. Sodium sulfate (0.90 g) was added to the obtained ethyl acetate solution, and the mixture was stirred at 30° C. for 30 min, and suction filtration was performed using a Kiriyama funnel lined with Oplite on 5A filter paper. Hexane (18 g) was added to the obtained filtrate, and the mixture was stirred at room temperature for 15 min. The resultant product was precipitated and suction filtered using 5A filter paper. The precipitate was washed with hexane (18 g), suction filtered using 5A filter paper, and dried in vacuo to give the above-mentioned compound (p34) (LY-(ME-100GLFG (SEQ ID NO: 4) (L)-100)$_2$-PA). yield 0.8 g. The molecular weight is shown in Table 1. HPLC: amine purity 92%.

NMR (CDCl$_3$): 0.90 ppm (t, 6H, —NH—CO—CH—CH$_2$—CH(CH$_3$)$_2$), 1.37 ppm (m, 2H), 1.48 ppm (broad, 1H), 1.52 ppm (m, 2H), 1.62 ppm (m, 3H), 1.70 ppm (m, 2H), 1.82 ppm (m, 3H), 2.84 ppm (m, 2H), 3.15 ppm (m, 2H), 3.19 ppm (d, 2H), 3.34 ppm (m, 2H), 3.38 ppm (s, 6H, —CO—NH—CH$_2$—CH$_2$—CH$_2$—O—(CH$_2$—CH$_2$—O)n-CH$_3$), 3.64 ppm (m, about 1,600H, —NH—CH$_2$—CH$_2$—CH$_2$—O—(CH$_2$—CH$_2$—O)n-CH$_3$, —NH—CO—O—CH$_2$—CH$_2$—O—(CH$_2$—CH$_2$—O)n-CH$_2$—CH$_2$—), 4.10 ppm (m, 3H), 4.21 ppm (m, 4H), 4.34 ppm (m, 1H), 4.50 ppm (q, 1H), 5.58 ppm (broad, 1H), 6.46 ppm (broad, 1H), 6.94 ppm (broad, 1H), 7.08 ppm (broad, 1H), 7.27 ppm (m, 5H, —NH—CO—CH—CH$_2$—C$_6$H$_5$)

Comparative Example 1

Synthesis of Compound (p33) (ME-200F-200PA)

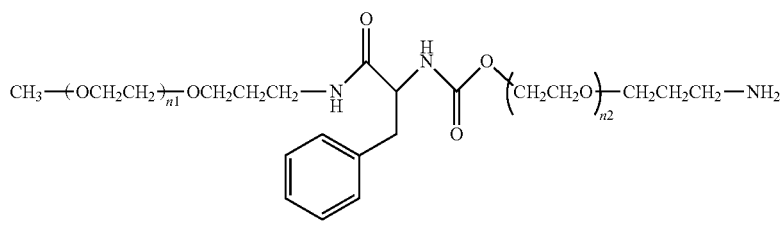
(p33)

n1 = about 480, n2 = about 450

By the same production method as in Example 4 and using L-phenylalanine with the N terminal protected by a 9-fluorenylmethyloxycarbonyl group (Fmoc group) (Fmoc-Phe) as the starting material, the above-mentioned compound (p33) (ME-200F-200PA) was obtained. yield 1.8 g. The molecular weight is shown in Table 1. HPLC: amine purity 92%.

NMR (d$_6$-DMSO): 1.62 ppm (m, 4H, —CO—NH—CH$_2$—CH$_2$—CH$_2$—O—(CH$_2$—CH$_2$—O)n-CH$_3$, —CH$_2$—CH$_2$—CH$_2$—NH$_2$), 2.80 ppm (m, 1H), 3.10 ppm (m, 2H), 3.23 ppm (s, 3H, —O—(CH$_2$—CH$_2$—O)n-CH$_3$), 3.60 ppm (m, about 3,800H, —NH—CH$_2$—CH$_2$—CH$_2$—O—(CH$_2$—CH$_2$—O)n-CH$_3$, —NH—CO—O—CH$_2$—CH$_2$—O—(CH$_2$—CH$_2$—O)n-CH$_2$—CH$_2$—), 3.95 ppm (m, 2H), 4.13 ppm (m, 1H), 7.20 ppm (m, 5H, —NH—CO—CH—CH$_2$—C$_6$H$_5$), 7.38 ppm (broad, 1H), 7.91 ppm (broad, 1H)

The average molecular weight of the polyethylene glycol derivatives obtained in Examples 1-13 and Comparative Example 1 are shown below.

TABLE 1

| sample name | | molecular weight (Mn) |
| --- | --- | --- |
| Example 1 | ME-200GLFG (SEQ ID NO: 4) (L)-2002A | 39,991 |
| Example 2 | ME-200GLFG (SEQ ID NO: 4) (L)-200AL | 41,395 |
| Example 3 | ME-100GLFG (SEQ ID NO: 4) (L)-100GLFG (SEQ ID NO: 4) (L)-100GLFG (SEQ ID NO: 4) (L)-100PA | 41,050 |
| Example 4 | ME-200G(Cit)V-200PA | 44,624 |
| Example 5 | ME-200G(Cit)V-200MA | 44,843 |
| Example 6 | ME-200GGG-200PA | 45,362 |
| Example 7 | ME-200GF-200PA | 45,055 |
| Example 8 | ME-200GAV-200PA | 41,692 |
| Example 9 | ME-200GFGG (SEQ ID NO: 5)-200PA | 41,661 |
| Example 10 | ME-200GFG-200PA | 41,640 |
| Example 11 | ME-200GF-200PA(amide) | 41,395 |
| Example 12 | ME-200GLFG (SEQ ID NO: 4) (D)-200PA | 41,084 |
| Example 13 | LY-(ME-100GLFG (SEQ ID NO: 4) (L)-100)$_2$-PA | 38,037 |
| Comparative Example 1 | ME-200F-200PA | 41,352 |

Example 14

Stability Test in Serum

Mouse or human serum (1 mL) was added to a 1.5 mL Eppendorf tube, and various polyethylene glycol derivatives were added to a concentration of 5.0 mg/mL. After incubation at 37° C. for 96 hr, 200 μL was sampled. Acetonitrile was added to thereto, and the mixture was stirred by vortex for 1 min to precipitate the protein in serum. After centrifugation, the supernatant was collected. Then, to remove hydrophobic substances such as fatty acid and the like, hexane was added to the collected liquid, and the mixture was stirred by vortex for 1 min, centrifuged, and the lower layer was collected. This solution was concentrated under vacuum conditions and the polyethylene glycol derivative was recovered from the serum. Then, GPC analysis was performed and the degradation rate of the degradable polyethylene glycol derivative was calculated.

The degradation rate was calculated by the following formula.

degradation rate=(peak area % at 40 kDa before test−peak area % at 40 kDa after test)÷(peak area % at 40 kDa before test)×100

The results are shown in the following Table 2.

TABLE 2

| | sample name | degradation rate in mouse serum | degradation rate in human serum |
| --- | --- | --- | --- |
| Example 1 | ME-200GLFG (SEQ ID NO: 4) (L)-200PA | 2% | 1% |
| Example 4 | ME-200G(cit)V-200PA | 0% | 1% |
| Example 6 | ME-200GGG-200PA | 3% | 10% |
| Example 7 | ME-200GF-200PA | 10% | 17% |
| Example 8 | ME-200GAV-200PA | 1% | 1% |
| Example 9 | ME-200GFGG (SEQ ID NO: 5)-200PA | 4% | 7% |
| Example 10 | ME-200GFG-200PA | 2% | 2% |
| Example 11 | ME-200GF-200PA(amide) | 0% | 0% |
| Example 12 | ME-200GLFG (SEQ ID NO: 4) (D)-200PA | 0% | 1% |
| Example 13 | LY-(ME-100GLFG (SEQ ID NO: 4) (L)-100)$_2$-PA | 1% | 1% |
| Comparative Example 1 | ME-200F-200PA | 0% | 0% |
| non-degradable | methoxy PEG amine 40 kDa | 0% | 0% |

According to this test, it was shown that the degradation rate of any degradable polyethylene glycol derivative was not more than 20% after 96 hr. Particularly, GLFG (SEQ ID NO: 4) (L) and G(cit)V had a low degradation rate and were stable in blood.

Example 15

Degradability Test Using Cells

Using medium RPMI-1640 (10% FBS Pn/St) (10 mL), RAW264.7 was seeded at 10×10$^6$ cells in a 100 mm dish, and cultured at 37° C. for 24 hr. The medium was exchanged with a medium in which various polyethylene glycol derivatives had been dissolved at a concentration of 10 mg/mL, and the cells were cultured at 37° C. for 96 hr. After culturing, the cells were lysed with 1% SDS solution, diluted with PBS, acetonitrile was added thereto, and the mixture was stirred for 1 min by vortex to precipitate the protein in the cell lysate, and after centrifugation, the supernatant was collected. Then, to remove hydrophobic substances such as fatty acids, hexane was added to the recovered liquid, and the mixture was stirred by vortex for 1 min, centrifuged, and the lower layer was recovered. This solution was concentrated under vacuum conditions to recover the polyethylene glycol derivative from the cells.

To confirm the degradation in the medium used for cell culture, media in which various polyethylene glycol derivatives had been dissolved at a concentration of 10 mg/mL were only cultured at 37° C. for 96 hr, and the polyethylene glycol derivative was recovered by the same operation as that described above.

Thereafter, the collected various polyethylene glycol derivatives were subjected to GPC analysis, and the degradation rate of the degradable polyethylene glycol derivative was calculated by the same calculation formula as in Example 14.

Figure 2:
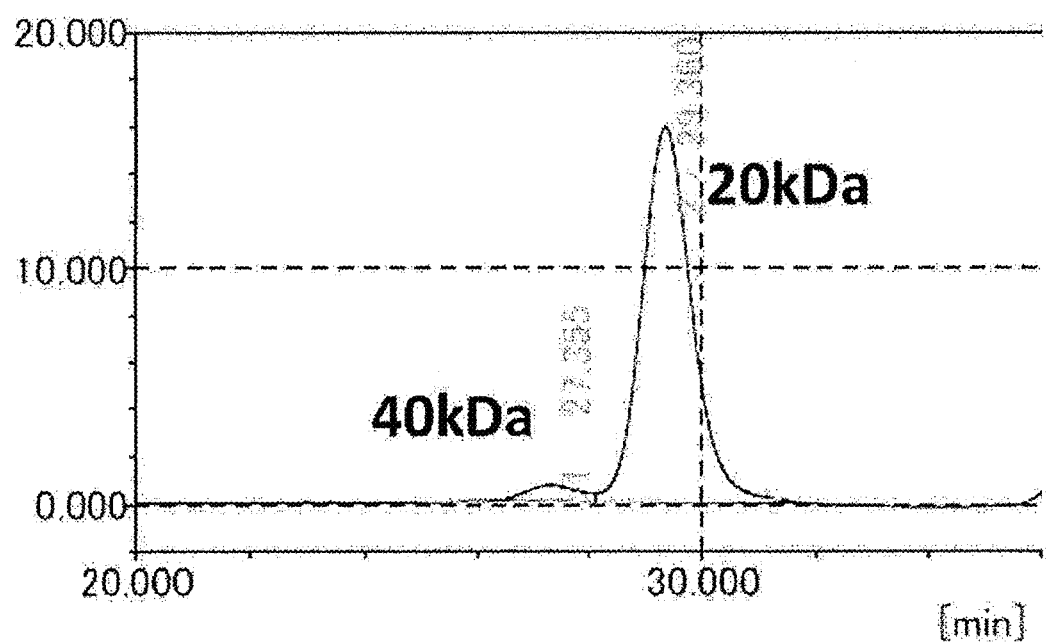
FIG. 2 shows GPC analysis results of ME-200GLFG (SEQ ID NO: 4) (L)-200PA recovered from inside of cells in the degradability test using the cells in Example 15.

The results are shown in the following Table 3. The GPC chart before and after the cell experiment is shown in FIG. 1 and FIG. 2.

TABLE 3

| sample name | | degradation rate in medium | degradation rate in cell |
|---|---|---|---|
| Example 1 | ME-200GLFG (SEQ ID NO: 4) (L)-200PA | 2% | 98% |
| Example 4 | ME-200G(cit)V-200PA | 0% | 99% |
| Example 6 | ME-200GGG-200PA | 2% | 78% |
| Example 7 | ME-200GF-200PA | 3% | 99% |
| Example 8 | ME-200GAV-200PA | 1% | 99% |
| Example 9 | ME-200GFGG (SEQ ID NO: 5)-200PA | 1% | 99% |
| Example 10 | ME-200GFG-200PA | 0% | 99% |
| Example 11 | ME-200GF-200PA(amide) | 0% | 96% |
| Example 12 | ME-200GLFG (SEQ ID NO: 4) (D)-200PA | 1% | 66% |
| Example 13 | LY-(ME-100GLFG (SEQ ID NO: 4) (L)-100)$_2$-PA | 2% | 99% |
| Comparative Example 1 | ME-200F-200PA | 0% | 0% |
| non-degradable | methoxy PEG amine 40 kDa | 0% | 0% |

It was confirmed that a polyethylene glycol derivative having an oligopeptide as a degradable linker was effectively degraded in cells and degraded into a molecular weight of 40,000 to 20,000. It was also confirmed that ME-200GLFG (SEQ ID NO: 4) (D)-200PA, which uses a D-type amino acid that does not exist in large amounts in nature, was also degraded, even though the degradation rate was low. On the other hand, degradation of the polyethylene glycol derivative of Comparative Example 1 using phenylalanine as a linker and the nondegradable methoxy PEG amine 40 kDa in cells could not be confirmed.

Example 16

PEGylation of Salmon Calcitonin (sCT)

salmon calcitonin (sCT) with the amino acid sequence: CSNLSTCVLG KLSQELHKLQ TYPRTNTGSG TP (SEQ ID NO: 1) (5 mg, $1.5 \times 10^{-6}$ mol, manufactured by PH Japan Co., Ltd.) was dissolved in 100 mM sodium acetate buffer (pH 5.0), ME-200GLFG (SEQ ID NO: 4) (L)-200AL obtained in Example 2 or methoxy PEG aldehyde 40 kDa (180 mg, $4.5 \times 10^{-6}$ mol), and a reducing agent, 2-picolylborane ($2.0 \times 10^{-5}$ mol), were added, sCT concentration was adjusted to 1.0 mg/mL, and the mixture was reacted at 4° C. for 24 hr. Thereafter, the reaction mixture was dialyzed against 10 mM sodium acetate buffer (pH 5.0), and purified by ion exchange chromatography using HiTrap SP HP (5 mL, manufactured by GE Healthcare) to give ME-200 (SEQ ID NO: 4) GLFG(L)-200-sCT or methoxy PEG 40 kDa-sCT. molar yield 44%.

RPLC Analysis
    apparatus: "ALLIANCE" manufactured by WATERS
    detector: UV (280 nm)
    column: Inertsil WP300 C18 (GL Science)
    mobile phase A: 0.05% TFA-H$_2$O
    mobile phase B: 0.05% TFA-ACN
    gradient: B30% (0 min)→B40% (5 min)→B50% (15 min)→B100% (16 min)→B100% (20 min)
    flow rate: 1.0 mL/min
    column temperature: 40° C.

Figure 3:
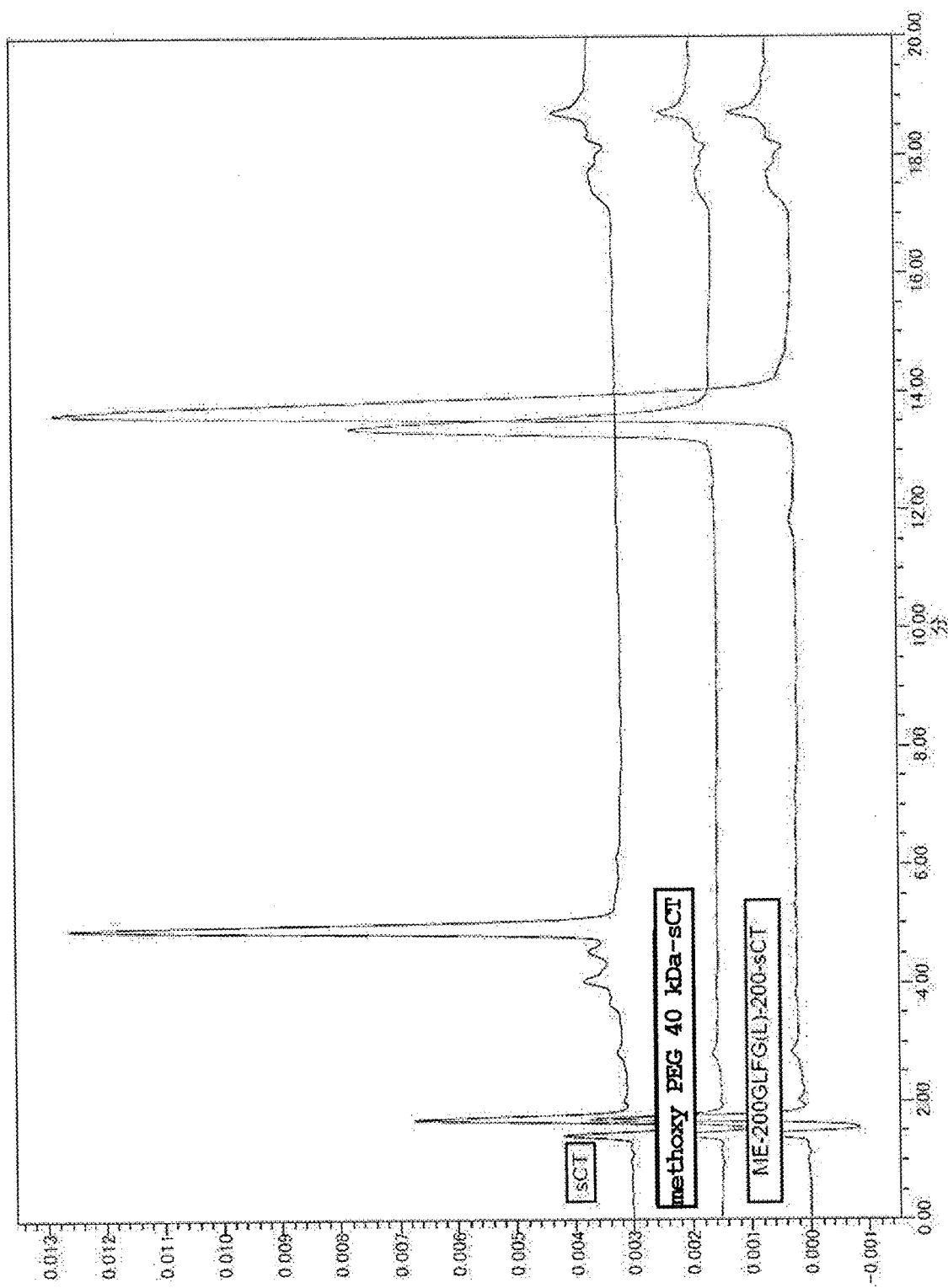
FIG. 3 shows RPLC analysis results of the conjugate of salmon calcitonin and ME-200GLFG (SEQ ID NO: 4) (L)-200AL, and the conjugate of salmon calcitonin and methoxy PEG aldehyde 40 kDa in Example 16.

The purity of PEGylated sCT was calculated under the above-mentioned RPLC analysis conditions. The results are shown in FIG. 3.
    RPLC purity of ME-200GLFG (SEQ ID NO: 4) (L)-200-sCT 99%
    RPLC purity of methoxy PEG 40 kDa-sCT 99%

MALDI-TOF-MS Analysis
    apparatus: "autoflex3" manufactured by Bruker
    sample: 0.5 mg/mL, PBS solution
    matrix: saturated α-cyano-4-hydroxycinnamic acid (CHCA) solution (0.01% TFA-H$_2$O:ACN=2:1)

The sample (1 µL) and matrix (19 µL) were mixed and 1 µL was spotted on the target.

The molecular weight of the starting material PEG and PEGylated sCT was measured under the above-mentioned MALDI-TOF-MS analysis conditions.

Figure 4:
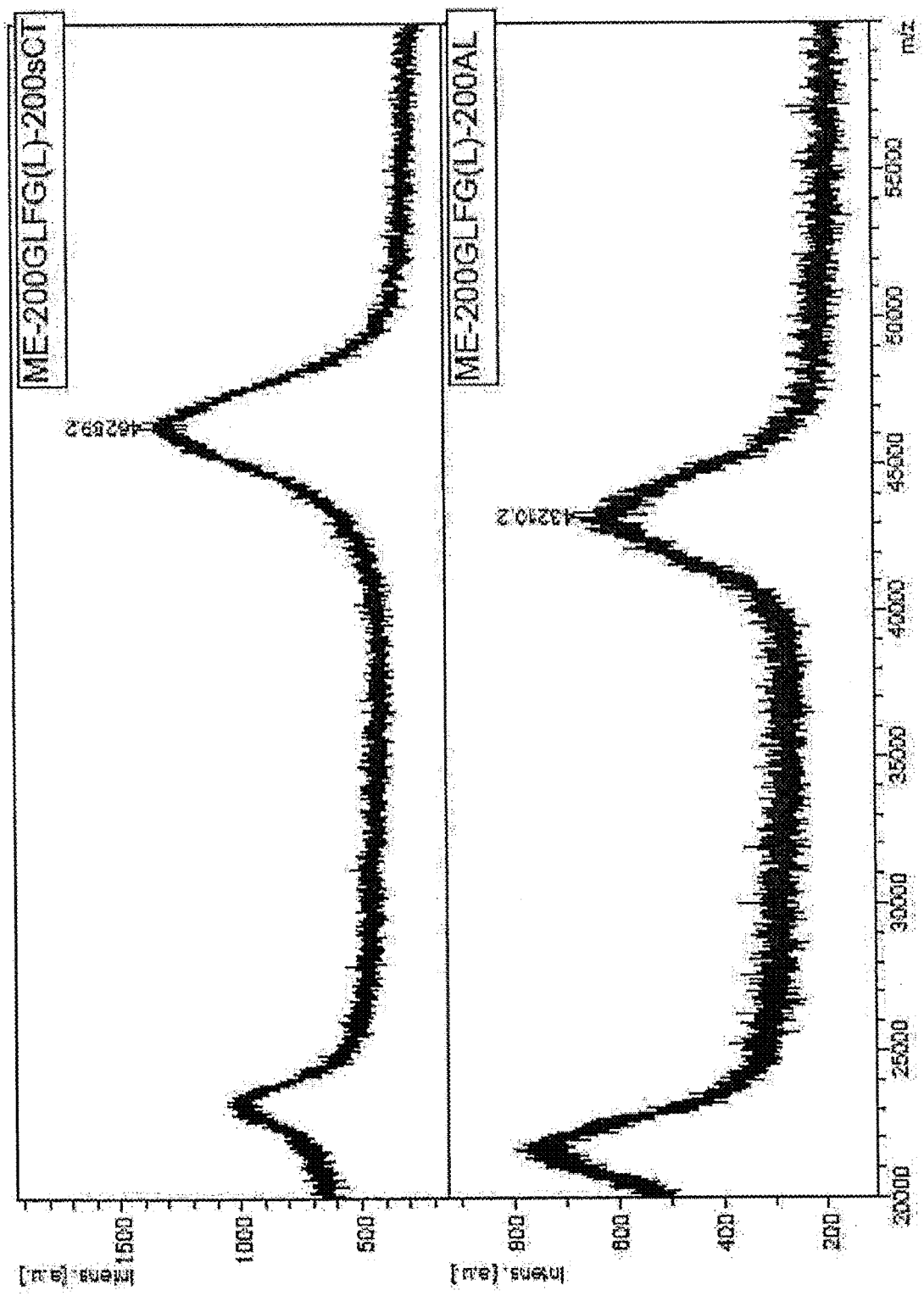
FIG. 4 shows MALDI-TOF-MS analysis results of ME-200GLFG (SEQ ID NO: 4) (L)-200AL obtained in Example 2 and ME-200GLFG (SEQ ID NO: 4) (L)-200-sCT obtained in Example 16.

FIG. 4 concurrently shows the results of MALDI-TOF-MS of the starting materials ME-200GLFG (SEQ ID NO: 4) (L)-200AL and ME-200GLFG (SEQ ID NO: 4) (L)-200-sCT.
    molecular weight of ME-200GLFG (SEQ ID NO: 4) (L)-200-sCT 46,289
    molecular weight of ME-200GLFG (SEQ ID NO: 4) (L)-200AL 43,210

Figure 5:
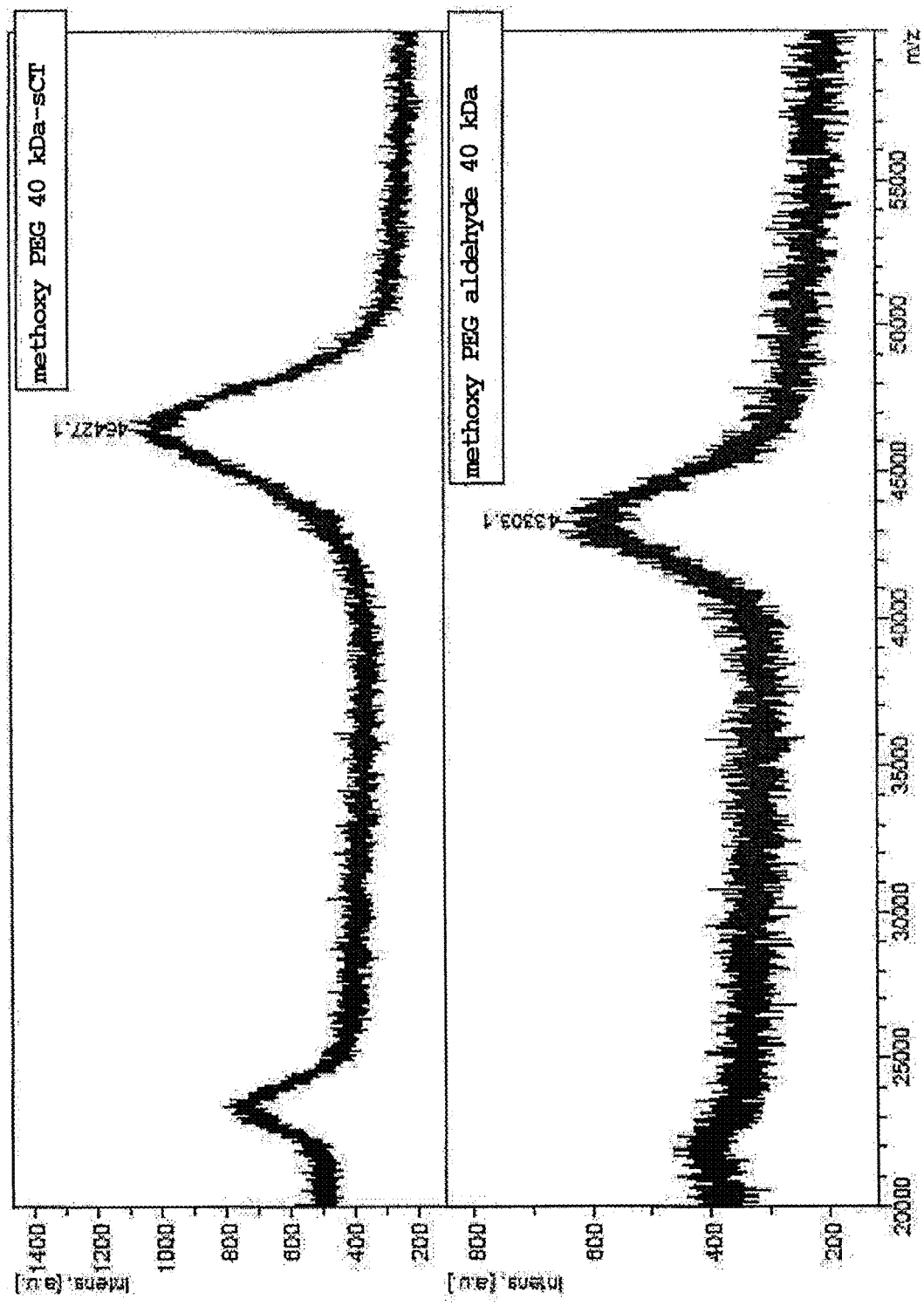
FIG. 5 shows MALDI-TOF-MS analysis results of methoxy PEG aldehyde 40 kDa and methoxy PEG 40 kDa-sCT obtained in Example 16.

FIG. 5 concurrently shows the results of MALDI-TOF-MS of the starting materials methoxy PEG aldehyde 40 kDa and methoxy PEG 40 kDa-sCT.
    molecular weight of methoxy PEG 40 kDa-sCT 46,427
    molecular weight of methoxy PEG aldehyde 40 kDa 43,303

It could be confirmed that the molecular weight of PEGylated sCT increased by about the molecular weight of sCT compared to the molecular weight of the starting material, PEG derivative.

SDS-PAGE Analysis
    kit: NuPAGE (registered trade mark) Bis-Tris Precast Gel (gel concentration 4-12%) manufactured by Thermo Fisher Scientific
    staining solution: Coomassie brilliant blue solution (CBB solution) or iodine staining solution (BaCl$_2$+I$_2$ solution)

Figure 6:
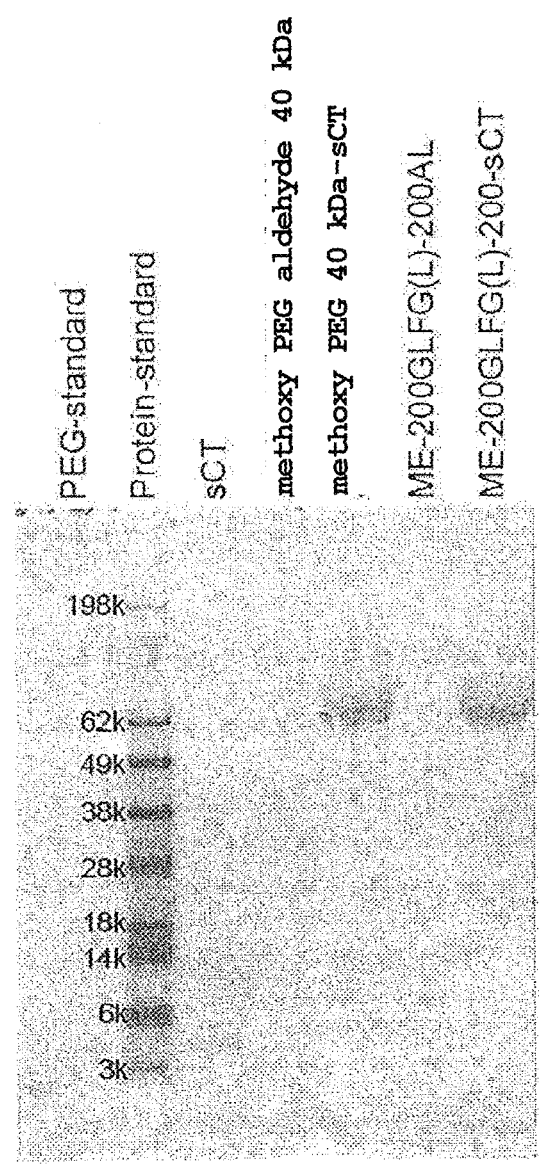
FIG. 6 shows SDS-PAGE analysis results of the conjugate of salmon calcitonin and ME-200GLFG (SEQ ID NO: 4) (L)-200AL, and the conjugate of salmon calcitonin and methoxy PEG aldehyde 40 kDa in Example 16 (left figure: CBB staining, right figure: iodine staining).
Figure 6:
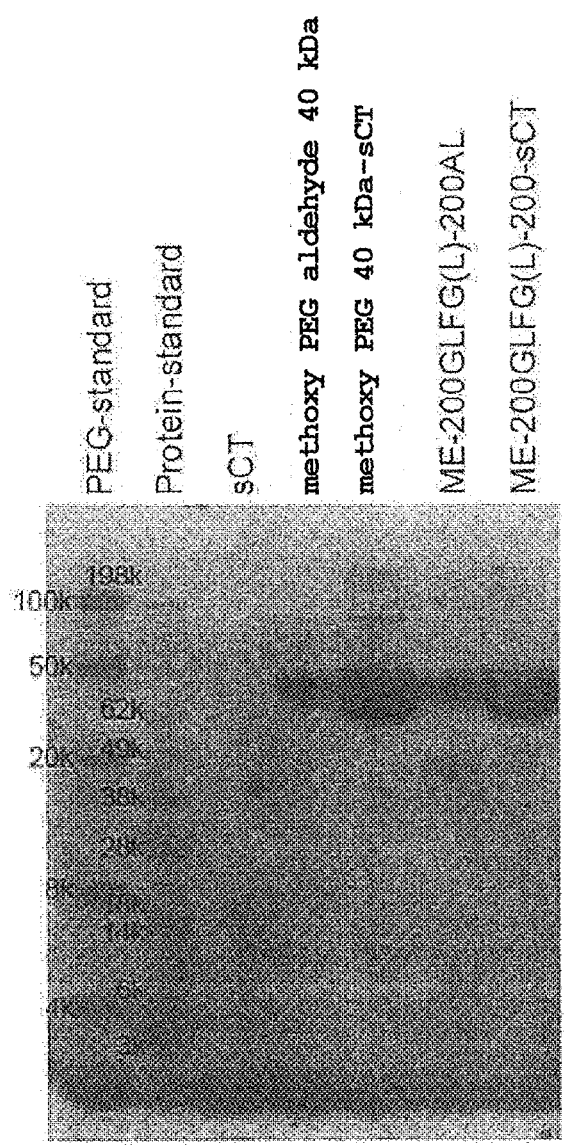

The PEGylated sCT was evaluated according to the recommended measurement conditions of the above-mentioned SDS-PAGE kit. The results are shown in FIG. 6. In PEGylated sCT, a band was observed by CBB staining that selectively stains proteins and peptides, and a band was also observed by iodine staining that stains polyethylene glycol. Bands were seen in both stains, thus confirming that the polyethylene glycol derivative was bonded to sCT.

Example 17

PEGylation of Human Growth Hormone (hGH)

Human growth hormone (hGH) with the amino acid sequence:

```
                                          (SEQ ID NO: 2)
MFPTIPLSRL FDNAMLRAHR LHQLAFDTYQ EFEEAYIPKE

QKYSFLQNPQ TSLCFSESIP TPSNREETQQ KSNLELLRIS

LLLIQSWLEP VQFLRSVFAN SLVYGASDSN VYDLLKDLEE

GIQTLMGRLE DGSPRTGQIF KQTYSKFDTN SHNDDALLKN

YGLLYCFRKD MDKVETFLRI VQCRSVEGSC GF
```

(4 mg, $1.8 \times 10^{-7}$ mol, manufactured by Shenandoah Biotechnology) was dissolved in 100 mM sodium acetate buffer (pH 5.5), ME-200GLFG (SEQ ID NO: 4) (L)-200AL obtained in Example 2 or methoxy PEG aldehyde 40 kDa (36 mg, $9.0 \times 10^{-7}$ mol), and a reducing agent, sodium cyanoborohydride ($9.0 \times 10^{-6}$ mol) were added, hGH concentration was adjusted to 1.0 mg/mL, and the mixture was reacted at 25° C. for 24 hr. Thereafter, the reaction mixture was dialyzed against 10 mM sodium acetate buffer (pH 4.7), and purified by ion exchange chromatography using HiTrap SP HP (5 mL, manufactured by GE Healthcare) to give ME-200GLFG (SEQ ID NO: 4) (L)-200-hGH or methoxy PEG 40 kDa-hGH. molar yield 30%.

RPLC Analysis
  apparatus: "ALLIANCE" manufactured by WATERS
  detector: UV (280 nm)
  column: Inertsil WP300 C18 (GL Science)
  mobile phase A: 0.05% TFA-$H_2O$
  mobile phase B: 0.05% TFA-ACN
  gradient: B40% (0 min)→B80% (25 min)→B90% (27 min)→B40% (27.1 min)
  flow rate: 1.0 mL/min
  column temperature: 40° C.

The purity of PEGylated hGH was calculated under the above-mentioned RPLC analysis conditions.
  RPLC purity of ME-200GLFG (SEQ ID NO: 4) (L)-200-hGH 90%
  RPLC purity of methoxy PEG 40 kDa-hGH 97%

MALDI-TOF-MS Analysis
  apparatus: "autoflex3" manufactured by Bruker
  sample: 0.5 mg/mL, PBS solution
  matrix: saturated cinnamic acid (SA) solution (0.01% TFA-$H_2O$:ACN=2:1)
  The sample (1 μL) and matrix (19 μL) were mixed and 1 μL was spotted on the target.

Figure 7:
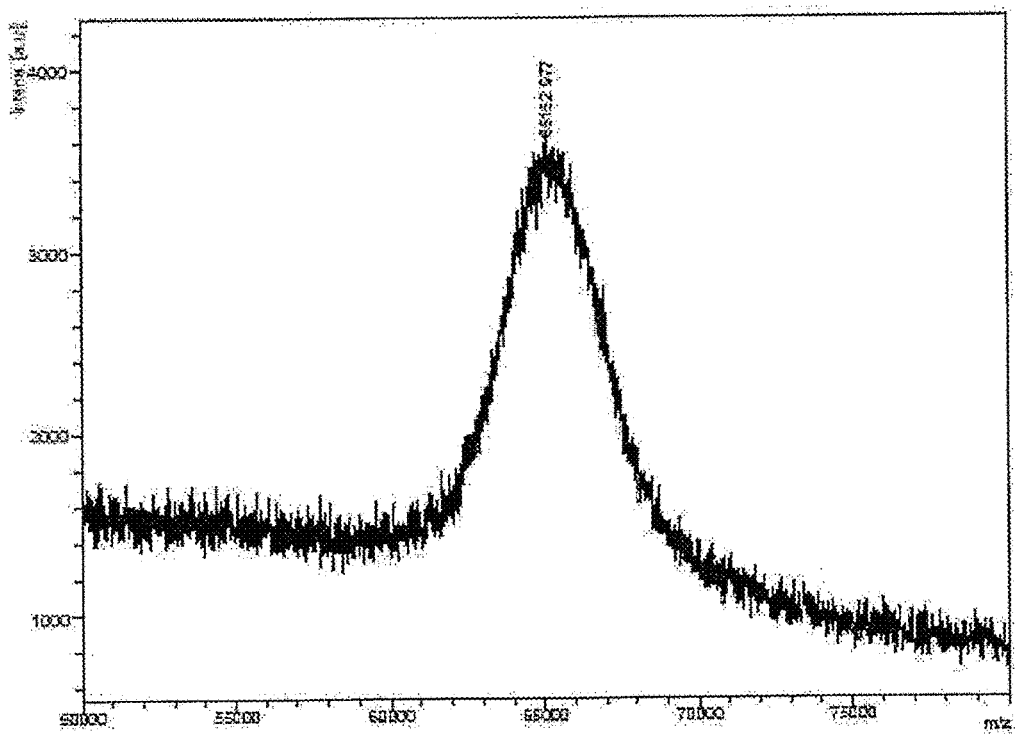
FIG. 7 shows MALDI-TOF-MS analysis results of the conjugate of human growth hormone and ME-200GLFG (SEQ ID NO: 4) (L)-200AL in Example 17.
Figure 8:
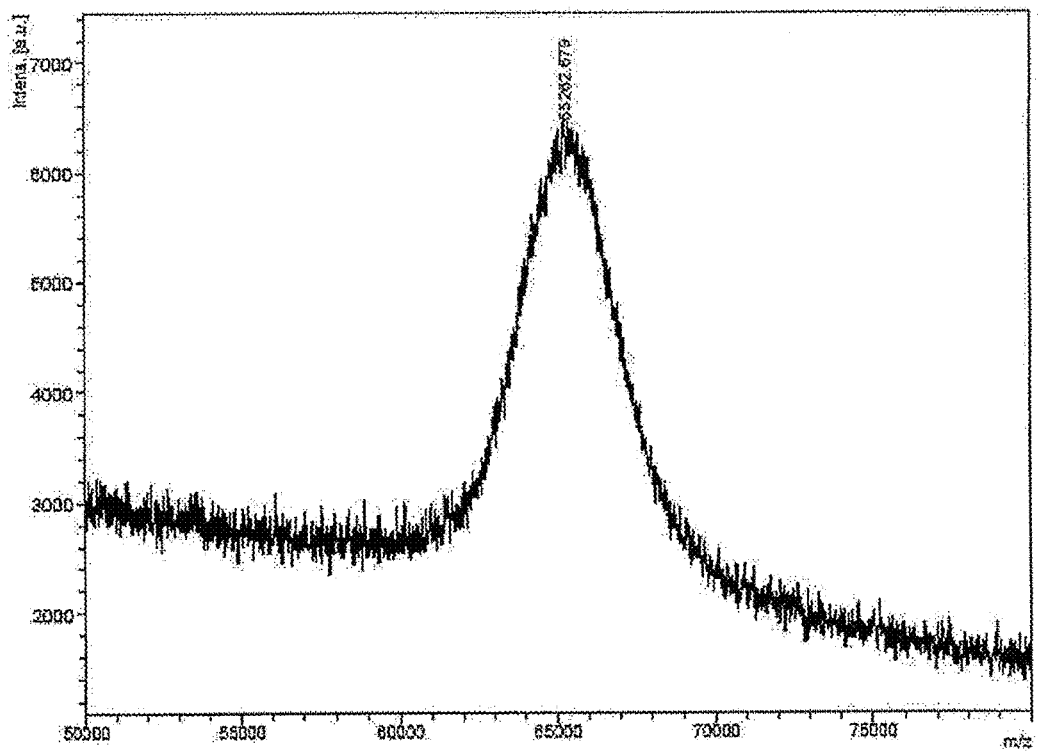
FIG. 8 shows MALDI-TOF-MS analysis results of the conjugate of human growth hormone and methoxy PEG aldehyde 40 kDa in Example 17.

The molecular weight of PEGylated hGH was measured under the above-mentioned MALDI-TOF-MS analysis conditions. The results are shown in FIG. 7 and FIG. 8.
  molecular weight of ME-200GLFG (SEQ ID NO: 4) (L)-200-hGH 65,153
  molecular weight of methoxy PEG 40 kDa-hGH 65,263

It was confirmed that the molecular weight of PEGylated hGH increased by about the molecular weight of hGH compared to the molecular weight of the starting material, PEG derivative (see FIG. 4 and FIG. 5).

SDS-PAGE Analysis
  kit: NuPAGE (registered trade mark) Bis-Tris Precast Gel (gel concentration 4-12%) manufactured by Thermo Fisher Scientific
  staining solution: Coomassie brilliant blue solution (CBB solution) or iodine staining solution ($BaCl_2+I_2$ solution)

Figure 9:
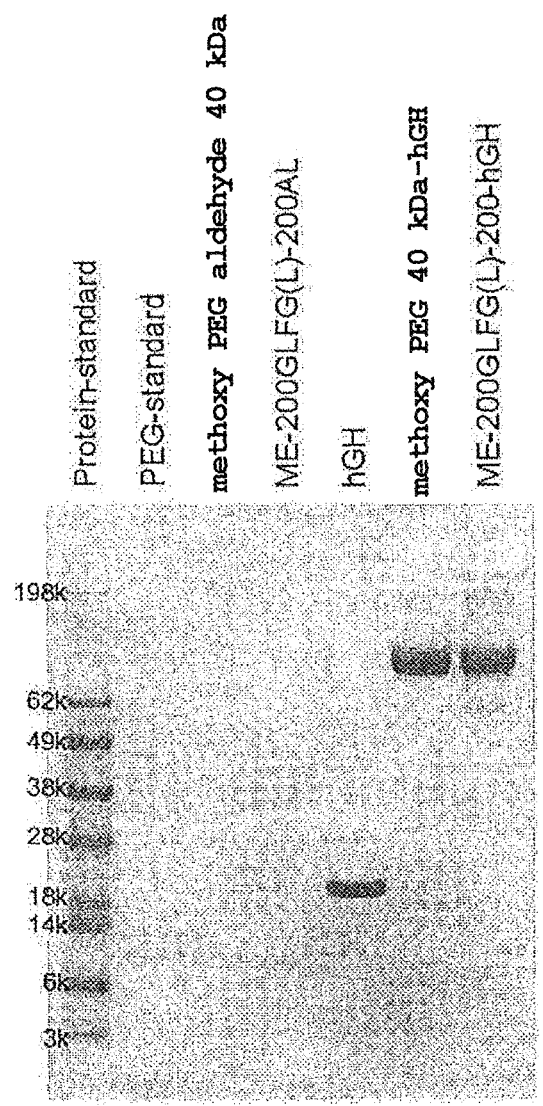
FIG. 9 shows SDS-PAGE analysis results of the conjugate of human growth hormone and ME-200GLFG (SEQ ID NO: 4) (L)-200AL, and the conjugate of human growth hormone and methoxy PEG aldehyde 40 kDa in Example 17 (left figure: CBB staining, right figure: iodine staining).
Figure 9:
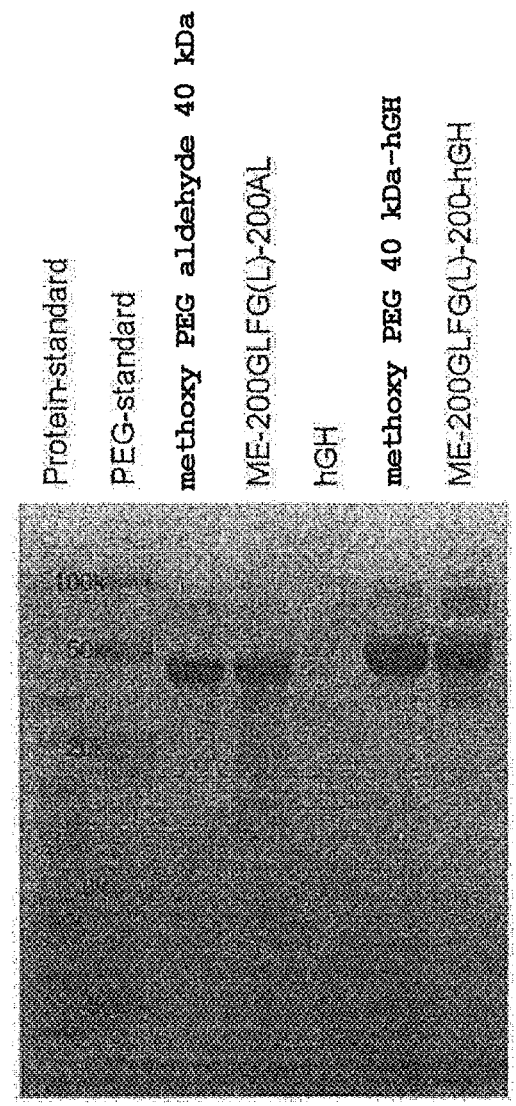

The PEGylated hGH was evaluated according to the recommended measurement conditions of the above-mentioned SDS-PAGE kit. The results are shown in FIG. 9. In PEGylated hGH, a band was observed by CBB staining that selectively stains proteins and peptides, and a band was also observed by iodine staining that stains polyethylene glycol. Bands were seen in both stains, thus confirming that the polyethylene glycol derivative was bonded to hGH.

Example 18

PEGylation of Granulocyte Colony Stimulating Factor (GCSF)

A granulocyte colony stimulating factor (GCSF) with the amino acid sequence: TPLGPASSLP QSFLLKCLEQ VRKIQGDGAA LQEKLCATYK LCHPEELVLL GHSLGIPWAP LSSCPSQALQ LAGCLSQLHS GLFLYQGLLQ ALEGISPELG PTLDTLQLDV ADFATTIWQQ MEELGMAPAL QPTQGAMPAF ASAFQRRAGG VLVASHLQSF LEVSYRVLRH LAQP (SEQ ID NO: 3) (100 μg, $5.3\times10^{-9}$ mol, manufactured by PeproTech) was dissolved in 10 mM sodium acetate buffer (pH 4.6, containing 5% sorbitol), ME-200GLFG (SEQ ID NO: 4) (L)-200AL obtained in Example 2 and a reducing agent, sodium cyanoborohydride ($5.3\times10^{-7}$ mol) were added, GCSF concentration was adjusted to 2.0 mg/mL, and the mixture was reacted at 4° C. for 24 hr. Thereafter, the reaction mixture was diluted with 10 mM sodium acetate buffer (pH 4.6), and purified by ion exchange chromatography using HiTrap SP HP (5 mL, manufactured by GE Healthcare) to give ME-200GLFG (SEQ ID NO: 4) (L)-200-GCSF. molar yield 64%.

RPLC Analysis
  apparatus: "ALLIANCE" manufactured by WATERS
  detector: UV (280 nm)
  column: Inertsil WP300 C18 (GL Science)
  mobile phase A: 0.1% TFA-$H_2O$
  mobile phase B: 0.1% TFA-ACN
  gradient: B40% (0 min)→B70% (25 min)→B90% (27 min)→B40% (29 min)
  flow rate: 1.0 mL/min
  column temperature: 40° C.

The purity of PEGylated GCSF was calculated under the above-mentioned RPLC analysis conditions.
  RPLC purity of ME-200GLFG (SEQ ID NO: 4) (L)-200-GCSF 97%

MALDI-TOF-MS Analysis
  apparatus: "autoflex3" manufactured by Bruker
  sample: 0.5 mg/mL, PBS solution
  matrix: saturated cinnamic acid (SA) solution (0.01% TFA-$H_2O$:ACN=2:1)
  The sample (1 μL) and matrix (19 μL) were mixed and 1 μL was spotted on the target.

The molecular weight of PEGylated GCSF was measured under the above-mentioned MALDI-TOF-MS analysis conditions. molecular weight of ME-200GLFG (SEQ ID NO: 4) (L)-200-GCSF 62,266 It could be confirmed that the molecular weight of PEGylated GCSF increased by about the molecular weight of GCSF compared to the molecular weight of the starting material, PEG derivative.

S-PAGE Analysis
  kit: NuPAGE (registered trade mark) Bis-Tris Precast Gel (gel concentration 4-12%) manufactured by Thermo Fisher Scientific
  staining solution: Coomassie brilliant blue solution (CBB solution) or iodine staining solution ($BaCl_2+I_2$ solution)

The PEGylated GCSF was evaluated according to the recommended measurement conditions of the above-mentioned SDS-PAGE kit. In PEGylated GCSF, a band was observed by CBB staining that selectively stains proteins and peptides, and a band was also observed by iodine staining that stains polyethylene glycol. Bands were seen in both stains, thus confirming that the polyethylene glycol derivative was bonded to GCSF.

Example 19

Evaluation of Physiological Activity of PEGylated Salmon Calcitonin (sCT)

Figure 10:
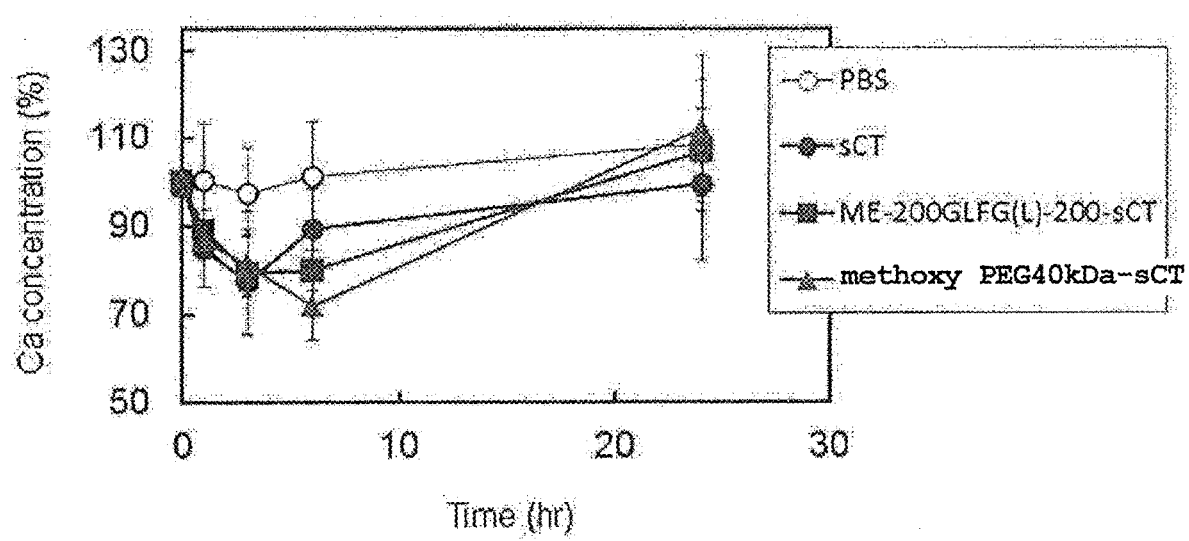
FIG. 10 shows evaluation results of the physiological activity (blood calcium concentration) of salmon calcitonin and PEGylated salmon calcitonin in Example 19.

The physiological activities of 4 groups of ME-200GLFG (SEQ ID NO: 4) (L)-200-sCT which is SCT to which degradable polyethylene glycol derivative with a molecular weight of 40,000 is bonded and obtained in Example 16, methoxy PEG 40 kDa-sCT bonded to nondegradable methoxy PEG 40 kDa, unmodified sCT, and saline were comparatively evaluated in animal experiments. Mouse strain was Balb/c (8-week-old, male), sCT solution and PEGylated sCT solution were each prepared to achieve sCT concentration of 0.5 mg/mL with saline, and administered at a sCT dose of 40 μg/kg. A trace amount of blood was collected from the mice at 1, 3, 6, 24 hr, and calcium concentration was measured using calcium E-Test Wako (manufactured by Wako Pure Chemical Industries, Ltd.). The results thereof are shown in FIG. 10.

All sCTs significantly reduced calcium concentration as compared to the saline (PBS) group. Unmodified sCT showed an increase in calcium concentration 6 hr after administration. It was found that a low calcium concentration was continuously maintained in ME-200GLFG (SEQ ID NO: 4) (L)-200-sCT and methoxy PEG 40 kDa-sCT. It was shown that PEGylation prolonged the half-life in blood of sCT and extended the physiological activity.

Example 20

Pharmacokinetics Test (Radioisotope) by Animal Experiment

ME-200GLFG (SEQ ID NO: 4) (L)-200-sCT which is sCT bonded to a degradable polyethylene glycol derivative with a molecular weight of 40,000, and was obtained in Example 16 and methoxy PEG 40 kDa-sCT bonded to nondegradable methoxy PEG 40 kDa were each dissolved in 50 mM aqueous sodium hydrogen carbonate solution to a concentration of 0.1 mg/mL, Bolton-Hunter reagents (0.4625 MBq) were added thereto, and the mixture were stirred by vortex and reacted at room temperature overnight. The reaction solution was fractionated with a PD-10 column.

Using a polyethylene glycol color reagent (ammonium thiocyanate and cobalt nitrate) and a gamma counter, the fraction containing $^{125}I$ was confirmed and collected.

Using the obtained radioisotope-labeled two kinds of PEGylated sCTs, and sCT labeled similarly, the pharmacokinetics were evaluated in animal experiment. Mouse strain was Balb/c (8-week-old, male) and, as a PEGylated sCT solution, an unlabeled PEGylated sCT was prepared at a concentration of 50 mg/mL using physiological saline, radioisotope-labeled PEGylated sCT was added in a trace amount, and the mixture (20 μL) was administered from the mouse tail vein. Thereafter, blood and each organ (liver, kidney, spleen, lung, brain, heart, stomach, pancreas, intestine, testicle, thyroid gland and the like) were taken out from the mouse at 1, 3, 6, and 48 hr, and the retention amount of the labeled PEGylated sCT was measured using a gamma counter.

Figure 11:
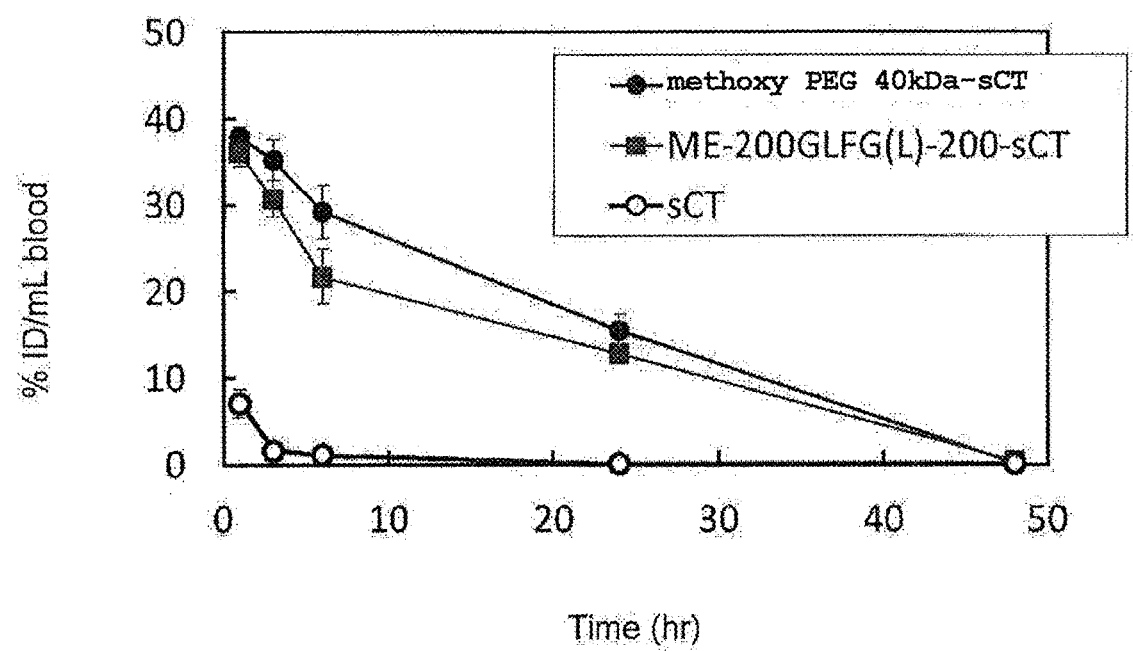
FIG. 11 shows evaluation results of pharmacokinetics (blood concentration) of radioisotope-labeled salmon calcitonin, radioisotope-labeled ME-200GLFG (SEQ ID NO: 4) (L)-200-sCT, and radioisotope-labeled methoxy PEG 40 kDa-sCT in Example 20.
Figure 12:
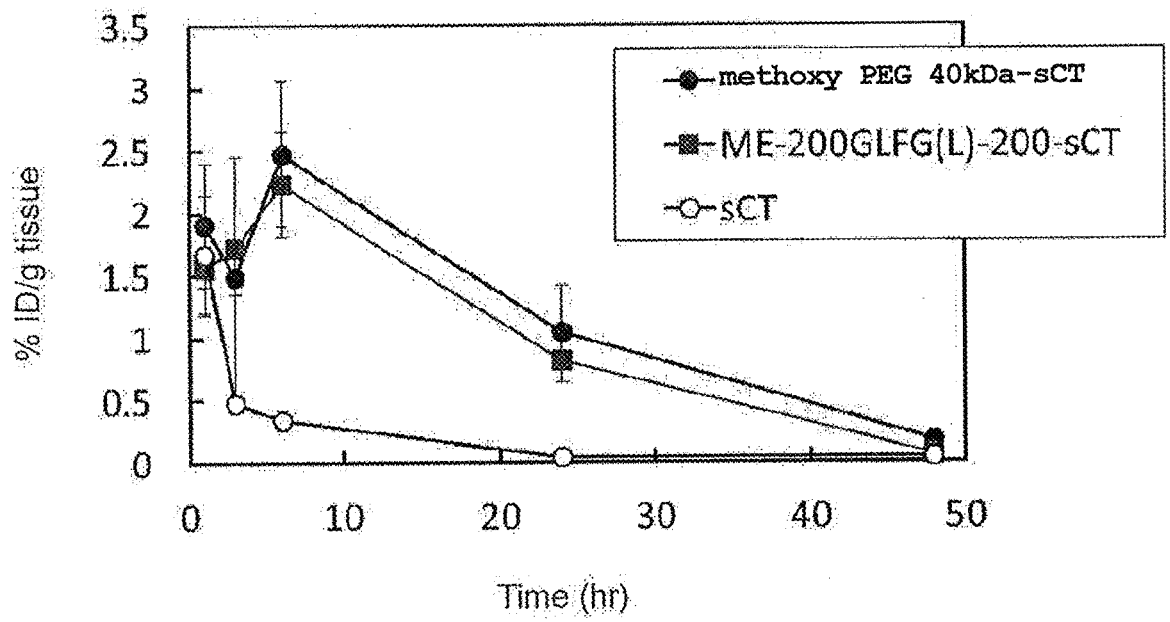
FIG. 12 shows amounts of retention of radioisotope-labeled salmon calcitonin, radioisotope-labeled ME-200GLFG (SEQ ID NO: 4) (L)-200-sCT, and radioisotope-labeled methoxy PEG 40 kDa-sCT in the liver in Example 20.
Figure 13:
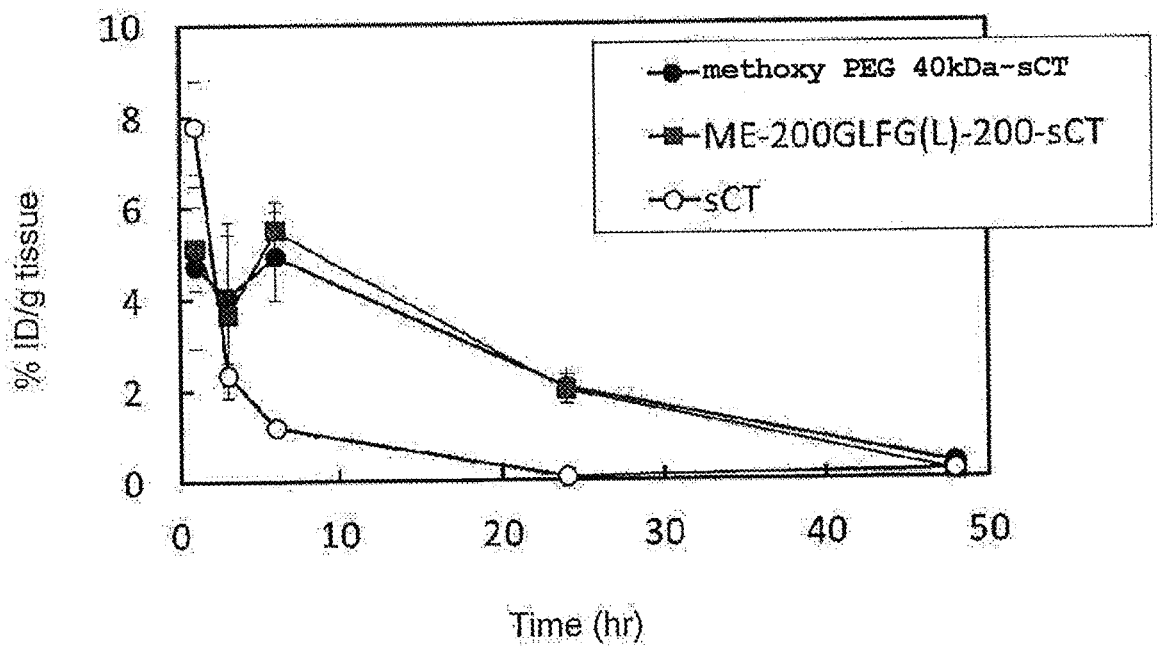
FIG. 13 shows amounts of retention of radioisotope-labeled salmon calcitonin, radioisotope-labeled ME-200GLFG (SEQ ID NO: 4) (L)-200-sCT, and radioisotope-labeled methoxy PEG 40 kDa-sCT in the kidney in Example 20.
Figure 14:
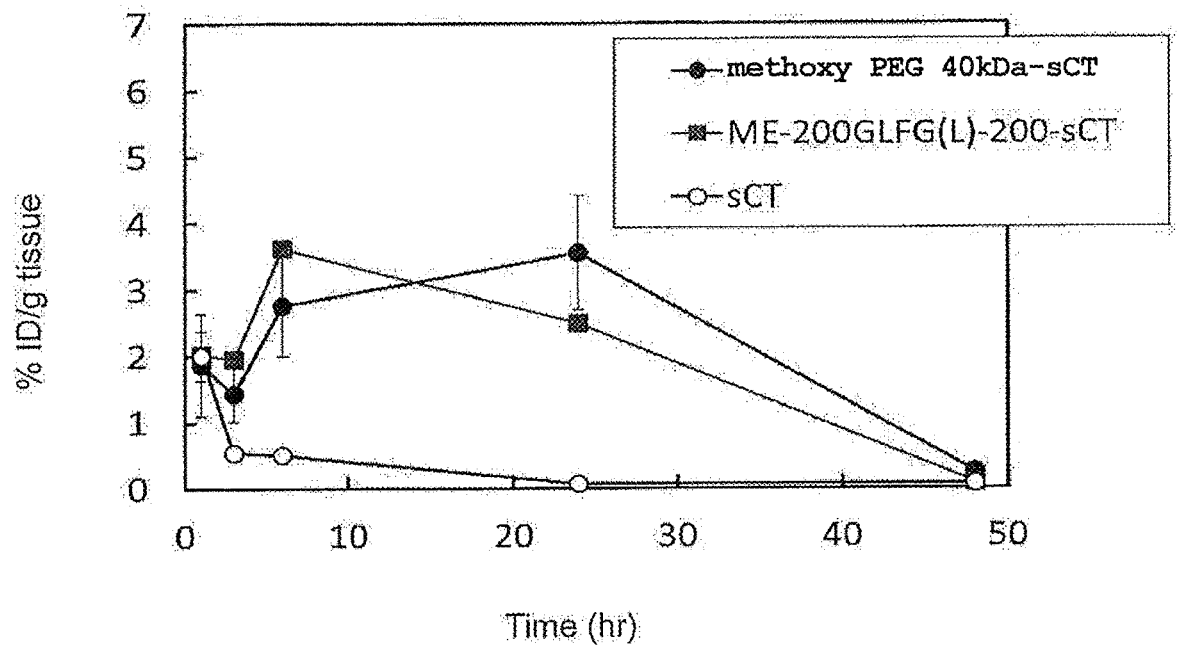
FIG. 14 shows amounts of retention of radioisotope-labeled salmon calcitonin, radioisotope-labeled ME-200GLFG (SEQ ID NO: 4) (L)-200-sCT, and radioisotope-labeled methoxy PEG 40 kDa-sCT in the spleen in Example 20.
Figure 15:
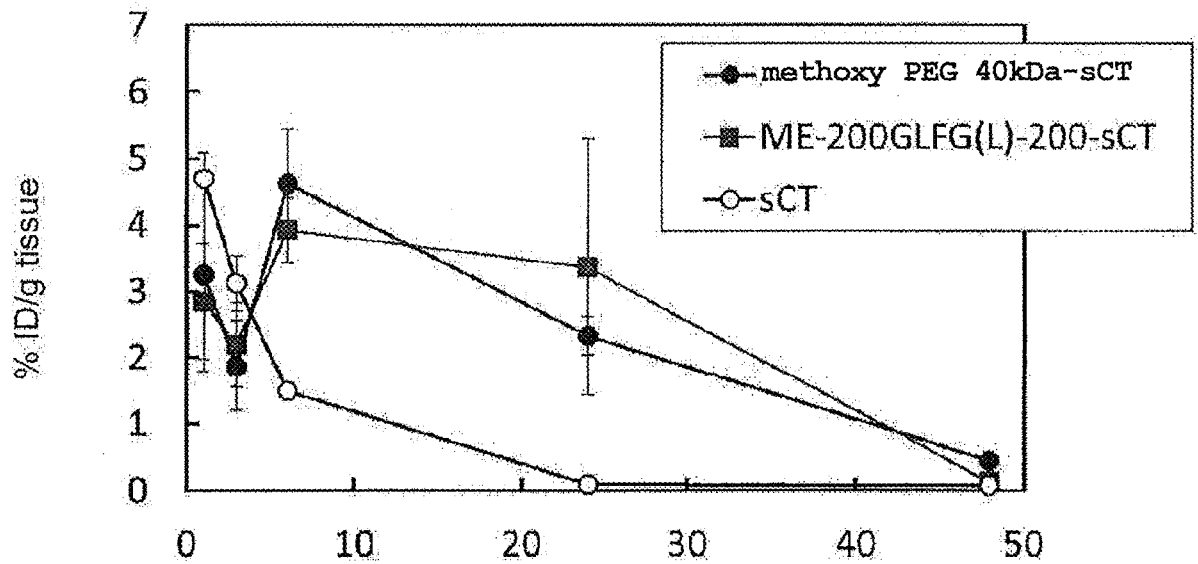
FIG. 15 shows amounts of retention of radioisotope-labeled salmon calcitonin, radioisotope-labeled ME-200GLFG (SEQ ID NO: 4) (L)-200-sCT, and radioisotope-labeled methoxy PEG 40 kDa-sCT in the lung in Example 20.

As the results of the pharmacokinetics test of radioisotope-labeled ME-200GLFG (SEQ ID NO: 4) (L)-200-sCT which is sCT bonded to a degradable polyethylene glycol derivative, and radioisotope-labeled methoxy PEG 40 kDa-sCT which is sCT bonded to a nondegradable methoxy PEG 40 kDa, FIG. 11 shows blood concentration, and FIGS. 12-15 show retention amounts in liver, kidney, spleen, and lung as representative organs.

From the results, it could be demonstrated that ME-200GLFG (SEQ ID NO: 4) (L)-200-sCT has a similar level of blood half-life and the same distribution tendency in the body compared with general methoxy PEG 40 kDa-sCT without degradability.

Example 21

Figure 16:
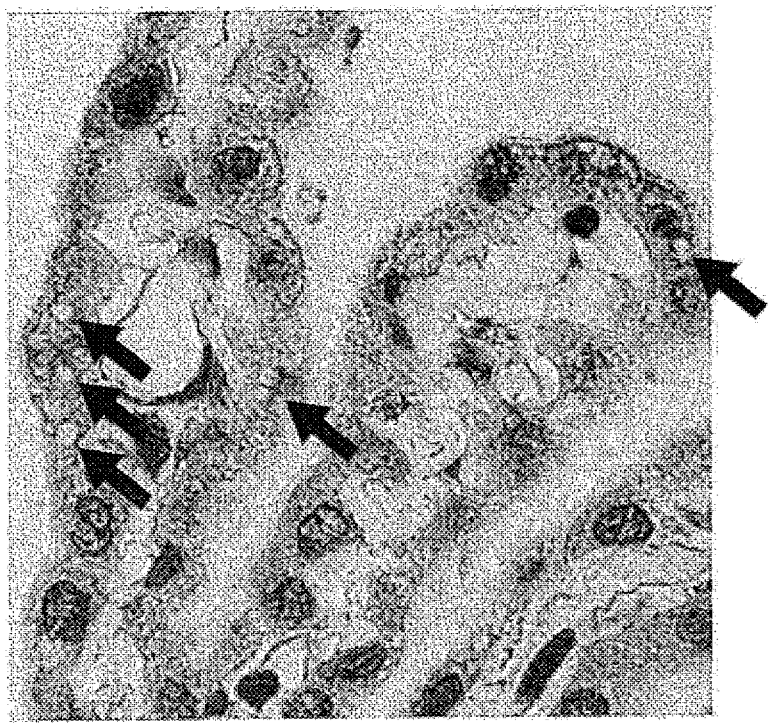
FIG. 16 shows an image of a section of cerebral choroid plexus of a mouse that received long-term administration of methoxy PEG amine 40 kDa in Example 21 (arrows show vacuoles).
Figure 17:
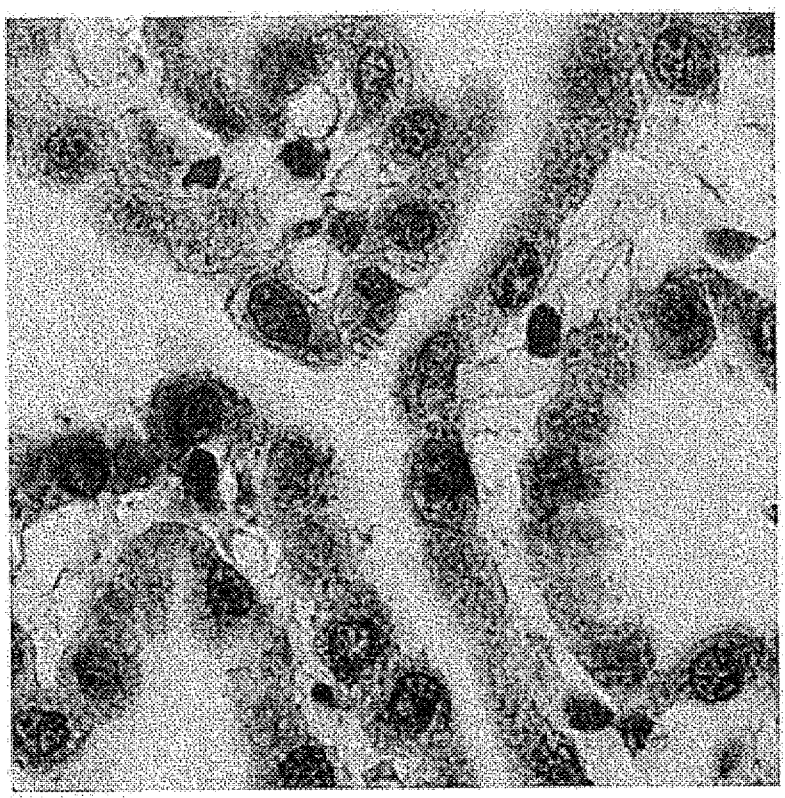
FIG. 17 shows an image of a section of cerebral choroid plexus of a mouse that received long-term administration of ME-200GLFG (SEQ ID NO: 4) (L)-200PA in Example 21.

Vacuole formation evaluation test by animal experiment Using ME-200GLFG (SEQ ID NO: 4) (L)-200PA which is a degradable polyethylene glycol derivative with a molecular weight of 40,000 and having an amino group at the terminal, which was obtained in Example 1, and nondegradable methoxy PEG amine 40 kDa, vacuole formation was evaluated by an animal experiment. Mouse strain was Balb/c (8-week-old, male) and, as a polyethylene glycol solution, a polyethylene glycol derivative was prepared at a concentration of 100 mg/mL using physiological saline, and 20 μL was administered from the mouse tail vein. The administration was continued 3 times a week continuously for 4 weeks. After the completion of administration, the mice were perfused and fixed with a 4% aqueous paraformaldehyde solution to prepare paraffin sections. HE staining and immunostaining with anti-PEG antibody were performed to evaluate vacuole formation in choroid plexus epithelial cells of the brain. Immunostaining was performed using an immunostaining kit (BOND Refine Polymer Detection Kit, manufactured by Leica) and an anti-PEG antibody (B-47 antibody, manufactured by Abcam). Images of choroid plexus sections of the brain immunostained with anti-PEG antibody are shown in FIG. 16 and FIG. 17.

As a result, ME-200GLFG (SEQ ID NO: 4) (L)-200PA which is a degradable polyethylene glycol significantly suppressed vacuole formation as compared with methoxy PEG amine 40 kDa.

The amount of polyethylene glycol administered in this Example is an amount optimized to evaluate vacuolation, and extremely large compared with the dose of polyethylene glycol that is generally used in the art.

Example 22

Accumulation Evaluation Test of Polyethylene Glycol by Animal Experiment

Figure 18:
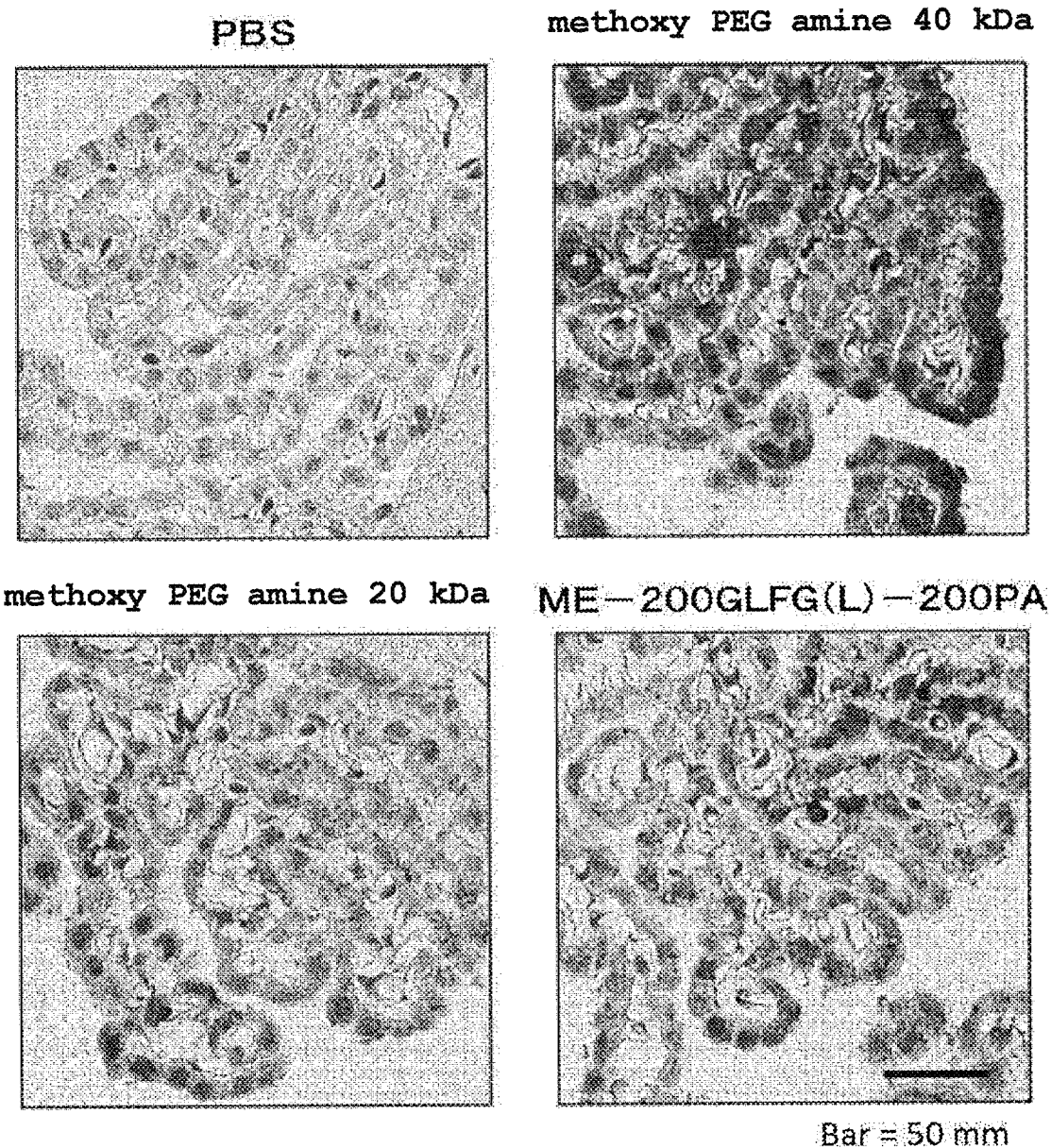
FIG. 18 shows images of sections of cerebral choroid plexus of mice that received long-term administration of PBS, methoxy PEG amine 40 kDa, methoxy PEG amine 20 kDa, and ME-200GLFG (SEQ ID NO: 4) (L)-200PA in Example 22 (part stained in brown shows accumulation of PEG).

Using ME-200GLFG (SEQ ID NO: 4) (L)-200PA which is a degradable polyethylene glycol derivative with a molecular weight of 40,000 and having an amino group at the terminal, and nondegradable methoxy PEG amine 20 kDa, nondegradable methoxy PEG amine 40 kDa, and PBS as a control, accumulation of polyethylene glycol was evaluated by an animal experiment. Mouse strain was Balb/c (8-week-old, male) and, as a polyethylene glycol solution, a polyethylene glycol derivative was prepared at a concentration of 62.5 mg/mL using physiological saline, and 100 μL was administered from the mouse tail vein. The administration was continued 3 times a week continuously for 4 weeks. After the completion of administration, the mice were perfused and fixed with a 4% aqueous paraformaldehyde solution to prepare paraffin sections. Immunostaining with anti-PEG antibody was performed to evaluate accumulation in choroid plexus epithelial cells of the brain. Images of each immunostained choroid plexus section of the brain are shown in FIG. 18.

The results show no staining in choroid plexus section of mice administered with PBS without containing polyethylene glycol, whereas brown staining over a wide area of the section with non-degradable methoxy PEG amine 40 kDa. The stained portion shows accumulation of PEG. On the other hand, in the section of ME-200GLFG (SEQ ID NO: 4) (L)-200PA which is degradable polyethylene glycol a brown-stained portion is small, and accumulation was equivalent to that of methoxy PEG amine 20 kDa with a half molecular weight. Due to the degradability, degradable polyethylene glycol significantly suppressed the accumulation of polyethylene glycol in tissues as compared with nondegradable methoxy PEG amine 40 kDa having the same molecular weight.

To quantify the accumulation, image analysis was performed using the following analysis software, and the score was calculated.

apparatus: All in one microscopy BZ-X710
analysis soft: BZ-X Analyzer

Specifically, the area of the choroid plexus tissue in the image, and the area of the brown stained portion showing the accumulation were extracted with analysis software, and scoring was performed using the following calculation formula. The calculated scores are shown in Table 4.

accumulation rate=area of brown stained portion/area of choroid plexus tissue score=accumulation rate/accumulation rate of PBS As a result, it was shown that degradable polyethylene glycol can significantly suppress the accumulation of polyethylene glycol in tissues.

The amount of polyethylene glycol administered in this Example is an amount optimized to evaluate accumulation, and extremely large compared with the dose of polyethylene glycol that is generally used in the art.

TABLE 4

|  | score |
|---|---|
| PBS | 1.0 |
| methoxy PEG amine 40 kDa | 35.9 |

TABLE 4-continued

|  | score |
|---|---|
| methoxy PEG amine 20 kDa | 2.3 |
| ME-200GLFG (SEQ ID NO: 4) (L)-200PA | 4.2 |

INDUSTRIAL APPLICABILITY

In the bio-related substance bonded to a degradable polyethylene glycol derivative of the present invention, the degradable polyethylene glycol derivative is stable in blood in the body because it has an oligopeptide between the polyethylene glycol chains which is degraded by intracellular enzymes and can impart, to the bio-related substance, a half-life in blood that is equivalent to that of conventional polyethylene glycol derivatives without degradability. Thus, when the degradable polyethylene glycol derivative is incorporated into cells, the oligopeptide moiety between the polyethylene glycol chains is rapidly degraded, thus suppressing the generation of vacuoles in cells which has been a problem to date.

This application is based on patent application No. 2018-064306 filed in Japan, the contents of which are encompassed in full herein.

The invention claimed is:

1. A bio-related substance bonded to a degradable polyethylene glycol derivative, and represented by formula (A):

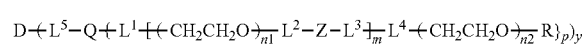

formula (A)

wherein D is the bio-related substance, and wherein

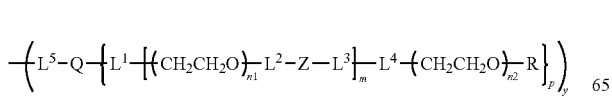

is ME-200GLFG(L)-200PA, ME-200GGG-200PA, ME-200GF-200PA, ME-200GAV-200PA, ME-200GFGG-200PA, or LY-(ME-100GLFG(L)-100)$_2$-PA.

2. The bio-related substance according to claim 1, wherein the bio-related substance for D is a hormone, a cytokine, an antibody, an aptamer or an enzyme.

3. The bio-related substance according to claim 1, wherein

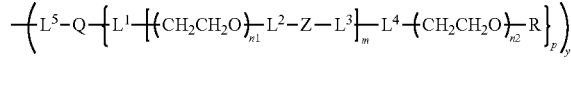

of the formula (A) is ME-200GLFG(L)-200PA.

4. The bio-related substance according to claim 3, wherein the bio-related substance for D is a hormone, a cytokine, an antibody, an aptamer or an enzyme.

5. The bio-related substance according to claim 1, wherein

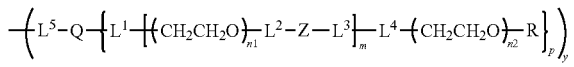

of the formula (A) is ME-200GGG-200PA.

6. The bio-related substance according to claim 5, wherein the bio-related substance for D is a hormone, a cytokine, an antibody, an aptamer or an enzyme.

7. The bio-related substance according to claim 1, wherein

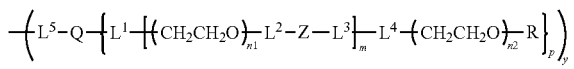

of the formula (A) is ME-200GF-200PA.

8. The bio-related substance according to claim 7, wherein the bio-related substance for D is a hormone, a cytokine, an antibody, an aptamer or an enzyme.

9. The bio-related substance according to claim 1, wherein

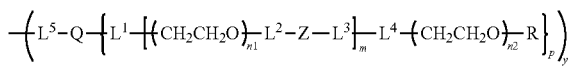

of the formula (A) is ME-200GAV-200PA.

10. The bio-related substance according to claim 9, wherein the bio-related substance for D is a hormone, a cytokine, an antibody, an aptamer or an enzyme.

11. The bio-related substance according to claim 1, wherein

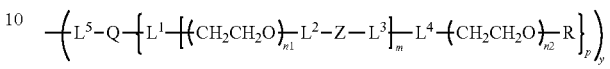

of the formula (A) is ME-200GFGG-200PA.

12. The bio-related substance according to claim 11, wherein the bio-related substance for D is a hormone, a cytokine, an antibody, an aptamer or an enzyme.

13. The bio-related substance according to claim 1, wherein

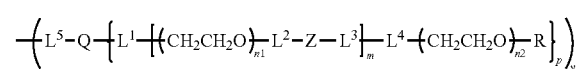

of the formula (A) is LY-(ME-100GLFG(L)-100)$_2$-PA.

14. The bio-related substance according to claim 13, wherein the bio-related substance for D is a hormone, a cytokine, an antibody, an aptamer or an enzyme.

* * * * *

SEQUENCE LISTING

```
<160> NUMBER OF SEQ ID NOS: 3

<210> SEQ ID NO 1
<211> LENGTH: 32
<212> TYPE: PRT
<213> ORGANISM: Salmo salar

<400> SEQUENCE: 1

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30

<210> SEQ ID NO 2
<211> LENGTH: 192
<212> TYPE: PRT
<213> ORGANISM: Homo sapiens

<400> SEQUENCE: 2

Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
    50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110
```

```
Asp Leu Leu Lys Asp Leu Glu Glu Gly Ile Gln Thr Leu Met Gly Arg
            115                 120                 125

Leu Glu Asp Gly Ser Pro Arg Thr Gly Gln Ile Phe Lys Gln Thr Tyr
    130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190

<210> SEQ ID NO 3
<211> LENGTH: 174
<212> TYPE: PRT
<213> ORGANISM: Homo sapiens

<400> SEQUENCE: 3

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
            35                  40                  45

Leu Leu Gly His Ser Leu Gly Ile Pro Trp Ala Pro Leu Ser Ser Cys
        50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
            85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
            115                 120                 125

Ala Leu Gln Pro Thr Gln Gly Ala Met Pro Ala Phe Ala Ser Ala Phe
            130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
            165                 170
```